(12) United States Patent
Shen et al.

(10) Patent No.: US 10,286,078 B2
(45) Date of Patent: May 14, 2019

(54) MODIFIED THERAPEUTIC AGENTS AND COMPOSITIONS THEREOF

(71) Applicants: THE CALIFORNIA INSTITUTE FOR BIOMEDICAL RESEARCH, La Jolla, CA (US); THE SCRIPPS RESEARCH INSTITUTE, La Jolla, CA (US)

(72) Inventors: Weijun Shen, San Diego, CA (US); Peter G. Schultz, La Jolla, CA (US); Avinash Muppidi, La Jolla, CA (US); Insha Ahmad, San Diego, CA (US); Pengyu Yang, San Diego, CA (US)

(73) Assignees: THE CALIFORNIA INSTITUTE FOR BIOMEDICAL RESEARCH, La Jolla, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 68 days.

(21) Appl. No.: 14/917,689

(22) PCT Filed: Sep. 12, 2014

(86) PCT No.: PCT/US2014/055457
§ 371 (c)(1),
(2) Date: Mar. 9, 2016

(87) PCT Pub. No.: WO2015/038938
PCT Pub. Date: Mar. 19, 2015

(65) Prior Publication Data
US 2016/0287713 A1    Oct. 6, 2016

Related U.S. Application Data

(60) Provisional application No. 61/877,799, filed on Sep. 13, 2013, provisional application No. 61/917,816, filed on Dec. 18, 2013.

(51) Int. Cl.
*A61K 38/22* (2006.01)
*A61K 9/00* (2006.01)
(Continued)

(52) U.S. Cl.
CPC .... *A61K 47/48046* (2013.01); *A61K 38/1709* (2013.01); *A61K 38/1825* (2013.01);
(Continued)

(58) Field of Classification Search
CPC ........ A61K 38/22; A61K 38/26; A61K 45/06; A61K 47/48023; A61K 47/48046;
(Continued)

(56) References Cited

U.S. PATENT DOCUMENTS 5,750,497 A    5/1998 Havelund et al.
5,759,807 A    6/1998 Breece et al.
(Continued)

FOREIGN PATENT DOCUMENTS

CA         2933701 A1    6/2015
WO    WO-2006066258 A2    6/2006
(Continued)

OTHER PUBLICATIONS

Guldenhaupt et al., Secondary structure of lipidated Ras bound to a lipid bilayer, FEBS Journal, vol. 275:5910-5918 (2008).*
(Continued)

*Primary Examiner* — Randall L Beane
(74) *Attorney, Agent, or Firm* — Wilson Sonsini Goodrich & Rosati

(57) ABSTRACT

Methods and compositions are provided for extending the half-life of a therapeutic agent. One or more half-life extending moieties may be attached to a therapeutic agent, thereby extending the half life of the therapeutic agent. The modified therapeutic agents (mTAs) comprising one or more half-life
(Continued)

extending moieties attached to a therapeutic agent may be used to treat a disease or condition in a subject in need thereof.

8 Claims, 12 Drawing Sheets

Specification includes a Sequence Listing.

(51) Int. Cl.
    *A61K 47/48*     (2006.01)
    *A61K 38/26*     (2006.01)
    *A61K 38/28*     (2006.01)
    *A61K 38/17*     (2006.01)
    *A61K 38/18*     (2006.01)
    *A61K 45/06*     (2006.01)
    *A61K 47/54*     (2017.01)

(52) U.S. Cl.
    CPC .......... *A61K 38/1875* (2013.01); *A61K 38/22* (2013.01); *A61K 38/2221* (2013.01); *A61K 38/2264* (2013.01); *A61K 38/26* (2013.01); *A61K 38/28* (2013.01); *A61K 45/06* (2013.01); *A61K 47/54* (2017.08); *A61K 47/543* (2017.08); *A61K 47/554* (2017.08)

(58) Field of Classification Search
    CPC .......... A61K 47/48123; A61K 38/1709; A61K 38/1825; A61K 38/1875; A61K 38/2221; A61K 38/2264; A61K 38/2278; A61K 38/28; A61K 47/48038; A61K 47/48215; A61K 9/00
    See application file for complete search history.

(56) References Cited

U.S. PATENT DOCUMENTS

| | | | |
|---|---|---|---|
| 5,811,395 A * | 9/1998 | Schwabe | C07K 14/64 514/12.7 |
| 5,866,538 A | 2/1999 | Norup et al. | |
| 6,011,007 A | 1/2000 | Havelund et al. | |
| 6,051,551 A | 4/2000 | Hughes et al. | |
| 6,268,343 B1 | 7/2001 | Knudsen et al. | |
| 6,444,641 B1 | 9/2002 | Flora | |
| 6,869,930 B1 | 3/2005 | Havelund et al. | |
| 6,890,518 B2 | 5/2005 | Patton et al. | |
| 8,129,343 B2 | 3/2012 | Lau et al. | |
| 8,217,145 B2 * | 7/2012 | Wang | C12N 9/104 435/183 |
| 8,420,598 B2 | 4/2013 | Lee et al. | |
| 8,735,539 B2 | 5/2014 | Kraynov et al. | |
| 2003/0158376 A1 | 8/2003 | Schwabe et al. | |
| 2005/0176108 A1 | 8/2005 | Kim et al. | |
| 2005/0192217 A1 * | 9/2005 | Muhlradt | A61K 38/164 514/9.4 |
| 2008/0305519 A1 | 12/2008 | Lin et al. | |
| 2009/0186817 A1 | 7/2009 | Ghosh et al. | |
| 2009/0239784 A1 | 9/2009 | Jonassen et al. | |
| 2010/0029554 A1 | 2/2010 | Ghosh et al. | |
| 2010/0184133 A1 | 7/2010 | Norgaard et al. | |
| 2010/0239554 A1 * | 9/2010 | Schellenberger | C07K 14/001 424/94.3 |
| 2010/0292172 A1 | 11/2010 | Ghosh et al. | |
| 2011/0046056 A1 | 2/2011 | Bianchi et al. | |
| 2011/0166321 A1 | 7/2011 | Garibay et al. | |
| 2011/0243942 A1 * | 10/2011 | Wang | C07K 14/64 424/134.1 |
| 2012/0046229 A1 * | 2/2012 | Kraynov | A61K 47/48215 514/12.7 |
| 2013/0040884 A1 | 2/2013 | Lau et al. | |
| 2013/0237481 A1 * | 9/2013 | Kraynov | C07K 14/64 514/12.7 |
| 2014/0148390 A1 | 5/2014 | Haupts et al. | |
| 2016/0317623 A1 | 11/2016 | Shen | |

FOREIGN PATENT DOCUMENTS

| | | |
|---|---|---|
| WO | WO-2006097537 A2 | 9/2006 |
| WO | WO-2007109135 A2 | 9/2007 |
| WO | WO-2008057298 A2 | 5/2008 |
| WO | WO-2010096052 A1 | 8/2010 |
| WO | WO-2010096142 A1 | 8/2010 |
| WO | WO-2011039096 A1 | 4/2011 |
| WO | WO-2012003995 A1 | 1/2012 |
| WO | WO-2012011752 A2 | 1/2012 |
| WO | WO-2012024452 A2 | 2/2012 |
| WO | WO-2012088116 A2 | 6/2012 |
| WO | WO-2012088379 A2 | 6/2012 |
| WO | WO-2012149563 A1 | 11/2012 |
| WO | WO-2013004607 A1 | 1/2013 |
| WO | WO-2013007563 A1 | 1/2013 |
| WO | WO-2013130683 A2 | 9/2013 |
| WO | WO-2015038938 A1 | 3/2015 |
| WO | WO-2016149501 A2 | 9/2016 |

OTHER PUBLICATIONS

Aicart-Ramos et al., Protein palmitoylation and subcellular trafficking, Biochimica et Biophysica Acta, vol. 1898:2981-2994 (2011).*
Pan et al., Design of a Long Acting Peptide Functioning as Both a Glucagon-like Peptide-1 Receptor Agonist and a Glucagon Receptor Antagonist, The Journal of Biological Chemistry, vol. 281(18):12506-12515 (May 5, 2006).*
Janout et al., Bioconjugate-Based Molecular Umbrellas, Bioconjugate Chemistry, vol. 20(2):183-192 (online Nov. 20, 2008).*
Muller, Chapter 2: Peptide-carrier conjugation, Synthetic Peptides as Antigens, Laboratory Techniques in Biochemistry and Molecular Biology, vol. 28 (1999), 79-131.*
Backer et al., Chapter 16: Cysteine-Containing Fusion Tag for Site-specific Conjugation of Therapeutic and Imaging Agents to Targeting Proteins, Peptide-Based Drug Design Methods and Protocols, Springer Protocols, 2008, 275-294.*
Chalker et al., Chemical Modification of Proteins at Cysteine: Opportunities in Chemistry and Biology, Chem. Asian J., vol. 4:630-640 (2009).*
Bader et al., Bioorganic synthesis of lipid-modified proteins for the study of signal transduction, Nature, vol. 403:223-226 (Jan. 13, 2000).*
Pollaro et al., Strategies to prolong the plasma residence time of peptide drugs, Med. Chem. Commun., vol. 1:319-324 (2010).*
Hossain et al., The minimal Active Structure of Human Relaxin-2, The Journal of Biological Chemistry, vol. 2286(43):37555-37565 (Oct. 28, 2011) (Year: 2011).*
Bird, Gregory H. et al. Hydrocarbon double-stapling remedies the proteolytic instability of a lengthy peptide therapeutic. Proceedings of the National Academy of Sciences, 2010, vol. 107, No. 32, pp. 14093-14098.
Bloom, Stephen R. et al. Investigation of Structure-Activity Relationships of Oxyntomodulin (Oxm) Using Oxm Analogs. Endocrinology 150(4):1712-1721 (Apr. 2009).
Chang, Y. et al. Stapled α—helical peptide drug development: A potent dual inhibitor of MDM2 and MDMX for p53-dependent cancer therapy, Proceedings of the National Academy of Sciences, e-pub. Aug. 14, 2013, vol. 110, No. 36, pp. E3445-E3454.
DiMarchi, Richard D. et al. Functional association of the N-terminal residues with the central region in glucagon-related peptides. J. Pept. Sci. 17:659-666 (2011).
DiMarchi, Richard et al. A new glucagon and GLP-1 co-agonist eliminates obesity in rodents. Nature Chemical Biology, 5(10):749-757 (Oct. 2009).
International Application No. PCT/US2014/055457 International Search Report and Written Opinion dated Dec. 23, 2014.
International Application No. PCT/US2014/070977 International Search Report and Written Opinion dated Mar. 27, 2015.

(56) References Cited

OTHER PUBLICATIONS

International Application No. PCT/US2016/022880 International Search Report and Written Opinion dated Oct. 7, 2016.
Metra, M. et al. Effect of Serelaxin on Cardiac, Renal, and Hepatic Biomarkers in the Relaxin in Acute Heart Failure (RELAX-AHF) Development Program. Journal of the American College of Cardiology 61(2): 196-206 (Jan. 15, 2013).
Santoprete, A. et al. DPP-IV-resistant, long-acting oxyntomodulin derivatives. Journal Peptide Science, 17:270-280 (2011).
Soloff, M. et al. Cloning, characterization, and expression of the rat relaxin gene. Gene 323: 149-155 (2003).
Underwood, Christina R. et al. Crystal Structure of Glucagon-like Peptide-1 in Complex with the Extracellular Domain of the Glucagon-like Peptide-1 Receptor. The Journal of Biological Chemistry 285(1): 723-730 (Jan. 1, 2010).
Wade, John D. et al. The Chemical Synthesis of Relaxin and Related peptides: A Historical Perspective. Ann. N.Y. Acad. Sci. 1160: 11-15 (2009).
Wu, Ye-Lin et al. Addition of a cysteine to glucagon-like peptide-1 (GLP-1) conjugates GLP-1 to albumin in serum and prolongs GLP-1 action in vivo, Regulatory Peptides, 2010, vol. 164, No. 2, pp. 83-89.
International Application No. PCT/US16/37834 International Search Report dated Oct. 26, 2016.
U.S. Appl. No. 15/104,807 Restriction Requirement dated Mar. 14, 2017.
Baosheng, Liu, Peptide PEGylation: The Next Generation Linking peptides to polythylene glycol, or PEGylation, has helped improve pharmaceutical therapeutics in several ways. A wave of new techniques is now ushering in further advances. Pharmaceutical Technology, 2011(3):1-3 (May 1, 2011).
Cheng, W. and Lee-Yong Lim, Design, synthesis, characterization and in-vivo activity of a novel salmon calcitonin conjugate containing a novel PEG-lipid moiety. Journal of Pharmacy and Pharmacology, 62(3):296-304 (Mar. 2010).
Cheng, W. et al. Lipeo-sCT: A novel reversible lipidized salmon calcitonin derivative, its biophysical properties and hypocalcemic activity. European Journal of Pharmaceutical Sciences 37(2):151-159 (May 12, 2009).
Elling, Christian E. et al. Oxyntomodulin Differentially Affects Glucagon-Like Peptide-1 Receptor β-Arrestin Recruitment and Signaling through Gαs. The Journal of Pharmacology and Experimental Therapeutics, 322(1):148-154 (2007).
Havelund, S. The mechanism of protraction of insulin detemir, a long-acting, acylated analog of human insulin. Pharmaceutical Research, 21(9):1498-1504 (Aug. 2004).
Hossain, Mohammed A. et al. Chimeric relaxin peptides highlight the role of the A-chain in the function of H2 relaxin. Peptides 35:102-106 (May 2012).
Shah, Trishul, Bioconjugates: The Adaptable Challenge. BioPharm International The Science & Business of Biopharmaceuticals, 26(1):1-4 (Jan. 1, 2013).
Teerlink, et al. Serelaxin, recombinant human relaxin-2, for treatment of acute heart failure (RELAX-AHF): a randomised, placebo-controlled trial. Lancet 381:29-39 (Jan. 2013).
Trussel, et al. New strategy for the extension of the serum half-life of antibody fragments. Bioconjug Chem. Dec. 2009;20(12):2286-92.
Co-pending U.S. Appl. No. 15/557,986, filed Sep. 13, 2017.
Lorenz, Martin et al. Recent progress and future options in the development of GLP-1 receptor agonists for the treatment of diabesity. Bioorganic & Medicinal Chemistry Letters 23 (14): 4011-4018 (May 16, 2013).
U.S. Appl. No. 15/104,807 Non-final Office Action dated Nov. 27, 2017.

\* cited by examiner

FIG. 1

H2-Relaxin - SB29C

A-chain  Z-L-Y-S-A-L-A-N-K-C-C-H-V-G-C-T-K-R-S-L-A-R-F-C (SEQ ID NO: 53)
B-chain  D-S-W-M-E-E-V-I-K-L-C-G-R-E-L-V-R-A-Q-I-A-I-C-G-M-S-T-W-C (SEQ ID NO: 16)

FIG. 2
H2-Relaxin modifications
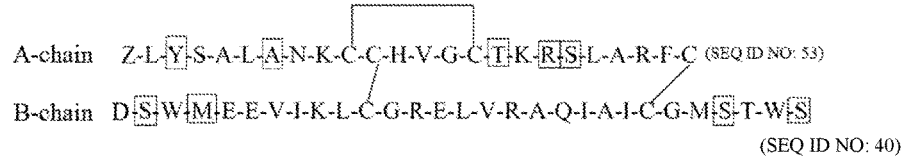
Relaxin-B-D1A modifications
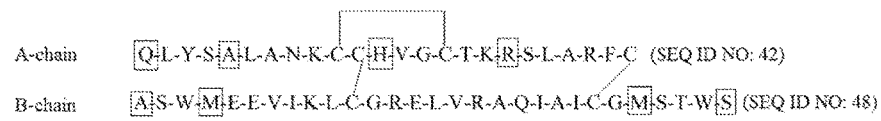
FIG. 3
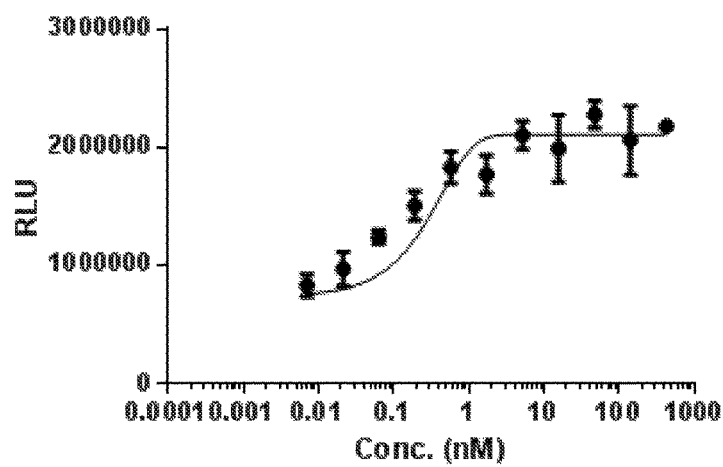

FIG. 10
FIG. 11
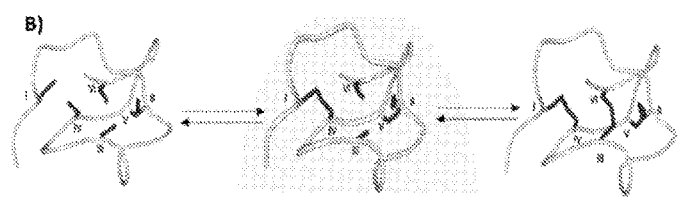
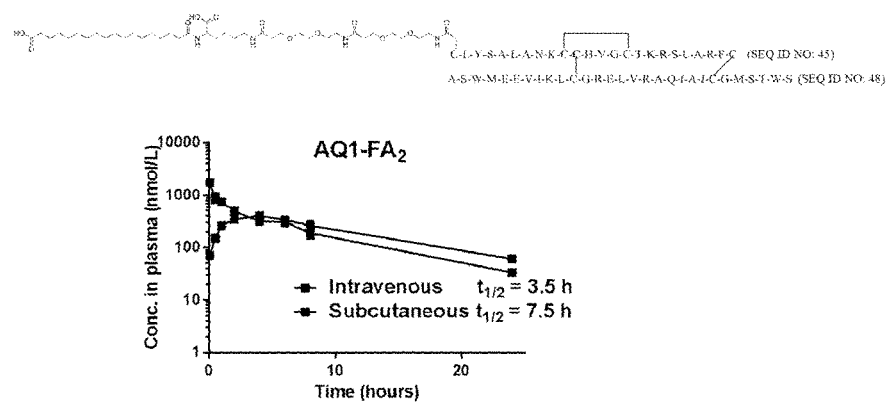

FIG. 16A

| Entry | NAME | Lipid Conjugate Structure |
|---|---|---|
| 1 | Relaxin-B-D1A,A-Q1C-X | C-L-Y-S-A-L-A-N-K-C-C-H-V-G-C-T-K-R-S-L-A-R-F-C (SEQ ID NO: 45)<br>A-S-W-M-E-E-V-I-K-L-C-G-R-E-L-V-R-A-Q-I-A-I-C-G-M-S-T-W-S (SEQ ID NO: 48) |
| 2 | Relaxin-B-D1C-X | Q-L-Y-S-A-L-A-N-K-C-C-H-V-G-C-T-K-R-S-L-A-R-F-C (SEQ ID NO: 43)<br>C-S-W-M-E-E-V-I-K-L-C-G-R-E-L-V-R-A-Q-I-A-I-C-G-M-S-T-W-S (SEQ ID NO: 52) |
| 3 | Relaxin-B-D1A,A-A5C-X | Q-L-Y-S-C-L-A-N-K-C-C-H-V-G-C-T-K-R-S-L-A-R-F-C (SEQ ID NO: 45)<br>A-S-W-M-E-E-V-I-K-L-C-G-R-E-L-V-R-A-Q-I-A-I-C-G-M-S-T-W-S (SEQ ID NO: 48) |
| 4 | Relaxin-B-D1A,A-R18C-X | Q-L-Y-S-A-L-A-N-K-C-C-H-V-G-C-T-K-C-S-L-A-R-F-C (SEQ ID NO: 55)<br>A-S-W-M-E-E-V-I-K-L-C-G-R-E-L-V-R-A-Q-I-A-I-C-G-M-S-T-W-S (SEQ ID NO: 48) |
| 5 | Relaxin-B-D1AS29C-X | Q-L-Y-S-A-L-A-N-K-C-C-H-V-G-C-T-K-R-S-L-A-R-F-C (SEQ ID NO: 45)<br>A-S-W-M-E-E-V-I-K-L-C-G-R-E-L-V-R-A-Q-I-A-I-C-G-M-S-T-W-C (SEQ ID NO: 49) |
| 6 | Relaxin-B-D1AM25KM4K,A-Q1AH12A,B-S29C-X | A-L-Y-S-A-L-A-N-K-C-C-A-V-G-C-T-K-R-S-L-A-R-F-C (SEQ ID NO: 46)<br>A-S-W-K-E-E-V-I-K-L-C-G-R-E-L-V-R-A-Q-I-A-I-C-G-K-S-T-W-C (SEQ ID NO: 50) |
| 7 | Relaxin-B-D1AM25KM4K,A-Q1AH12K,B-S29C-X | A-L-Y-S-A-L-A-N-K-C-C-K-V-G-C-T-K-R-S-L-A-R-F-C (SEQ ID NO: 47)<br>A-S-W-K-E-E-V-I-K-L-C-G-R-E-L-V-R-A-Q-I-A-I-C-G-K-S-T-W-C (SEQ ID NO: 51) |

FIG. 16B

| Entry | NAME | Lipid Conjugate Structure |
|---|---|---|
| 8 | Relaxin-B-D1AM4KS29C-X | Q-L-Y-S-A-L-A-N-K-C-C-H-V-G-C-T-K-R-S-L-A-R-F-C (SEQ ID NO: 42)<br>A-S-W-K-E-E-V-I-K-L-C-G-R-E-L-V-R-A-Q-I-A-I-C-G-M-S-T-W-C (SEQ ID NO: 51)<br>       X |
| 9 | Relaxin-A-H12K,B-D1AS29C-X | Q-L-Y-S-A-L-A-N-K-C-C-K-V-G-C-T-K-R-S-L-A-R-F-C (SEQ ID NO: 44)<br>A-S-W-M-E-E-V-I-K-L-C-G-R-E-L-V-R-A-Q-I-A-I-C-G-M-S-T-W-C (SEQ ID NO: 49)<br>       X |
| 10 | Relaxin-B-D1AM25KS29C-X | Q-L-Y-S-A-L-A-N-K-C-C-H-V-G-C-T-K-R-S-L-A-R-F-C (SEQ ID NO: 42)<br>A-S-W-M-E-E-V-I-K-L-C-G-R-E-L-V-R-A-Q-I-A-I-C-G-K-S-T-W-C (SEQ ID NO: 86)<br>       X |
| 11 | 550-4-GSCGG-X | GSCGGECIGMFKSCDPENDKCCKGRTCSRKHRWCKYKL (SEQ ID NO: 28)<br>  X |
| 12 | 550-3-GSGG-X | GSGGECIGMFKSCDPENDKCCKGRTCSRKHRWCKYKLC (SEQ ID NO: 29)<br>       X |
| 13 | 550-3-GGS-X | ECIGMFKSCDPENDKCCKGRTCSRKHRWCKYKLGGSC (SEQ ID NO: 31)<br>       X |

MODIFIED THERAPEUTIC AGENTS AND COMPOSITIONS THEREOF

CROSS-REFERENCE TO RELATED APPLICATIONS

This application is a U.S. National Stage entry of International Application No. PCT/US2014/055457, filed Sep. 12, 2014, which claims the benefit of U.S. Provisional Application No. 61/877,799 filed Sep. 13, 2013, and U.S. Provisional Application No. 61/917,816 filed Dec. 18, 2013, all of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 2, 2014, is named 41135-709-831-b ST25.txt and is 51,371 bytes in size.

BACKGROUND OF THE INVENTION

The development of therapeutic agents (e.g., biological drugs) is often hampered by short half-lives. The biological half-life or elimination half-life of a substance is the time it takes for a substance (for example a metabolite, drug, signaling molecule, radioactive nuclide, or other substance) to lose half of its pharmacologic, physiologic, or radiologic activity. As a result of the short half-life, patients are often administered higher dosages more frequently, which may lead to reduced compliance, higher costs and greater risks of side effects.

Extended-release products are designed to prolong the absorption of drugs with short half-lives, thereby allowing longer dosing intervals while minimizing fluctuations in serum drug levels. Current strategies used for extending half-lives are those that increase hydrodynamic volume (PEGylation) or those that use FcRn-mediated recycling (albumin fusions). Attachment of polypeptides or lipophilic constituents to drugs has also been used to extend the half-life of a biological agent (U.S. Pat. Nos. 6,268,343; 5,750,497; 8,129,343).

The present disclosure provides modified therapeutic agents (mTAs) for improving the biological, chemical, physiologic, pharmacologic, pharmacokinetic, and/or pharmacodynamic properties of a therapeutic agent.

SUMMARY OF THE INVENTION

Methods and compositions are provided for the formation of modified therapeutic agents. The modified therapeutic agents (mTAs) may comprise a therapeutic agent and one or more half-life extending moieties, wherein the therapeutic agent is a peptide that is covalently attached to each of the one or more half-life extending moieties via a cysteine residue on the peptide; and the half-life of the modified therapeutic agent is longer than the half-life of the peptide alone. The mTAs may comprise two or more half-life extending moieties. The two or more half-life extending moieties may be identical. The two or more half-life extending moieties may be different. A half-life extending moiety of the one or more half-life extending moieties may comprise a lipid, a polyglycol region, or a combination thereof. Each of the one or more half-life extending moieties may comprise a lipid. A half-life extending moiety of the one or more half-life extending moieties may comprise a polyglycol region. A half-life extending moiety of the one or more half-life extending moieties may comprise a lipid and a polyglycol region. A half-life extending moiety of the one or more half-life extending moieties may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 70% homologous to an amino acid sequence selected from SEQ ID NOs: 66-67. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region may comprise one or more polyethylene glycol units, polypropylene glycol units, or polybutylene glycol units, or a combination thereof. The polyglycol region may comprise one thousand or more polyethylene glycol units, polypropylene glycol units, or polybutylene glycol units, or a combination thereof. The peptide may comprise one or more amino acid additions, deletions, or substitutions, or a combination thereof. The peptide may be selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof. The peptide may be selected from relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, Toxin-550, Moka, and VM-24, or a derivative thereof, the derivative being a peptide comprising one or more amino acid additions, deletions, or substitutions, or a combination thereof. The peptide may be relaxin or a derivative thereof, the derivative being a peptide comprising one or more amino acid additions, deletions, or substitutions, or a combination thereof. The peptide may be encoded by an amino acid sequence comprising at least a portion of a polypeptide sequence selected from a group consisting of SEQ ID NO: 10-56. The peptide may be encoded by an amino acid sequence comprising 10 or more amino acids based on or derived from a polypeptide sequence selected from a group consisting of SEQ ID NO: 10-56. The peptide may comprise an amino acid sequence that is at least about 50% homologous to an amino acid sequence selected from the group comprising SEQ ID NO: 10-56. The peptide may comprise an amino acid sequence that is at least 80% homologous to an amino acid sequence selected from the group comprising SEQ ID NO: 10-56. The peptide may comprise one or more amino acid sequences selected from the group comprising SEQ ID NO: 10-56. The peptide may comprise two or more amino acid sequences selected from the group comprising SEQ ID NO: 10-56. The cysteine residue may be located on the N-terminus or C-terminus of the peptide. The cysteine residue may be located on a non-terminus position of the peptide. The cysteine residue may be an amino acid addition or substitution on the peptide. The cysteine residue may be an amino acid addition or substitution on a wild-type peptide.

Methods and compositions are provided for the formation of lipid conjugates (LCs). The lipid conjugates (LCs) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA is a peptide and the one or more lipids are conjugated to the TA via an amino acid residue on the peptide. The amino acid residue may be a cysteine or lysine. The amino acid residue may be a cysteine. The amino acid residue may be an amino acid addition or amino acid substitution on the peptide. The amino acid residue may be located at the N-terminus or C-terminus of the peptide. The amino acid residue may be located at a non-terminus position of the peptide. The TA may be a peptide comprising one or more amino acid additions, deletions, or substitutions, or a combination thereof. One or more cysteine or lysine residues may be introduced by the one or more amino acid additions or substitutions or a combination thereof. The lipid conjugates (LCs) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein is a lipid conjugate (LC) comprising (a) one or more lipids, the lipids selected from sterols, sterol derivatives, bile acids, vitamin E derivatives, fatty di-acids, fatty acids, fatty amides, fatty amines, and fatty alcohols, and derivatives thereof, and (b) a therapeutic agent (TA), wherein the TA comprises a relaxin peptide or derivative thereof and the one or more lipids are conjugated to the TA via an amino acid residue on the peptide. Further disclosed herein is a lipid conjugate (LC) comprising (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide, or derivative thereof, wherein the one or more lipids are attached to the one or more therapeutic agent via a cysteine residue.

Further disclosed herein is a lipid conjugate (LC) comprising one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. Further disclosed herein is a lipid conjugate (LC) comprising (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA comprises a modified relaxin peptide, and wherein the modified relaxin peptide comprises a wild-type relaxin polypeptide with one or more amino acid mutations.

Disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA is a peptide and the one or more lipids are conjugated to the TA via an amino acid residue on the peptide.

Further disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue.

Further disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA comprises a relaxin peptide or derivative thereof and the one or more lipids are conjugated to the TA via an amino acid residue on the peptide.

Further disclosed herein are pharmaceutical compositions comprising an LC, wherein the LC comprises one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations.

Further disclosed herein are pharmaceutical compositions comprising an LC, wherein the LC comprises one or more lipids attached to a therapeutic agent (TA), wherein the TA comprises a modified relaxin peptide, and wherein the modified relaxin peptide comprises a wild-type relaxin polypeptide with one or more amino acid mutations.

Disclosed herein is a method for treating a disease or condition in a subject in need thereof, the method comprising administering to the subject a composition comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA is a peptide and the one or more lipids are conjugated to the TA via an amino acid residue on the peptide.

Further disclosed herein is a method for treating a disease or condition in a subject in need thereof, the method comprising administering to the subject a composition comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein are methods of treating a disease or condition in a subject in need thereof, the method comprising administering to the subject a composition comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue.

Further disclosed herein are methods of treating a disease or condition in a subject in need thereof, the method comprising administering to the subject a composition comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA comprises a relaxin peptide or derivative thereof and the one or more lipids are conjugated to the TA via an amino acid residue on the peptide.

Further disclosed herein are methods of treating a disease or condition in a subject in need thereof, the method comprising administering to the subject a composition comprising an LC, wherein the LC comprises one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations.

Further disclosed herein are methods of treating a disease or condition in a subject in need thereof, the method comprising administering to the subject a composition comprising an LC, wherein the LC comprises one or more lipids attached to a therapeutic agent (TA) wherein the TA comprises a modified relaxin peptide, and wherein the modified relaxin peptide comprises a wild-type relaxin polypeptide with one or more amino acid mutations.

Disclosed herein are kits comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA is a peptide and the one or more lipids are conjugated to the TA via an amino acid residue on the peptide.

Further disclosed herein are kits comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein are kits comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA comprises a relaxin peptide or derivative thereof, and the one or more lipids are conjugated to the TA via an amino acid residue on the peptide.

Further disclosed herein are kits comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, and the one or more lipids are attached to the one or more therapeutic agent via a cysteine residue.

Further disclosed herein are kits comprising an LC, wherein the LC comprises one or more lipids attached to a therapeutic agent (TA), wherein the TA comprises a modified relaxin peptide, and wherein the modified relaxin peptide comprises a wild-type relaxin polypeptide with one or more amino acid mutations.

Further disclosed herein are kits comprising an LC, wherein the LC comprises one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations.

Disclosed herein is a vector comprising a polynucleotide sequence of SEQ ID NO: 1-9.

Disclosed herein is a host cell comprising a polynucleotide sequence of SEQ ID NO: 1-9.

Disclosed herein is a vector comprising a polynucleotide sequence encoding a polypeptide of SEQ ID NO: 10-56.

Disclosed herein is a host cell comprising a polynucleotide sequence encoding a polypeptide of SEQ ID NO: 10-56.

The LCs disclosed herein may further comprise one or more polyethyleneglycol subunits.

The LCs disclosed herein may comprise one or more pegylated lipids.

The LC may have the structure:

$$TA\text{-}A^1\text{-}P^1\text{-}L \qquad \text{Formula (I)}$$

wherein: TA is the therapeutic agent; $A^1$ is a chemical group linking TA and $P^1$ or L; $P^1$ is a bond or comprises polyglycol; and L is the lipid. $P^1$ may be a bond. A sulfur or nitrogen atom of an amino acid residue of TA may be connected to $A^1$ via a chemical bond. $P^1$ may comprise polyglycol. $P^1$ may be -PEG-$A^2$-; wherein PEG is a chemical group comprising one or more polyethyleneglycol subunits; and $A^2$ is a chemical group linking PEG and L. PEG may be selected from

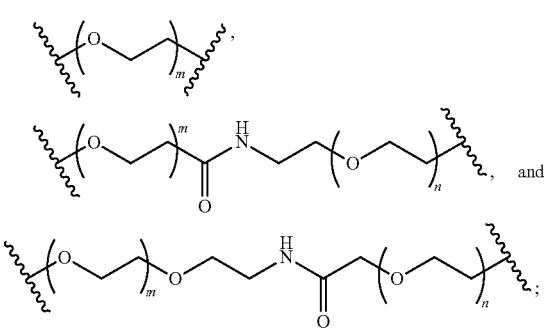

wherein m and n are independently 1, 2, 3, 4, 5, 6, 7, 8, 9, 10, 11, 12, 13, 14, 15, 16, 17, 18, 19, or 20. The one or more lipids may be selected from a group consisting of octadecanedioic acid, tetradecylamine, myristic acid, stearic acid, docosahexaenoic acid, lithocholic acid ester, cholic acid and palmitic acid.

In some embodiments described herein of an LC of Formula (I), $A^1$ is selected from

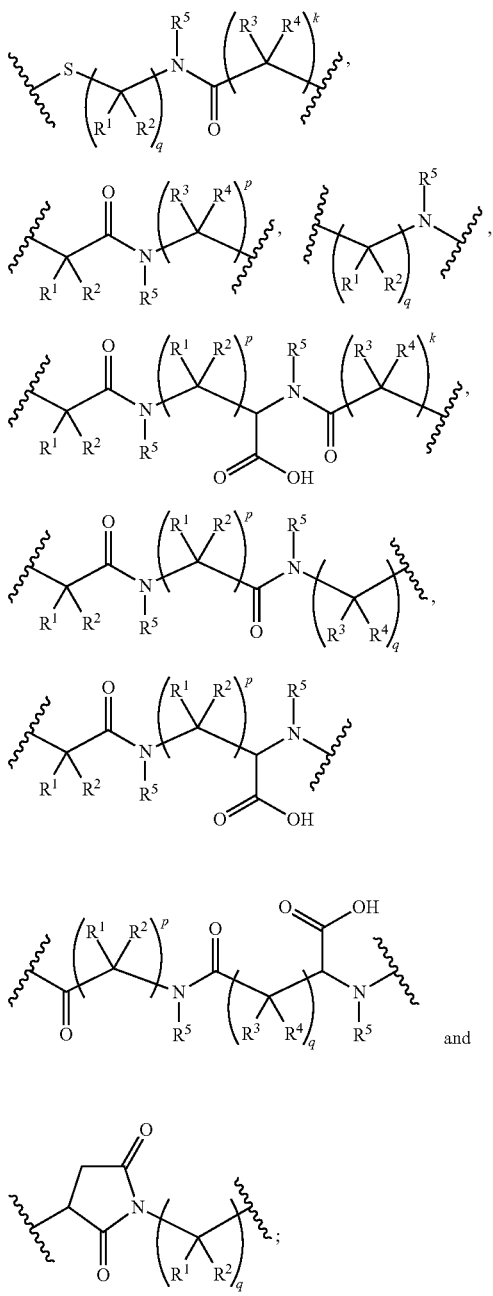

and each $R^1$, $R^2$, $R^3$, and $R^4$ is independently selected from H, halo, CN, —$SR^5$, alkyl, cycloalkyl, haloalkyl, —$NR^5R^5$, —$NC(O)R^5$, —$NC(O)OR^5$, and —$OR^5$;

each $R^5$ is independently H, alkyl, haloalkyl, arylalkyl, (cycloalkyl)alkyl, or heteroalkyl;

k is 1, 2, 3, 4, 5, 6, 7, 8, 9, or 10;

p is 2, 3, 4, 5, 6, 7, 8, 9, or 10; and q is 2, 3, 4, 5, 6, 7, 8, 9, or 10.

In some embodiments described herein of an LC of Formula (I), $A^2$ is selected from a bond,

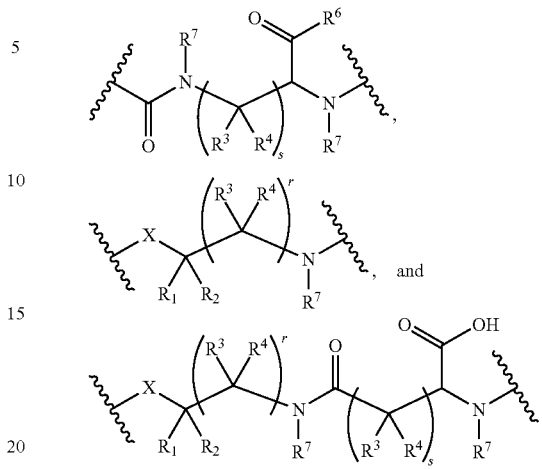

X is a bond, $NR^5$, S, or O;

each $R^1$, $R^2$, $R^3$, and $R^4$ is independently selected from H, halo, CN, —$SR^5$, alkyl, cycloalkyl, haloalkyl, —$NR^5R^5$, and —$OR^5$;

each $R^5$ is independently H, alkyl, haloalkyl, arylalkyl, or heteroalkyl; $R^6$ is OH or —$NR^5R^5$;

each $R^7$ is independently selected from H, alkyl, haloalkyl, arylalkyl, and heteroalkyl;

r is 1, 2, 3, 4, 5, 6, 7, 8, 9, or 10; and s is 1, 2, 3, 4, or 5.

The LC may have the structure:

TA-$A^1$-$P^1$-L    Formula (Ia)

wherein: TA is the therapeutic agent with a cysteine residue, wherein the cysteine residue is connected to $A^1$; $A^1$ is a chemical group linking TA and $P^1$; $P^1$ is a bond or -PEG-$A^2$-; PEG is a chemical group comprising one or more polyethyleneglycol subunits; $A^2$ is a chemical group linking PEG and L; and L is the lipid.

The sulfur atom of the cysteine residue of the TA of Formula (Ia) may be connected to $A^1$ via a chemical bond.

The PEG of an LC of Formula (Ia) may be selected from:

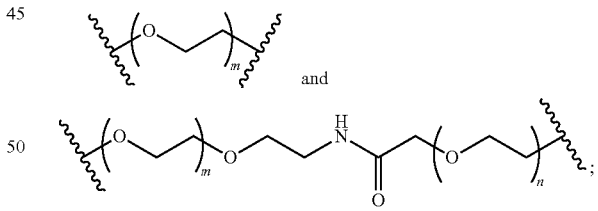

wherein m and n may independently be 1, 2, 3, 4, 5, 6, 7, 8, 9, 10, 11, 12, 13, 14, 15, 16, 17, 18, 19, or 20.

In some embodiments described herein of an LC of Formula (Ia), $A^1$ is selected from

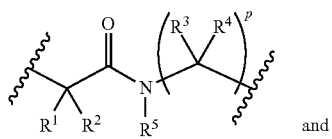

and

-continued

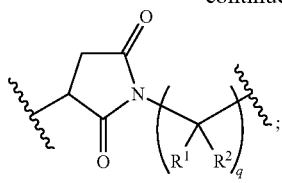

and
R$^1$, R$^2$, R$^3$, and R$^4$ are independently selected from H, halo, CN, —SR$^5$, alkyl, cycloalkyl, haloalkyl, —NR$^5$R$^5$, and —OR$^5$;
R$^5$ is H, alkyl, haloalkyl, arylalkyl, or heteroalkyl;
p is 2, 3, 4, 5, 6, 7, 8, 9, or 10; and
q is 2, 3, 4, 5, 6, 7, 8, 9, or 10.
In some embodiments described herein of an LC of Formula (Ia),
A$^2$ is selected from a bond,

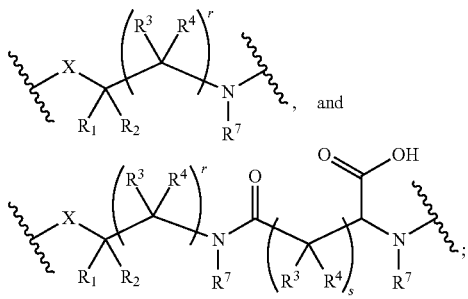

X is a bond, NR$^5$, or 0;
R$^1$, R$^2$, R$^3$, and R$^4$ are independently selected from H, halo, CN, —SR$^5$, alkyl, cycloalkyl, haloalkyl, —NR$^5$R$^5$, and —OR$^5$;
R$^5$ is H, alkyl, haloalkyl, arylalkyl, or heteroalkyl;
each R$^7$ is independently selected from H, alkyl, haloalkyl, arylalkyl, and heteroalkyl;
r is 1, 2, 3, 4, 5, 6, 7, 8, 9, or 10; and
s is 1, 2, 3, 4, or 5.
P$^1$ may be PEG-A$^2$ for an LC of Formula (Ia).
The LC of Formula (I) or (Ia) may comprise a TA comprising a modified relaxin peptide. The LC of Formula (I) or (Ia) may comprise one or more lipids selected from sterols, sterol derivatives, bile acids, vitamin E derivatives, fatty di-acids, fatty acids, fatty amides, and fatty alcohols.

Attachment of the one or more lipids to the therapeutic agent may comprise covalent attachment. Attachment of the one or more lipids to the modified relaxin peptide may comprise covalent attachment.

The one or more lipids may be attached to a therapeutic agent via a cysteine residue. The one or more lipids may be attached to the modified relaxin via a cysteine residue.

Disclosed herein is a compound having the structure of A$^3$-P$^1$-L, wherein: A$^3$ is a haloacetamide, maleimide, benzyl halide, or pyridyl disulfide; P$^1$ is a bond or -PEG-A$^2$-; PEG is a chemical group comprising one or more polyethyleneglycol subunits; A$^2$ is a chemical group linking PEG and L; and L is a lipid selected from sterols, sterol derivatives, bile acids, vitamin E derivatives, fatty di-acids, fatty acids, fatty amides, and fatty alcohols.

Further disclosed herein is a compound having the structure of A$^3$-P$^1$-L, wherein: A$^3$ is a haloacetamide, maleimide, benzyl halide, or pyridyl disulfide; P$^1$ is a bond or comprises polyglycol; and L is a lipid selected from sterols, sterol derivatives, bile acids, vitamin E derivatives, fatty di-acids, fatty acids, fatty amides, fatty amines, and fatty alcohols.

Disclosed herein are methods and compositions comprising one or more lipids. The one or more lipids may be selected from a group consisting of saturated fatty acids, unsaturated fatty acids, fatty di-acids, fatty amides, polyunsaturated fatty acids, short-chain fatty acids, medium chain fatty acids, long chain fatty acid and very long chain fatty acids.

The lipids may be selected from a group consisting of propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, myristic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid and hexatriacontanoic acid.

The one or more lipids may be selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosapentanoic acid, erucic acid, docosahexaenoic acid.

The one or more lipids may be selected from a group consisting of octadecanedioic acid, tetradecylamine, myristic acid, stearic acid, docosahexaenoic acid, lithocholic acid ester, cholic acid and palmitic acid.

The one or more lipids may comprise myristic acid. The one or more lipids may comprise docosahexanoic acid. The one or more lipids may comprise lithocholic acid ester. The one or more lipids may comprise cholic acid. The one or more lipids may comprise palmitic acid. The one or more lipids may comprise octadecanedioic acid. The one or more lipids may comprise tetradecylamine. The one or more lipids may comprise stearic acid.

The fatty acids may comprise at least about 6, 7, 8, 9, 10, 11, 12, 13, 14, 15, 16, 17, 18, 19, 20, 21, 22, 23, 24, 25, 26, 27, 28, 29, 30 or more carbon atoms.

The one or more lipids may comprise fatty alcohols derived from fatty acids selected from a group consisting of saturated fatty acids, unsaturated fatty acids, polyunsaturated fatty acids, short-chain fatty acids, medium chain fatty acids, long chain fatty acid and very long chain fatty acids.

The one or more lipids may be selected from a group consisting of cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, and glycochenodeoxycholic acid.

The one or more lipids may be selected from a group consisting of cholic acid, chenodeoxycholic acid, lithocholic acid, deoxycholic acid, glycocholic acid, glycodeoxycholic acid, glycolithocholic acid, and glycochenodeoxycholic acid.

The one or more lipids may be selected from a group consisting of α-tocopherol, β-tocopherol, γ-tocopherol, δ-tocopherol, α-tocotrienol, β-tocotrienol, γ-tocotrienol and δ-tocotrienol.

Disclosed herein are methods and compositions comprising one or more therapeutic agents (TAs). The methods and compositions may comprise a therapeutic agent (TA). The one or more TAs may comprise at least a portion of a protein, biomolecule, chemical, toxin, drug or any combination thereof.

The one or more TAs may comprise at least a portion of a hormone, kinase, receptor, ligand, growth factor, regulatory protein, metabolic protein, cytokine, antibody or any combination thereof.

The one or more TAs may comprise a peptide selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, and derivatives thereof, the derivative being a peptide comprising one or more amino acid additions, deletions, or substitutions, or a combination thereof. The one or more TAs may comprise relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, or VM-24, or a derivative thereof, the derivative being a peptide comprising one or more amino acid additions, deletions, or substitutions, or a combination thereof. The one or more TAs may comprise oxyntomodulin, exenatide, exendin-4, glucagon-like protein-1 (GLP-1), GLP-2, glucagon, a GLP-1R and GIPR dual agonist, or a GLP-1R and GCGR dual agonist, or a derivative thereof, the derivative being a peptide comprising one or more amino acid additions, deletions, or substitutions, or a combination thereof. The one or more TAs may comprise H1 relaxin, H2 relaxin, H3 relaxin, human INSL3, human INSL4, human INSL6, human IGF1, human IGFII, or human insulin, or a derivative thereof, the derivative being a peptide comprising one or more amino acid additions, deletions, or substitutions, or a combination thereof. The one or more TAs may comprise a peptidyl toxin or a derivative thereof, the derivative being a peptide comprising one or more amino acid additions, deletions, or substitutions, or a combination thereof. The peptidyl toxin or a derivative thereof may be refolded using a refolding buffer comprising ammonium sulfate.

The one or more TAs may comprise a relaxin peptide or derivative thereof, the derivative being a peptide comprising one or more amino acid additions, deletions, or substitutions, or a combination thereof. The relaxin derivative may comprise a modified A-chain of relaxin comprising one or more amino acids that have been added, deleted, or substituted, or a combination thereof. The relaxin derivative may comprise a modified B-chain of relaxin comprising one or more amino acids that have been added, deleted, or substituted, or a combination thereof. The relaxin derivative may comprise a modified A-chain of relaxin comprising one or more amino acids that have been added, deleted, or substituted, or a combination thereof; and a modified B-chain of relaxin comprising one or more amino acids that have been added, deleted, or substituted, or a combination thereof. The relaxin derivative may comprise a modified prorelaxin comprising one or more amino acids that have been added, deleted, or substituted, or a combination thereof.

The TA may be oxyntomodulin or derivative thereof, the derivative being a peptide comprising one or more amino acid additions, deletions, or substitutions, or a combination thereof. The TA may be exendin-4 or derivative thereof, the derivative being a peptide comprising one or more amino acid additions, deletions, or substitutions, or a combination thereof. The TA may be exenatide or derivative thereof, the derivative being a peptide comprising one or more amino acid additions, deletions, or substitutions, or a combination thereof. The TA may be glucagon-like peptide (GLP-1) or derivative thereof, the derivative being a peptide comprising one or more amino acid additions, deletions, or substitutions, or a combination thereof. The TA may be glucagon or derivative thereof, the derivative being a peptide comprising one or more amino acid additions, deletions, or substitutions, or a combination thereof.

The one or more TAs may be encoded by a nucleotide sequence selected from a group consisting of SEQ ID NO: 1-9.

The one or more TAs may be encoded by a nucleotide sequence comprising 20 or more nucleotides based on or derived from a nucleotide sequence selected from a group consisting of SEQ ID NO: 1-9.

The one or more TAs may be encoded by a nucleotide sequence that is at least about 50% homologous to a nucleotide sequence selected from a group consisting of SEQ ID NO: 1-9.

The one or more TAs may be encoded by a nucleotide sequence that is at least about 55%, 60%, 65%, 70%, 75%, 80%, 85%, 90%, 95%, 97%, 99% homologous to a nucleotide sequence selected from a group consisting of SEQ ID NO: 1-9.

The one or more TAs may be encoded by a nucleotide sequence comprising 200 or fewer nucleotides.

The one or more TAs may be encoded by a nucleotide sequence comprising 60-1500 or fewer nucleotides.

The one or more TAs may be encoded by an amino acid sequence comprising at least a portion of a polypeptide sequence selected from a group consisting of SEQ ID NO: 10-56.

The one or more TAs are encoded by an amino acid sequence may comprise 10 or more amino acids based on or derived from a polypeptide sequence selected from a group consisting of SEQ ID NO: 10-56.

The one or more TAs may comprise an amino acid sequence comprising 20-500 or more amino acids based on or derived from an amino acid sequence selected from a group consisting of SEQ ID NO: 10-56.

The one or more TAs may comprise an amino acid sequence that is at least about 50% homologous to an amino acid sequence selected from the group comprising SEQ ID NO: 10-56.

The one or more TAs may comprise an amino acid sequence that is at least about 55%, 60%, 65%, 70%, 75%, 80%, 85%, 90%, 92%, 95%, 97% or 99% homologous to an amino acid sequence selected from the group comprising SEQ ID NO: 10-56.

The one or more TAs may comprise a relaxin peptide. The relaxin peptide may comprise a modified relaxin peptide. The modified relaxin peptide may comprise at least a portion of a wild-type relaxin peptide comprising one or more amino acid mutations. The relaxin peptide may comprise at least a portion of an A chain and/or B chain of a relaxin peptide.

The relaxin peptide may comprise one or more amino acid mutations. The one or more amino acid mutations may comprise a deletion, substitution, addition or a combination thereof. The one or more amino acid mutations may comprise addition of one or more amino acid residues to the wild-type relaxin polypeptide. The one or more amino acid mutations may comprise substitution of one or more amino acid residues of the wild-type relaxin polypeptide. The one or more amino acid mutations may comprise deletion of one or more amino acid residues of the wild-type relaxin polypeptide.

The one or more amino acid mutations may comprise one or more amino acid substitutions of one or more amino acid residues in an A chain and/or B chain of a wild-type relaxin peptide. The one or more amino acid mutations may comprise one or more amino acid substitutions of one or more amino acid residues in an A chain of a wild-type relaxin peptide. The one or more amino acid substitutions of one or more amino acid residues in the A chain may be selected from a group consisting of Y3C, A7C, T16C, R18C, S19C, or a combination thereof. The one or more amino acid mutations may comprise one or more amino acid substitutions of one or more amino acid residues in a B chain of a wild-type relaxin peptide. The one or more amino acid substitutions of one or more amino acid residues in the B chain may be selected from a group consisting of S2C, M4C, S26C, and S29C, or any combination thereof. The one or more amino acid mutations may comprise a Y3C substitution in an A chain of a wild-type relaxin peptide. The one or more amino acid mutations may comprise an A7C substitution in an A chain of a wild-type relaxin peptide. The one or more amino acid mutations may comprise a T16C substitution in an A chain of a wild-type relaxin peptide. The one or more amino acid mutations may comprise a R18C substitution in an A chain of a wild-type relaxin peptide. The one or more amino acid mutations may comprise a S19C substitution in an A chain of a wild-type relaxin peptide. The one or more amino acid mutations may comprise a S2C substitution in a B chain of a wild-type relaxin peptide. The one or more amino acid mutations may comprise a M4C substitution in a B chain of a wild-type relaxin peptide. The one or more amino acid mutations may comprise a S26C substitution in a B chain of a wild-type relaxin peptide. The one or more amino acid mutations may comprise a S29C substitution in a B chain of a wild-type relaxin peptide.

The one or more amino acid mutations may comprise substituting one or more amino acid residues of a wild-type relaxin peptide with a cysteine residue. The one or more amino acid residues of the wild-type relaxin peptide may be selected from a group consisting of alanine, methionine, arginine, serine, threonine, and tyrosine.

The one or more amino acid mutations may comprise adding one or more amino acid residues to a wild-type relaxin peptide.

The one or more lipids for use in the methods and compositions disclosed herein may enhance one or more pharmacokinetic properties of the one or more TAs.

The one or more lipids may enhance one or more pharmacokinetic properties of the one or more TAs by at least about 200% as measured by pharmacodynamics when compared to the one or more TAs not attached to the one or more lipids. The one or more lipids may enhance one or more pharmokinetic properties of a TA by at least about 250% as measured by pharmacodynamics when compared to the TA not attached to the one or more lipids.

The one or more pharmacokinetic properties may comprise a half-life.

Disclosed herein are compounds having the structure of $A^3$-$P^1$-L, wherein: $A^3$ may be a haloacetamide, maleimide, benzyl halide, or pyridyl disulfide; $P^1$ may be a bond or -PEG-$A^2$-; $A^2$ may be a chemical group linking PEG and L; L may be a lipid selected from sterols, sterol derivatives, bile acids, vitamin E derivatives, fatty di-acids, fatty acids, fatty amides, and fatty alcohols; and PEG may be selected from:

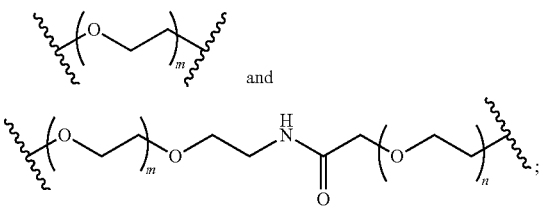

and wherein
m and n may be independently 1, 2, 3, 4, 5, 6, 7, 8, 9, 10, 11, 12, 13, 14, 15, 16, 17, 18, 19, or 20.

In some embodiments described herein,
$A^2$ is selected from a bond,

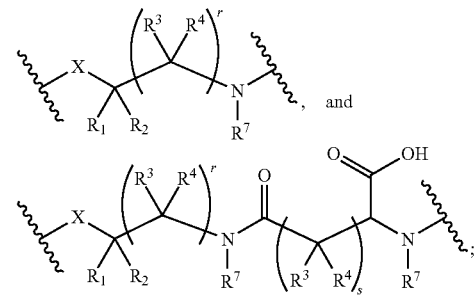

and

X is a bond, $NR^5$, or O;
$R^1$, $R^2$, $R^3$, and $R^4$ are independently selected from H, halo, CN, —$SR^5$, alkyl, cycloalkyl, haloalkyl, —$NR^5R^5$, and —$OR^5$; $R^5$ is H, alkyl, haloalkyl, arylalkyl, or heteroalkyl;
each $R^7$ is independently selected from H, alkyl, haloalkyl, arylalkyl, and heteroalkyl;
r is 1, 2, 3, 4, 5, 6, 7, 8, 9, or 10; and
s is 1, 2, 3, 4, or 5.

Disclosed herein is a method of producing an LC of Formula (I), the method comprising reacting the cysteine residue of TA with $A^3$-$P^1$-L, wherein $A^3$ is a reactive precursor to form $A^1$. The method of producing an LC of Formula (I), may comprise reacting the cysteine residue of TA with $A^3$-$P^1$-L, wherein $A^3$ is haloacetamide, maleimide, benzyl halide, or pyridyl disulfide. $A^3$ may be a haloacetamide. $A^3$ may be a bromoacetamide.

The pharmaceutical compositions disclosed herein may further comprise one or more pharmaceutically acceptable salts, excipients or vehicles.

The methods and compositions disclosed herein may be used to treat a disease or condition in a subject in need thereof. The disease or condition may be a cardiovascular disorder. The disease or condition may be acute heart failure. The disease or condition may be fibrosis. The disease or condition may be pain. The pain may be neuropathic pain or inflammatory pain.

The LCs disclosed herein may be administered with one or more additional therapeutic agents. The one or more additional therapeutic agents may be selected from a group consisting of an anti-inflammatory drug, a statin, a diuretic, a beta-blocker, an angiotensin converting enzyme inhibitor, an angiotensin II receptor blocker or any combination thereof. The one or more additional therapeutic agents may be aspirin.

BRIEF DESCRIPTION OF THE DRAWINGS

The novel features of the invention are set forth with particularity in the appended claims. The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 shows a scheme for a chemical conjugation of pegylated lipid derivative to the L-cysteine modified relaxin, (boxed residues may be mutated to L-cysteine).

FIG. 2 shows relaxin modified with cysteine for lipid conjugation, (boxed residues may be mutated, for example to L-cysteine, lysine, glutamine, alanine).

FIG. 3 shows human relaxin 2 activating relaxin 2 receptor (RXFP2 or LGR7) in HEK293T cells expressing LGR7 and CRE-Luc reporter line.

FIG. 4 discloses "GGGRGG" as SEQ ID NO: 69.

FIG. 10. shows (a) the disulfide bond pattern for the Toxin-550 peptide (wild-type), and (b) an exemplary in vitro folding pathway of cysteine-knot Toxin-550 peptide, the middle structure depicting a two-sulfide bond intermediate, in which a disulfide bond is formed between cysteine I and cysteine IV and between cysteine II and cysteine V.

FIG. 11 shows mouse pharmacokinetic data for a lipid conjugate.

FIG. 16A-B show exemplary mTAs. Entries 1-10 depict exemplary mTAs comprising a relaxin A-chain and B-chain attached to a half-life extending moiety (represented by X). Entries 11-13 depict exemplary mTAs comprising toxin-550 attached to a half-life extending moiety (represented by X). X may be $FA_1$, $FA_2$, $FA_3$, $FA_4$, $FA_5$, $FA_6$, or $FA_Q$, or another lipid described herein. Disulfide bonds are depicted by brackets connecting two cysteine residues or by lines connecting two cysteine residues. FIG. 16B discloses "GSCGG" and "GSGG" as SEQ ID NOS 72 and 71, respectively.

DETAILED DESCRIPTION OF THE INVENTION

Figure 4:
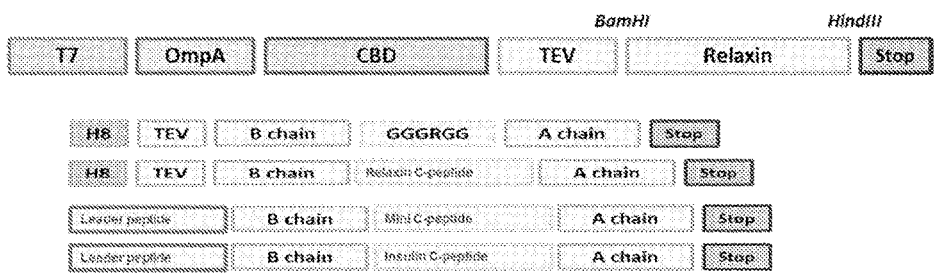
FIG. 4. shows a schematic of a pVB008 relaxin2 linker vector and additional schematics of other relaxin expression constructs.

Disclosed herein are modified therapeutic agents (mTAs). Generally, the mTAs may comprise a therapeutic agent (TA) and one or more half-life extending moieties, wherein the TA is attached to the one or more half-life extending moieties. The therapeutic agent may be a peptide. The TA may be covalently attached to each of the one or more half-life extending moieties. The TA may be attached to the one or more half-life extending moities via a cysteine residue on the therapeutic agent. The half-life of the modified therapeutic agent may be longer than the half-life of the therapeutic agent alone. A half-life extending moiety may comprise a lipid, a polyglycol region, or a combination thereof. A half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. A half-life extending moiety may be attached to the sulfur atom of a cysteine residue on the therapeutic agent. Non-limiting examples of mTAs include lipid conjugates (LCs) and XTEN-modified therapeutic agents (XTEN-mTAs).

Disclosed herein are lipid conjugates (LCs). Generally, the LCs comprise a lipid and a therapeutic agent. The lipid conjugates (LCs) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof and (b) a therapeutic agent (TA), wherein the therapeutic agent is a peptide and the one or more lipids are conjugated to the therapeutic agent via an amino acid on the peptide.

The lipid conjugates (LCs) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein is a lipid conjugate (LC) comprising (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue.

Further disclosed herein is a lipid conjugate (LC) comprising one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. The LC may comprise one or more lipids attached to a therapeutic agent comprising a modified relaxin peptide, wherein the modified relaxin peptide comprises a wild-type relaxin polypeptide with one or more amino acid mutations.

Disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the therapeutic agent is a peptide and the one or more lipids are conjugated to the therapeutic agent via an amino acid on the peptide.

Further disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein are pharmaceutical compositions comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue.

Further disclosed herein are pharmaceutical compositions comprising an LC, wherein the LC comprises one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. The pharmaceutical composition may comprise an LC, wherein the LC comprises one or more lipids attached to a therapeutic agent (TA), wherein the TA comprises a modified relaxin peptide, and wherein the modified relaxin peptide comprises a wild-type relaxin polypeptide with one or more amino acid mutations.

Disclosed herein is a method for treating a disease or condition in a subject in need thereof, the method comprising administering to the subject a composition comprising a an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the therapeutic agent is a peptide and the one or more lipids are conjugated to the therapeutic agent via an amino acid on the peptide.

Further disclosed herein is a method for treating a disease or condition in a subject in need thereof, the method comprising administering to the subject a composition comprising a an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein are methods of treating a disease or condition in a subject in need thereof, the method comprising administering to the subject a composition comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue.

Further disclosed herein are methods of treating a disease or condition in a subject in need thereof, the method comprising administering to the subject a composition comprising an LC, wherein the LC comprises one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. The method of treating a disease or condition in a subject in need thereof may comprise administering to the subject a composition comprising an LC, wherein the LC comprises one or more lipids attached to a therapeutic agent (TA), wherein the TA comprises a modified relaxin peptide, and wherein the modified relaxin peptide comprises a wild-type relaxin polypeptide with one or more amino acid mutations.

Disclosed herein are kits comprising an LC, wherein the LC comprises (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the therapeutic agent is a peptide and the one or more lipids are conjugated to the therapeutic agent via an amino acid on the peptide.

Further disclosed herein are kits comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

Further disclosed herein are kits comprising an LC, wherein the LC comprises (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue.

Further disclosed herein are kits comprising an LC, wherein the LC comprises one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. The kit may comprise an LC, wherein the LC comprises one or more lipids attached a therapeutic agent (TA), wherein the TA comprises a modified relaxin peptide, and wherein the modified relaxin peptide comprises a wild-type relaxin polypeptide with one or more amino acid mutations.

Further disclosed herein are LCs having the structure:

TA-$A^1$-$P^1$-L     Formula (I)

wherein: TA is the therapeutic agent; $A^1$ is a chemical group linking TA and $P^1$ or L; $P^1$ is a bond or comprises polyglycol; and L is the lipid.

Further disclosed herein are LCs having the structure:

TA-$A^1$-$P^1$-L     Formula (Ia)

wherein: TA is the therapeutic agent with a cysteine residue, wherein the cysteine residue is connected to $A^1$; $A^1$ is a chemical group linking TA and $P^1$; $P^1$ is a bond or -PEG-$A^2$-;

PEG is a chemical group comprising one or more polyethyleneglycol subunits; $A^2$ is a chemical group linking PEG and L; and L is the lipid.

Disclosed herein are compounds having the structure of $A^3$-$P^1$-L, wherein: $A^3$ may be a haloacetamide, maleimide, benzyl halide, or pyridyl disulfide; $P^1$ may be a bond or -PEG-$A^2$-; $A^2$ may be a chemical group linking PEG and L; L may be a lipid selected from sterols, sterol derivatives, bile acids, vitamin E derivatives, fatty di-acids, fatty acids, fatty amides, and fatty alcohols; and PEG may be selected from:

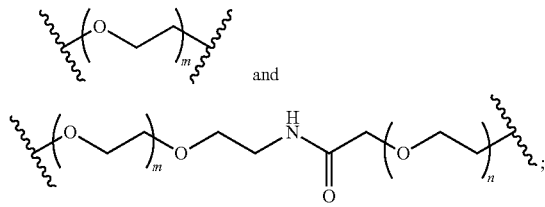

wherein
m and n may be independently 1, 2, 3, 4, 5, 6, 7, 8, 9, 10, 11, 12, 13, 14, 15, 16, 17, 18, 19, or 20.

Disclosed herein is a method of producing an LC of Formula (Ia), the method comprising reacting the cysteine residue of TA with $A^3$-$P^1$-L, wherein $A^3$ is a reactive precursor to form $A^1$. The method of producing an LC of Formula (Ia) may comprise reacting the cysteine residue of TA with $A^3$-$P^1$-L, wherein $A^3$ is haloacetamide, maleimide, benzyl halide, or pyridyl disulfide. $A^3$ may be a haloacetamide. $A^3$ may be a bromoacetamide.

Before the present methods, kits and compositions are described in greater detail, it is to be understood that this invention is not limited to particular method, kit or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for producing mTAs that extend the half-life of a therapeutic agent. These methods and compositions find therapeutic use in a number of diseases, for example, cardiovascular disease may be more effectively treated with a half-life extension molecule conjugated to relaxin than by relaxin alone. These and other objects, advantages, and features of the invention will become apparent to those persons skilled in the art upon reading the details of the compositions and methods as more fully described below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Modified Therapeutic Agent (mTA)

Disclosed herein are modified therapeutic agents (mTAs) may comprise a therapeutic agent (TA) and one or more half-life extending moieties, wherein the TA is attached to the one or more half-life extending moieties. The therapeutic agent may be a peptide. The TA may be covalently attached to each of the one or more half-life extending moieties. The TA may be attached to the one or more half-life extending moities via a cysteine residue on the therapeutic agent. The half-life of the modified therapeutic agent may be longer than the half-life of the therapeutic agent alone. A half-life extending moiety may comprise a lipid, a polyglycol region, or a combination thereof. A half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. A half-life extending moiety may be attached to the sulfur atom of a cysteine residue on the therapeutic agent. Non-limiting examples of mTAs include lipid conjugates (LCs) and XTEN-modified therapeutic agents (XTEN-mTAs).

Disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid; and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid; the peptide is selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid; the peptide is selected from relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, Toxin-550, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid; the peptide is relaxin or a derivative thereof, the derivative being a peptide comprising one or more amino acid additions, deletions, or substitutions, or a combination thereof and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid; the therapeutic agent is encoded by an amino acid sequence comprising at least a portion of a polypeptide sequence selected from a group consisting of SEQ ID NO: 10-56; and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid selected from sterols, sterol derivatives, bile acids, vitamin E derivatives, fatty di-acids, fatty acids, fatty amides, fatty amines, and fatty alcohols, and derivatives thereof and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide.

The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid selected from sterols, sterol derivatives, bile acids, vitamin E derivatives, fatty di-acids, fatty acids, fatty amides, fatty amines, and fatty alcohols, and derivatives thereof the peptide is selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid selected from sterols, sterol derivatives, bile acids, vitamin E derivatives, fatty di-acids, fatty acids, fatty amides, fatty amines, and fatty alcohols, and derivatives thereof; the peptide is selected from relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, Toxin-550, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid selected from sterols, sterol derivatives, bile acids, vitamin E derivatives, fatty di-acids, fatty acids, fatty amides, fatty amines, and fatty alcohols, and derivatives thereof; the peptide is relaxin or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region; and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region; the peptide is selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region; the peptide is selected from relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, Toxin-550, Moka, and VM-24, or a derivative thereof, the derivative being a peptide comprising one or more amino acid additions, deletions, or substitutions, or a combination thereof and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region; the peptide is relaxin or a derivative thereof, the derivative being a peptide comprising one or more amino acid additions, deletions, or substitutions, or a combination thereof and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region; the therapeutic agent is encoded by an amino acid sequence comprising at least a portion of a polypeptide sequence selected from a group consisting of SEQ ID NO: 10-56; and the half-life of the modified therapeutic agent is longer than the half-life of the peptide alone. The cysteine residue may be an amino acid addition or substitution on the peptide. The cysteine residue may be an amino acid addition or substitution on a wild-type peptide.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a lipid and a polyglycol region; and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region and a lipid selected from sterols, sterol derivatives, bile acids, vitamin E derivatives, fatty di-acids, fatty acids, fatty amides, fatty amines, and fatty alcohols, and derivatives thereof and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region and a lipid selected from sterols, sterol derivatives, bile acids, vitamin E derivatives, fatty di-acids, fatty acids, fatty amides, fatty amines, and fatty alcohols, and derivatives thereof the peptide is selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region and a lipid selected from sterols, sterol derivatives, bile acids, vitamin E derivatives, fatty di-acids, fatty acids, fatty amides, fatty amines, and fatty alcohols, and derivatives thereof the peptide is selected from relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, Toxin-550, Moka, and VM-24, or a derivative thereof, the derivative being a peptide comprising one or more amino acid additions, deletions, or substitutions, or a combination thereof and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises a polyglycol region and a lipid selected from sterols, sterol derivatives, bile acids, vitamin E derivatives, fatty di-acids, fatty acids, fatty amides, fatty amines, and fatty alcohols, and derivatives thereof the peptide is relaxin or a derivative thereof, the derivative being a peptide comprising one or more amino acid additions, deletions, or substitutions, or a combination thereof and the half-life of the modified therapeutic agent is longer than the half-life of the peptide alone. The cysteine residue may be an amino acid addition or substitution on the peptide. The mTA may be an LC.

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and the half-life of the modified therapeutic agent is longer than the half-life of the peptide alone. The peptide may comprise one or more amino acid additions, deletions, substitutions, or a combination thereof. The cysteine residue may be an amino acid addition or substitution on the peptide. The cysteine residue may be an amino acid addition or substitution on a wild-type peptide. The mTA may be an XTEN-modified therapeutic agent (XTEN-mTA).

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; the peptide is selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an XTEN-modified therapeutic agent (XTEN-mTA).

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; the peptide is selected from relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, Toxin-550, Moka, and VM-24, or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an XTEN-modified therapeutic agent (XTEN-mTA).

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; the peptide is relaxin or a derivative thereof, the derivative being a peptide comprising one or more amino acid additions, deletions, or substitutions, or a combination thereof; and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an XTEN-modified therapeutic agent (XTEN-mTA).

Further disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; each of the half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; the therapeutic agent is encoded by an amino acid sequence comprising at least a portion of a polypeptide sequence selected from a group consisting of SEQ ID NO: 10-56; and the half-life of the modified therapeutic agent is longer than the half-life of the peptide alone. The cysteine residue may be an amino acid addition or substitution on the peptide. The cysteine residue may be an amino acid addition or substitution on a wild-type peptide. The mTA may be an XTEN-modified therapeutic agent (XTEN-mTA).

The mTAs disclosed herein may have the structure:

$$TA\text{-}A^1\text{-}P^1\text{-}X \qquad \text{Formula (II)}$$

wherein:
 TA is the therapeutic agent;
 $A^1$ is a chemical group linking TA and $P^1$ or X;
 $P^1$ is a bond or comprises polyglycol; and
 X is a half-life extending moiety.
 X of Formula (II) may comprise a lipid.
 X of formula (II) may comprise an extended recombinant polypeptide (XTEN).
 The $P^1$ of an mTA of Formula (II) may be a bond.
 A sulfur or nitrogen atom of an amino acid residue of TA may be connected to $A^1$ via a chemical bond in an mTA of Formula (II). The $A^1$ of an mTA of Formula (II) may be selected from

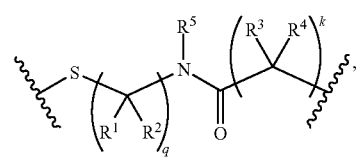

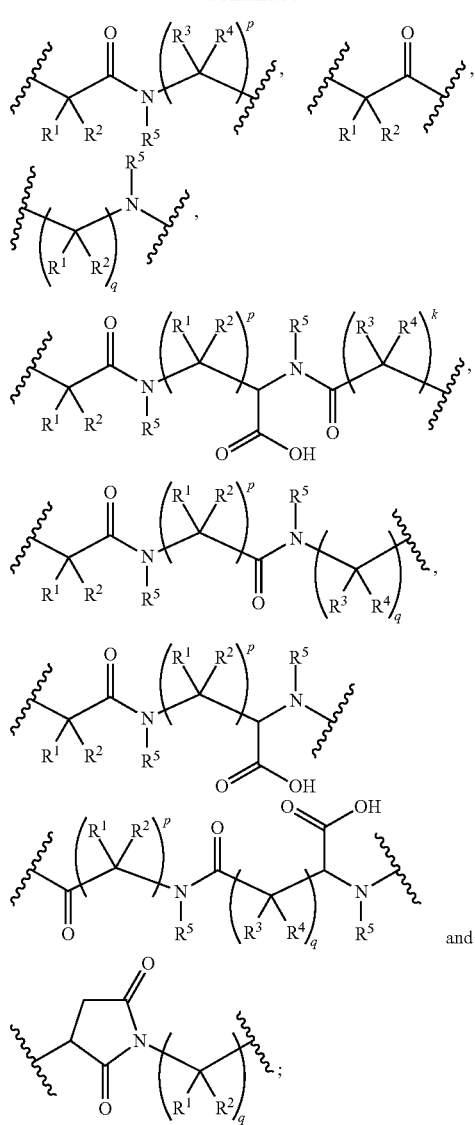

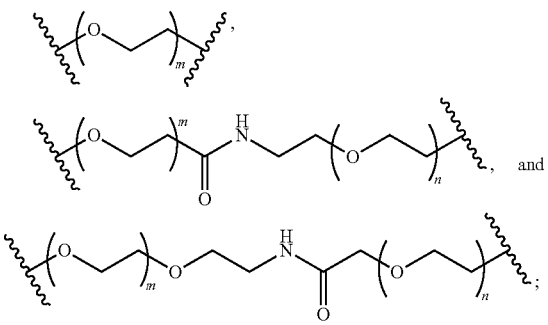

wherein m and n are independently 1, 2, 3, 4, 5, 6, 7, 8, 9, 10, 11, 12, 13, 14, 15, 16, 17, 18, 19, or 20. $A^2$ may be selected from a bond,

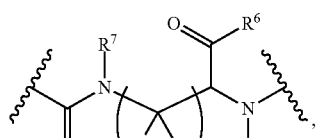

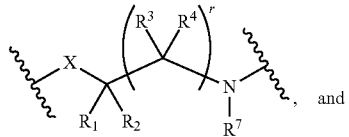

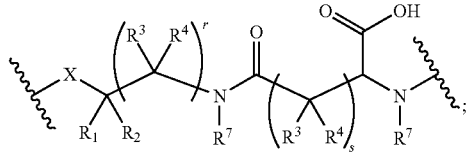

wherein X is a bond, $NR^5$, S, or O;
  each $R^1$, $R^2$, $R^3$, and $R^4$ is independently selected from H, halo, CN, —$SR^5$, alkyl, cycloalkyl, haloalkyl, —$NR^5R^5$, and —$OR^5$;
  each $R^5$ is independently H, alkyl, haloalkyl, arylalkyl, or heteroalkyl; $R^6$ is OH or —$NR^5R^5$;
  each $R^7$ is independently selected from H, alkyl, haloalkyl, arylalkyl, and heteroalkyl;
  r is 1, 2, 3, 4, 5, 6, 7, 8, 9, or 10; and
  s is 1, 2, 3, 4, or 5.

The half-life extending moiety of Formula (II) may comprise a lipid. The lipid may be selected from a group consisting of propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, myristic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid and hexatriacontanoic acid. The lipid may be selected from a group consisting of malonic acid, succinic acid, glutaric acid, adipic acid, pimelic acid, suberic acid, azelaic acid, sebacic acid, undecanedioic acid, dodecanedioic acid, tridecanedioic acid, tetradecanedioic acid, pentadecanedioic and
  each $R^1$, $R^2$, $R^3$, and $R^4$ is independently selected from H, halo, CN, —$SR^5$, alkyl, cycloalkyl, haloalkyl, —$NR^5R^5$, —$NC(O)R^5$, —$NC(O)OR^5$, and —$OR^5$;
  each $R^5$ is independently H, alkyl, haloalkyl, arylalkyl, (cycloalkyl)alkyl, or heteroalkyl;
  k is 1, 2, 3, 4, 5, 6, 7, 8, 9, or 10;
  p is 2, 3, 4, 5, 6, 7, 8, 9, or 10; and
  q is 2, 3, 4, 5, 6, 7, 8, 9, or 10.

The $P^1$ of an mTA of Formula (II) may comprise polyglycol. The polyglycol may be selected from polyethylene glycol, polypropylene glycol, polybutylene glycol, or a combination thereof. The polyglycol may be polyethylene glycol. The polyglycol may be polypropylene glycol. The polyglycol may be polybutylene glycol.

The $P^1$ of an mTA of Formula (II) may be -PEG-$A^2$-; wherein PEG is a chemical group comprising one or more polyethyleneglycol subunits; and $A^2$ is a chemical group linking PEG and X. PEG may be selected from acid, hexadecanedioic acid, heptadecanedioic acid, octadecanedioic acid, and nonadecanedioic acid. The lipid may be selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosapentanoic acid, erucic acid, docosahexaenoic acid. The lipid may be selected from a group consisting of cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, and glycochenodeoxycholic acid. The one or more lipids of an mTA of Formula (II) may be selected from a group consisting of cholic acid, chenodeoxycholic acid, lithocholic acid, deoxycholic acid, glycocholic acid, glycodeoxycholic acid, glycolithocholic acid, and glycochenodeoxycholic acid. The one or more lipids of an mTA of Formula (II) may be selected from a group consisting of α-tocopherol, β-tocopherol, γ-tocopherol, δ-tocopherol, α-tocotrienol, β-tocotrienol, γ-tocotrienol and δ-tocotrienol. The one or more lipids of an mTA of Formula (II) may be selected from a group consisting of octadecanedioic acid, tetradecylamine, myristic acid, docosahexaenoic acid, lithocholic acid ester, cholic acid and palmitic acid.

The mTAs disclosed herein may have the structure:

TA-A¹-P¹-X     Formula (IIa)

wherein:

TA is the therapeutic agent with a cysteine residue, wherein the cysteine residue is connected to $A^1$;

$A^1$ is a chemical group linking TA and $P^1$;

$P^1$ is a bond or -PEG-$A^2$-;

PEG is a chemical group comprising one or more polyethyleneglycol subunits;

$A^2$ is a chemical group linking PEG and X; and

X is a half-life extending moiety.

X of Formula IIa) may comprise a lipid.

X of formula IIa) may comprise an extended recombinant polypeptide (XTEN).

The sulfur atom of the cysteine residue of the TA of an mTA of Formula IIa) may be connected to $A^1$ via a chemical bond.

The PEG of an mTA of Formula IIa) may be selected from:

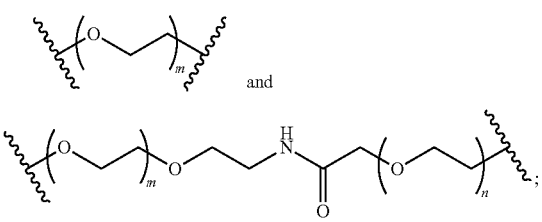

wherein m and n are independently 1, 2, 3, 4, 5, 6, 7, 8, 9, 10, 11, 12, 13, 14, 15, 16, 17, 18, 19, or 20.

In some embodiments of an mTA of Formula IIa) disclosed herein, $A^1$ is selected from and

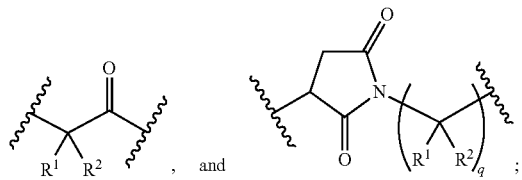

$R^1$, $R^2$, $R^3$, and $R^4$ are independently selected from H, halo, CN, —$SR^5$, alkyl, cycloalkyl, haloalkyl, —$NR^5R^5$, and —$OR^5$;

$R^5$ is H, alkyl, haloalkyl, arylalkyl, or heteroalkyl;

p is 2, 3, 4, 5, 6, 7, 8, 9, or 10; and q is 2, 3, 4, 5, 6, 7, 8, 9, or 10.

In some embodiments described of an mTA of Formula IIa) disclosed herein, $A^2$ is selected from a bond,

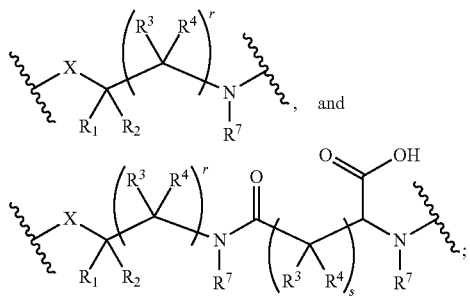

X is a bond, $NR^5$, or O;

$R^1$, $R^2$, $R^3$, and $R^4$ are independently selected from H, halo, CN, —$SR^5$, alkyl, cycloalkyl, haloalkyl, —$NR^5R^5$, and —$OR^5$;

$R^5$ is H, alkyl, haloalkyl, arylalkyl, or heteroalkyl;

each $R^7$ is independently selected from H, alkyl, haloalkyl, arylalkyl, and heteroalkyl;

r is 1, 2, 3, 4, 5, 6, 7, 8, 9, or 10; and s is 1, 2, 3, 4, or 5.

In some embodiments of an mTA of Formula IIa) disclosed herein, $P^1$ is -PEG-$A^2$.

Disclosed herein are methods of producing an mTA of Formula (II), the method comprising reacting the cysteine residue of TA with $A^3$-$P^1$-X, wherein $A^3$ is a reactive precursor to form $A^1$. In some embodiments, $A^3$ is a haloacetamide, maleimide, benzyl halide, or pyridyl disulfide. In further embodiments, $A^3$ is a haloacetamide. In still further embodiments, $A^3$ is a bromoacetamide.

The modified therapeutic agents (mTAs) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

The modified therapeutic agents (mTAs) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof, and (b) a therapeutic agent (TA), wherein the TA is a peptide and the one or more lipids are conjugated to the TA via an amino acid residue on the peptide. The amino acid residue may be a cysteine, lysine, or serine. The amino acid residue may be selected from cysteine or lysine. The amino acid residue may be cysteine. The amino acid residue may be lysine. The amino acid may be an amino acid mutation. The amino acid may be an amino acid addition or an amino acid substitution.

The modified therapeutic agents (mTA) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof. The modified therapeutic agents (mTA) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA comprises a relaxin peptide or derivative thereof.

The modified therapeutic agents (mTA) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue. The modified therapeutic agents (mTA) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof, and (b) a therapeutic agent (TA), wherein the TA comprises a relaxin peptide or derivative thereof, wherein the one or more lipids are attached to the therapeutic agent via an amino acid residue on the peptide. The amino acid residue may be a cysteine, lysine, or serine. The amino acid residue may be selected from cysteine or lysine. The amino acid residue may be cysteine. The amino acid residue may be lysine. The amino acid may be an amino acid mutation. The amino acid may be an amino acid addition or an amino acid substitution. The amino acid residue may be an amino acid addition or substitution on a wild-type peptide.

The modified therapeutic agents (mTA) may comprise one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. The modified therapeutic agents (mTA) may comprise one or more lipids attached to a therapeutic agent (TA), wherein the TA comprises a modified relaxin peptide, and wherein the modified relaxin peptide comprises a wild-type relaxin polypeptide with one or more amino acid mutations.

The mTAs disclosed herein may comprise a TA comprising a modified relaxin peptide. The mTAs disclosed herein may comprise one or more lipids, wherein the one or more lipids may be selected from a group consisting of sterols, sterol derivatives, bile acids, vitamin E derivatives, fatty acids and fatty alcohols, and derivatives thereof. The attachment of the one or more lipids to the modified relaxin peptide may comprise covalent attachment. The one or more lipids may be attached to the modified relaxin peptide via a cysteine residue. The cysteine residue may be an amino acid mutation. The cysteine residue may be an amino acid addition or an amino acid substitution. The cysteine residue may be an amino acid addition or substitution on a wild-type peptide.

Half-Life Extending Moieties

Disclosed herein are modified therapeutic agents (mTAs) comprising a therapeutic agent and one or more half-life extending moieties, wherein the therapeutic agent is a peptide that is covalently attached to each of the one or more half-life extending moieties via a cysteine residue on the peptide; and the half-life of the modified therapeutic agent is longer than the half-life of the peptide alone.

The one or more half-life extending moieties may comprise a lipid, a polyglycol region, or a combination thereof. The one or more half-life extending moieties may comprise an extended recombinant polypeptide (XTEN).

The polyglycol region may comprise one or more polyethylene glycol units, polypropylene glycol units, or polybutylene glycol units, or a combination thereof. The polyglycol region may comprise one or more polyethylene glycol units. The polyglycol region may comprise one or more polypropylene glycol units. The polyglycol region may comprise one or more polybutylene glycol units.

The polyglycol region may comprise 10, 20, 30, 40, 50, 60, 70, 80, 90, 100, or more polyethylene glycol units, polypropylene glycol units, or polybutylene glycol units, or a combination thereof. The polyglycol region may comprise 10, 20, 30, 40, 50, 60, 70, 80, 90, 100, or more polyethylene glycol units. The polyglycol region may comprise 10, 20, 30, 40, 50, 60, 70, 80, 90, 100, or more polypropylene glycol units. The polyglycol region may comprise 10, 20, 30, 40, 50, 60, 70, 80, 90, 100, or more polybutylene glycol units.

The polyglycol region may comprise 100, 200, 300, 400, 500, 600, 700, 800, 900, 1000, or more polyethylene glycol units, polypropylene glycol units, or polybutylene glycol units, or a combination thereof. The polyglycol region may comprise 100, 200, 300, 400, 500, 600, 700, 800, 900, 1000, or more polyethylene glycol units. The polyglycol region may comprise 100, 200, 300, 400, 500, 600, 700, 800, 900, 1000, or more polypropylene glycol units. The polyglycol region may comprise 100, 200, 300, 400, 500, 600, 700, 800, 900, 1000, or more polybutylene glycol units.

The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polyethylene glycol units, polypropylene glycol units, or polybutylene glycol units, or a combination thereof. The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polyethylene glycol units. The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polypropylene glycol units. The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polybutylene glycol units.

The polyglycol region may comprise a molecular weight of 500-50,000 daltons. The polyglycol region may comprise a molecular weight of 500-40,000 daltons. The polyglycol region may comprise a molecular weight of 500-30,000 daltons. The polyglycol region may comprise a molecular weight of 500-20,000 daltons. The polyglycol region may comprise a molecular weight of 500, 600, 700, 800, 900, 1000, 2000, 3000, 4000, 5000, 6000, 7000, 8000, 9000, 10000, 15000, 20000, 25000, 30000, 35000, 40000, or 45000 daltons or more, including increments therein.

The half-life extending moieties may be attached to the TA via a cysteine residue on the TA. The attachment may be via chemical attachment through the sulfur atom of a cysteine residue on the TA. The half-life extending moieties may comprise a linker which is directly attached to the sulfur atom of a cysteine residue on the TA. The half-life extending moieties may comprise a linker which is covalently attached to the sulfur atom of a cysteine residue on the TA.

Lipid Conjugate (LC)

Disclosed herein are lipid conjugates (LCs) comprising one or more lipids attached to one or more therapeutic agents (TAs). The lipid conjugate may comprise one or more lipids attached to one TA. The lipid conjugate may further comprise a hydrophilic connector between the one or more TAs and the one or more lipids. The lipid conjugate may further comprise one or more polyethyleneglycol subunits. The one or more lipids may be pegylated.

The LCs disclosed herein may have the structure:

TA-A$^1$P$^1$L     Formula (I)

wherein:

TA is the therapeutic agent;

A$^1$ is a chemical group linking TA and P$^1$ or L;

P$^1$ is a bond or comprises polyglycol; and

L is the lipid.

The P$^1$ of an LC of Formula (I) may be a bond.

A sulfur or nitrogen atom of an amino acid residue of TA may be connected to A$^1$ via a chemical bond in an LC of Formula (I). The A$^1$ of an LC of Formula (I) may be selected from

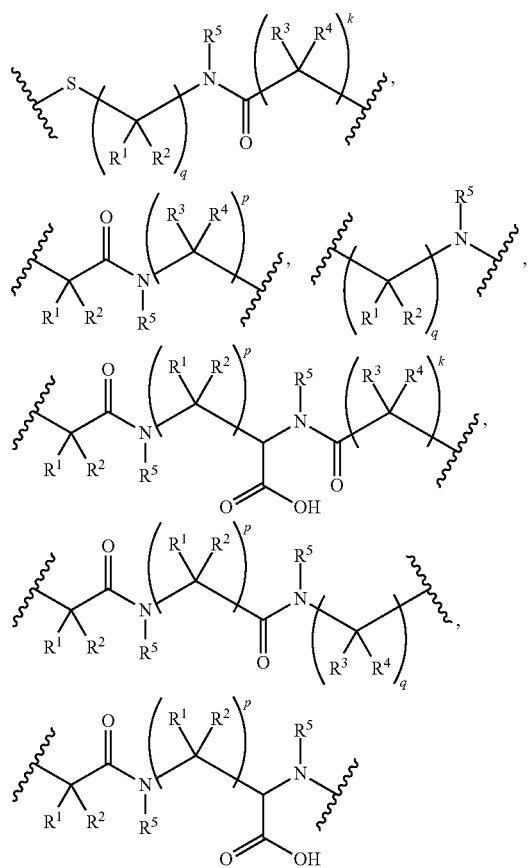

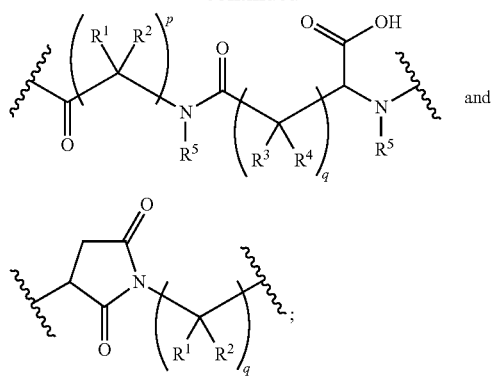

and each R$^1$, R$^2$, R$^3$, and R$^4$ is independently selected from H, halo, CN, —SR$^5$, alkyl, cycloalkyl, haloalkyl, —NR$^5$R$^5$, —NC(O)R$^5$, —NC(O)OR$^5$, and —OR$^5$;

each R$^5$ is independently H, alkyl, haloalkyl, arylalkyl, (cycloalkyl)alkyl, or heteroalkyl;

k is 1, 2, 3, 4, 5, 6, 7, 8, 9, or 10;

p is 2, 3, 4, 5, 6, 7, 8, 9, or 10; and q is 2, 3, 4, 5, 6, 7, 8, 9, or 10.

The P$^1$ of an LC of Formula (I) may comprise polyglycol. The polyglycol may be selected from polyethylene glycol, polypropylene glycol, polybutylene glycol, or a combination thereof. The polyglycol may be polyethylene glycol. The polyglycol may be polypropylene glycol. The polyglycol may be polybutylene glycol.

The P$^1$ of an LC of Formula (I) may be -PEG-A$^2$-; wherein PEG is a chemical group comprising one or more polyethyleneglycol subunits; and A$^2$ is a chemical group linking PEG

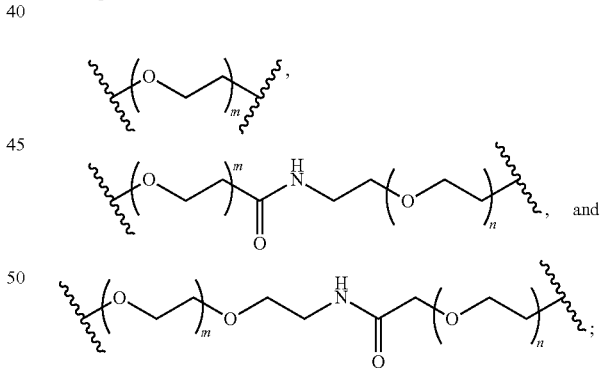

and L. PEG may be selected from wherein m and n are independently 1, 2, 3, 4, 5, 6, 7, 8, 9, 10, 11, 12, 13, 14, 15, 16, 17, 18, 19, or 20. A$^2$ may be selected from a bond,

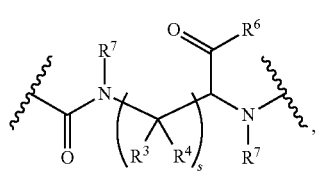

-continued

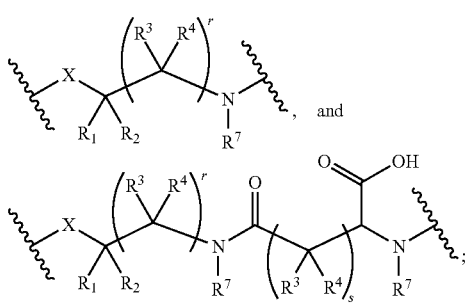

wherein X is a bond, $NR^5$, S, or O;
each $R^1$, $R^2$, $R^3$, and $R^4$ is independently selected from H, halo, CN, $-SR^5$, alkyl, cycloalkyl, haloalkyl, $-NR^5R^5$, and $-OR^5$;
each $R^5$ is independently H, alkyl, haloalkyl, arylalkyl, or heteroalkyl; $R^6$ is OH or $-NR^5R^5$;
each $R^7$ is independently selected from H, alkyl, haloalkyl, arylalkyl, and heteroalkyl;
r is 1, 2, 3, 4, 5, 6, 7, 8, 9, or 10; and
s is 1, 2, 3, 4, or 5.

The one or more lipids of an LC of Formula (I) may be selected from a group consisting of propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, myristic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid and hexatriacontanoic acid. The one or more lipids of an LC of Formula (I) may be selected from a group consisting of malonic acid, succinic acid, glutaric acid, adipic acid, pimelic acid, suberic acid, azelaic acid, sebacic acid, undecanedioic acid, dodecanedioic acid, tridecanedioic acid, tetradecanedioic acid, pentadecanedioic acid, hexadecanedioic acid, heptadecanedioic acid, octadecanedioic acid, and nonadecanedioic acid. The one or more lipids of an LC of Formula (I) may be selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosapentanoic acid, erucic acid, docosahexaenoic acid. The one or more lipids of an LC of Formula (I) may be selected from a group consisting of cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, and glycochenodeoxycholic acid. The one or more lipids of an LC of Formula (I) may be selected from a group consisting of cholic acid, chenodeoxycholic acid, lithocholic acid, deoxycholic acid, glycocholic acid, glycodeoxycholic acid, glycolithocholic acid, and glycochenodeoxycholic acid. The one or more lipids of an LC of Formula (I) may be selected from a group consisting of α-tocopherol, β-tocopherol, γ-tocopherol, δ-tocopherol, α-tocotrienol, β-tocotrienol, γ-tocotrienol and δ-tocotrienol. The one or more lipids of an LC of Formula (I) may be selected from a group consisting of octanedioic acid, tetradecylamine, myristic acid, docosahexaenoic acid, lithocholic acid ester, cholic acid and palmitic acid.

The LCs disclosed herein may have the structure:

$$TA-A^1P^1L \quad \text{Formula (Ia)}$$

wherein:
TA is the therapeutic agent with a cysteine residue, wherein the cysteine residue is connected to $A^1$;
$A^1$ is a chemical group linking TA and $P^1$;
$P^1$ is a bond or $-PEG-A^2-$;
PEG is a chemical group comprising one or more polyethyleneglycol subunits;
$A^2$ is a chemical group linking PEG and L; and
L is the lipid.

The sulfur atom of the cysteine residue of the TA of an LC of Formula (Ia) may be connected to $A^1$ via a chemical bond.
The PEG of an LC of Formula (Ia) may be selected from:

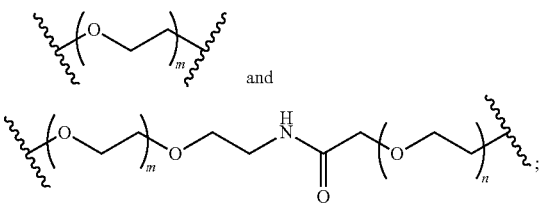

wherein
m and n are independently 1, 2, 3, 4, 5, 6, 7, 8, 9, 10, 11, 12, 13, 14, 15, 16, 17, 18, 19, or 20.

In some embodiments of an LC of Formula (Ia) disclosed herein,
$A^1$ is selected from

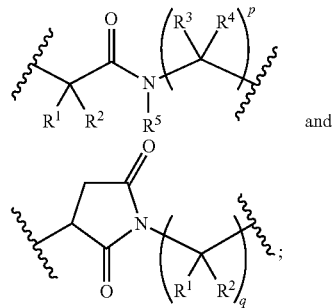

and
$R^1$, $R^2$, $R^3$, and $R^4$ are independently selected from H, halo, CN, $-SR^5$, alkyl, cycloalkyl, haloalkyl, $-NR^5R^5$, and $-OR^5$;
$R^5$ is H, alkyl, haloalkyl, arylalkyl, or heteroalkyl;
p is 2, 3, 4, 5, 6, 7, 8, 9, or 10; and
q is 2, 3, 4, 5, 6, 7, 8, 9, or 10.

In some embodiments described of an LC of Formula (Ia) disclosed herein,
$A^2$ is selected from a bond,

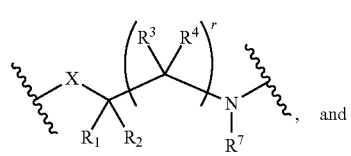

-continued

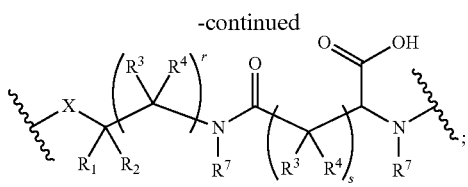

X is a bond, $NR^5$, or O;
$R^1$, $R^2$, $R^3$, and $R^4$ are independently selected from H, halo, CN, —$SR^5$, alkyl, cycloalkyl, haloalkyl, —$NR^5R^5$, and —$OR^5$;
$R^5$ is H, alkyl, haloalkyl, arylalkyl, or heteroalkyl;
each $R^7$ is independently selected from H, alkyl, haloalkyl, arylalkyl, and heteroalkyl;
r is 1, 2, 3, 4, 5, 6, 7, 8, 9, or 10; and
s is 1, 2, 3, 4, or 5.

In some embodiments of an LC of Formula (Ia) disclosed herein, $P^1$ is -PEG-$A^2$.

Disclosed herein are methods of producing an LC of Formula (I), the method comprising reacting the cysteine residue of TA with $A^3$-$P^1$-L, wherein $A^3$ is a reactive precursor to form $A^1$. In some embodiments, $A^3$ is a haloacetamide, maleimide, benzyl halide, or pyridyl disulfide. In further embodiments, $A^3$ is a haloacetamide. In still further embodiments, $A^3$ is a bromoacetamide.

The lipid conjugates (LCs) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more lipids are conjugated to the one or more therapeutic agents via a cysteine residue.

The lipid conjugates (LCs) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein the TA is a peptide and the one or more lipids are conjugated to the TA via an amino acid residue on the peptide. The amino acid residue may be a cysteine, lysine, or serine. The amino acid residue may be selected from cysteine or lysine. The amino acid residue may be cysteine. The amino acid residue may be lysine. The amino acid may be an amino acid mutation. The amino acid may be an amino acid addition or an amino acid substitution.

The lipid conjugates (LC) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof. The lipid conjugates (LC) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof and (b) a therapeutic agent (TA), wherein the TA comprises a relaxin peptide or derivative thereof.

The lipid conjugates (LC) may comprise (a) one or more lipids, the lipids selected from sterols, sterol derivatives, bile acids, vitamin E derivatives, fatty di-acids, fatty acids, fatty amides, and fatty alcohols; and (b) one or more therapeutic agents (TAs), wherein the one or more TAs comprise a relaxin peptide or derivative thereof, wherein the one or more lipids are attached to the one or more therapeutic agent via a cysteine residue. The lipid conjugates (LC) may comprise (a) one or more lipids, the lipids selected from sterols, sterol derivatives, bile acids, vitamin E derivatives, fatty di-acids, fatty acids, fatty amides, fatty amines, and fatty alcohols, and derivatives thereof and (b) a therapeutic agent (TA), wherein the TA comprises a relaxin peptide or derivative thereof, wherein the one or more lipids are attached to the therapeutic agent via an amino acid residue on the peptide. The amino acid residue may be a cysteine, lysine, or serine. The amino acid residue may be selected from cysteine or lysine. The amino acid residue may be cysteine. The amino acid residue may be lysine. The amino acid may be an amino acid mutation. The amino acid may be an amino acid addition or an amino acid substitution.

The lipid conjugates (LC) may comprise one or more lipids attached to one or more therapeutic agents (TAs), wherein the one or more TAs comprise a modified relaxin peptide, and wherein the modified relaxin peptide comprises a wild-type relaxin polypeptide with one or more amino acid mutations. The lipid conjugates (LC) may comprise one or more lipids attached to a therapeutic agent (TA), wherein the TA comprises a modified relaxin peptide, and wherein the modified relaxin peptide comprises a wild-type relaxin polypeptide with one or more amino acid mutations.

The LCs disclosed herein may comprise a TA comprising a modified relaxin peptide. The LCs disclosed herein may comprise one or more lipids, wherein the one or more lipids may be selected from a group consisting of sterols, sterol derivatives, bile acids, vitamin E derivatives, fatty acids and fatty alcohols, and derivatives thereof. The attachment of the one or more lipids to the modified relaxin peptide may comprise covalent attachment. The one or more lipids may be attached to the modified relaxin peptide via a cysteine residue. The cysteine residue may be an amino acid mutation. The cysteine residue may be an amino acid addition or an amino acid substitution. The cysteine residue may be an amino acid addition or substitution on a wild-type peptide.

Linker

The LCs disclosed herein may further comprise one or more linkers. The LCs disclosed herein may further comprise two or more linkers. The LCs disclosed herein may further comprise three or more linkers. The LCs disclosed herein may further comprise four or more linkers. LCs disclosed herein may further comprise five or more linkers.

The one or more linkers may enable attachment of a lipid to a therapeutic agent. The linker may enable attachment of a lipid to another lipid. The linker may enable attachment of a lipid to a chemical group comprising one or more polyethyleneglycol subunits. The linker may enable attachment of a PEG to another PEG. The linker may enable attachment of a PEG to a therapeutic agent. The linker may enable attachment of a therapeutic agent to another therapeutic agent. The linker may be an amino acid. The linker may be an amino acid of the therapeutic agent. The linker may be an amino acid mutation of the therapeutic agent. The linker may be a substituted amino acid of the therapeutic agent. The linker may be an amino acid addition of the therapeutic agent. The linker may be an amino acid mutation located at the C-terminus of the peptide. The linker may be an amino acid mutation located at the N-terminus of the peptide. The linker may be an amino acid mutation located at a non-terminus position of the peptide. The linker may be a lysine. The linker may be a cysteine. The linker may be an L-cysteine. The linker may be an ether or an amide. The linker may link a PEG molecule to a lipid.

Lipid Derivatives

The LCs disclosed herein may comprise one or more lipid derivatives. The lipid derivatives may be attached to a TA. Attachment of the lipid derivative to the TAs may enhance the pharmacokinetic properties of the TAs. Lipid derivatives may comprise polyglycol. Lipid derivatives may be pegylated. A pegylated lipid may comprise at least one polyethyleneglycol subunit. The lipid derivatives may be not pegylated. Lipids may be broadly defined as hydrophobic or amphiphilic small molecules. Lipids may be naturally occurring or synthetic. Lipids may be eicosanoids, prostaglandins, leukotrienes, thromboxanes, wax esters, coenzyme A derivatives, fatty acid carnitines, fatty acid amides, ethanolamines, bile acids, vitamin E, vitamin A, vitamin D, vitamin K, fat-soluble vitamin derivatives, monoglycerides, diglycerides, triglycerides, phospholipids, phosphatidylcholine, glycerolipids, glycerols, glycerophospholypids, sphingolipids, saccharolipids, polyketides, sterols, sterol derivatives, sterol lipids, steroid hormones, prenol lipids, carotenoids, fatty acids, and fatty alcohols.

In one aspect, disclosed herein are lipid derivatives having the structure of $A^3$-$P^1$-L, wherein:

$A^3$ is a haloacetamide, maleimide, benzyl halide, or pyridyl disulfide;

$P^1$ is a bond or -PEG-$A^2$-;

PEG is a chemical group comprising one or more polyethyleneglycol subunits;

$A^2$ is a chemical group linking PEG and L; and

L is a lipid selected from sterols, sterol derivatives, bile acids, vitamin E derivatives, fatty di-acids, fatty acids, fatty amides, and fatty alcohols, and derivatives thereof.

In some embodiments described herein, PEG is selected from:

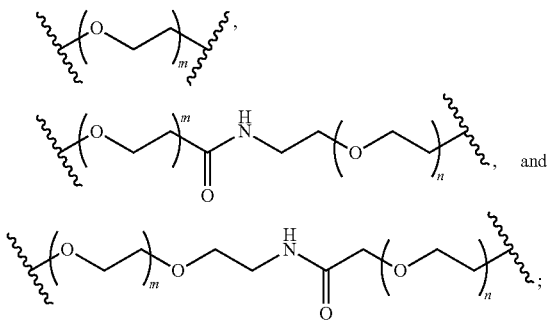

wherein m and n are independently 1, 2, 3, 4, 5, 6, 7, 8, 9, 10, 11, 12, 13, 14, 15, 16, 17, 18, 19, or 20.

In some embodiments described herein, $A^2$ is selected from a bond,

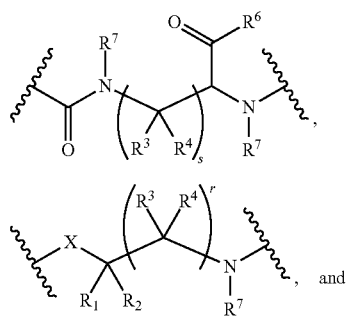

X is a bond, $NR^5$, S, or O;

each $R^1$, $R^2$, $R^3$, and $R^4$ is independently selected from H, halo, CN, —$SR^5$, alkyl, cycloalkyl, haloalkyl, —$NR^5R^5$, and —$OR^5$;

each $R^5$ is independently H, alkyl, haloalkyl, arylalkyl, or heteroalkyl; $R^6$ is OH or —$NR^5R^5$;

each $R^7$ is independently selected from H, alkyl, haloalkyl, arylalkyl, and heteroalkyl;

r is 1, 2, 3, 4, 5, 6, 7, 8, 9, or 10; and s is 1, 2, 3, 4, or 5.

Lipids

The LCs disclosed herein may comprise one or more lipids. The one or more lipids may be fatty acids. The fatty acids (FAs) may be attached to one or more therapeutic agents (TAs). Attachment of the fatty acids to the TAs may enhance the pharmacokinetic properties of the TAs. Fatty acids may be fatty di-acids, fatty amides, fatty amines, or fatty alcohols. Fatty acids may be saturated or unsaturated. Saturated fatty acids include, but are not limited to, lauric acid, myristic acid, palmitic acid, stearic acid, arachidic acid. Unsaturated fatty acids include, but are not limited to palmitoleic acid, oleic acid, linoleic acid, linolenic acid, erucic acid and arachidonic acid. Fatty acids may be short-chain fatty acids, medium chain fatty acids, long chain fatty acids or very long chain fatty acids. Fatty acids may be monounsaturated or polyunsaturated. Fatty acids may be omega fatty acids, essential fatty acids, partially hydrogenated fatty acids, cis-isomer fatty acids, or trans-isomer fatty acids. Fatty acids may be omega-3 fatty acids, omega-6 fatty acids or omega-9 fatty acids. Fatty acids may be dicarboxylic acids.

The fatty acid may comprise a chain of about 6, 7, 8, 9, 10, 11, 12, 13, 14, 15, 16, 17, 18, 19, 20, 21, 22, 23, 24, 25, 26 or more carbon atoms. The fatty acid may comprise a carbon chain further comprising 1, 2, 3, 4, 5, 6 or more double bonds. The fatty acid may be naturally occurring. The fatty acid may not be naturally occurring. The fatty acid may be synthesized.

The LCs disclosed herein may further comprise one or more fatty acids. The LCs disclosed herein may further comprise two or more fatty acids. The LCs disclosed herein may further comprise three or more fatty acids. The LCs disclosed herein may further comprise four or more fatty acids. LCs disclosed herein may further comprise five or more fatty acids. The fatty acids may be different. The fatty acids may be the same.

The one or more lipids of any LC may be selected from the group consisting of myristic acid, docosahexanoic acid, lithocholic acid ester, cholic acid and palmitic acid. The one or more lipids of any LC may be myristic acid. The one or more lipids of any LC may be docosahexanoic acid. The one or more lipids of any LC may be lithocholic acid ester. The one or more lipids of any LC may be cholic acid. The one or more lipids of any LC may be palmitic acid.

The LCs may comprise one or more sterols or sterol derivatives. The sterols or sterol derivatives may be selected from a group consisting of cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, and glycochenodeoxycholic acid.

The LCs may comprise one or more bile acids. The bile acids may be selected from a group consisting of cholic acid, chenodeoxycholic acid, lithocholic acid, deoxycholic acid, glycocholic acid, glycodeoxycholic acid, glycolithocholic acid, and glycochenodeoxycholic acid.

The LC may comprise one or more Vitamin E derivatives. The Vitamin E derivatives may be selected from a group consisting of α-tocopherol, β-tocopherol, γ-tocopherol, tocopherol, α-tocotrienol, β-tocotrienol, γ-tocotrienol and δ-tocotrienol.

Pegylated Lipid

The LCs disclosed herein in may comprise one or more pegylated lipids. A pegylated lipid may comprise at least one polyethyleneglycol subunit. The connection between the lipid and the one or more polyethyleneglycol subunits may be a direct bond or a linker ($A^2$). Non-limiting examples of a linker between the lipid and the one or more polyethyleneglycol subunits include: a bond,

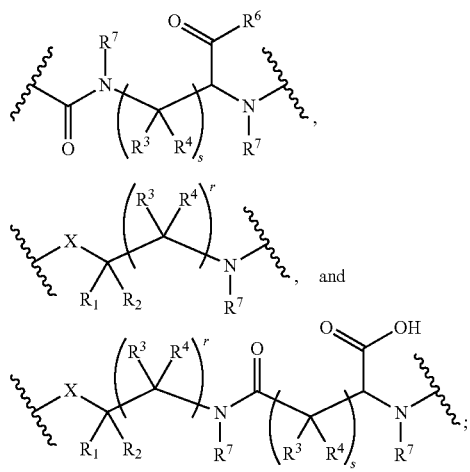

wherein
X is a bond, $NR^5$, S, or O;
each $R^1$, $R^2$, $R^3$, and $R^4$ is independently selected from H, halo, CN, —$SR^5$, alkyl, cycloalkyl, haloalkyl, —$NR^5R^5$, and —$OR^5$;
each $R^5$ is independently H, alkyl, haloalkyl, arylalkyl, or heteroalkyl;
$R^6$ is OH or —$NR^5R^5$;
each $R^7$ is independently selected from H, alkyl, haloalkyl, arylalkyl, and heteroalkyl;
r is 1, 2, 3, 4, 5, 6, 7, 8, 9, or 10; and
s is 1, 2, 3, 4, or 5.

A pegylated lipid may have the structure $P^1$-L, wherein $P^1$ is -PEG-$A^2$-; PEG is a chemical group comprising one or more polyethyleneglycol subunits; $A^2$ is a chemical group linking PEG and L; and L is a lipid. PEG may be selected from:

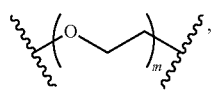

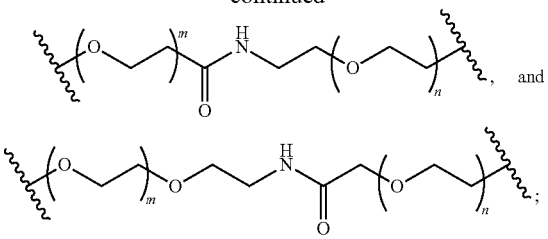

wherein
m and n are independently 1, 2, 3, 4, 5, 6, 7, 8, 9, 10, 11, 12, 13, 14, 15, 16, 17, 18, 19, or 20.

A pegylated lipid may be connected to a therapeutic agent through a linker. The linker may comprise one or more amide moieties.

XTEN-Modified Therapeutic Agent (XTEN-mTA)

Disclosed herein is an XTEN-modified therapeutic agent (XTEN-mTA) comprising (a) an extended recombinant polypeptide (XTEN); and (b) a therapeutic agent (TA) selected from a group consisting of relaxin, fibroblast growth factor 21 (FGF21), leptin, Toxin-550, and analogs thereof.

Further disclosed herein is an XTEN-modified therapeutic agent (XTEN-mTA) comprising (a) an extended recombinant polypeptide (XTEN); and (b) a therapeutic agent (TA) comprising relaxin or analog thereof.

Further disclosed herein is an XTEN-modified therapeutic agent (XTEN-mTA) comprising (a) an extended recombinant polypeptide (XTEN); and (b) a therapeutic agent (TA) comprising FGF21 or analog thereof.

Further disclosed herein is an XTEN-modified therapeutic agent (XTEN-mTA) comprising (a) an extended recombinant polypeptide (XTEN); and (b) a therapeutic agent (TA) comprising leptin or analog thereof.

Further disclosed herein is an XTEN-modified therapeutic agent (XTEN-mTA) comprising (a) an extended recombinant polypeptide (XTEN); and (b) a therapeutic agent (TA) comprising Toxin-550 or analog thereof.

Further disclosed herein is an XTEN-modified therapeutic agent (XTEN-mTA) comprising (a) a therapeutic agent (TA) selected from a group consisting of relaxin, fibroblast growth factor 21 (FGF21), leptin, Toxin-550, and analogs thereof; and (b) an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets, wherein the TA is attached to the XTEN. Attachment of the TA to the XTEN may be via a cysteine residue on the TA. Attachment of the TA to the XTEN may be through the sulfur atom of a cysteine residue on the TA.

Further disclosed herein is an XTEN-modified therapeutic agent (XTEN-mTA) comprising (a) a therapeutic agent (TA) comprising relaxin or an analog thereof; and an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets, wherein the TA is attached to the XTEN. Attachment of the TA to the XTEN may be via a cysteine residue on the TA. Attachment of the TA to the XTEN may be through the sulfur atom of a cysteine residue on the TA.

Further disclosed herein is an XTEN-modified therapeutic agent (XTEN-mTA) comprising (a) a therapeutic agent (TA) comprising FGF21 or an analog thereof; and an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets, wherein the TA is attached to the XTEN. Attachment of the TA to the XTEN may be via a cysteine residue on the TA. Attachment of the TA to the XTEN may be through the sulfur atom of a cysteine residue on the TA.

Further disclosed herein is an XTEN-modified therapeutic agent (XTEN-mTA) comprising (a) a therapeutic agent (TA) comprising leptin or an analog thereof; and an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets, wherein the TA is attached to the XTEN. Attachment of the TA to the XTEN may be via a cysteine residue on the TA. Attachment of the TA to the XTEN may be through the sulfur atom of a cysteine residue on the TA.

Further disclosed herein is an XTEN-modified therapeutic agent (XTEN-mTA) comprising (a) a therapeutic agent (TA) comprising Toxin-550 or an analog thereof; and an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets, wherein the TA is attached to the XTEN. Attachment of the TA to the XTEN may be via a cysteine residue on the TA. Attachment of the TA to the XTEN may be through the sulfur atom of a cysteine residue on the TA.

The XTEN-mTA may comprise less than about 2000, 1800, 1600, 1500, 1400, 1300, 1200, 1100, 1000 amino acids in length. The XTEN-mTA may comprise less than about 975, 950, 925, 875, 850, 825, 800, 775, 750, 725, 700, 675, 650, 625, or 600 amino acids in length. The XTEN-mTA may comprise less than about 900 amino acids in length. The XTEN-mTA may comprise less than about 890 amino acids in length. The XTEN-mTA may comprise less than about 880 amino acids in length. The XTEN-mTA may comprise less than about 870 amino acids in length. The XTEN-mTA may comprise less than about 860 amino acids in length. The XTEN-mTA may comprise less than about 850 amino acids in length.

The amino sequence of the XTEN-mTA may comprise one or more aspartate residues. The amino sequence of the XTEN-mTA may comprise 2, 3, 4, 5, 6, 7, 8, 9, 10, 11, 12, 13, 14, 15, 16, 17, 18, 19, 20 or more aspartate residues. The amino sequence of the XTEN-mTA may comprise 2 or more aspartate residues. The amino sequence of the XTEN-mTA may comprise 3 or more aspartate residues. The amino sequence of the XTEN-mTA may comprise 4 or more aspartate residues.

The XTEN-mTA may comprise one or more XTENs. The XTEN-mTA may comprise 2, 3, 4, 5, 6, 7, 8, 9, 10, 11, 12, 13, 14, 15, 16, 17, 18, 19, 20 or more XTENs. The XTEN-mTA may comprise 2 or more XTENs. The XTEN-mTA may comprise 3 or more XTENs. The XTEN-mTA may comprise 4 or more XTENs.

The XTEN may comprise an amino acid sequence comprising 10 or more amino acids based on or derived from the amino acid sequence selected from a group consisting of SEQ ID NOs: 66-67. The XTEN may comprise an amino acid sequence comprising 20, 30, 40, 50, 60, 70, 80, 90, 100, 200, 250, 300, 350, 400, 450, 500, 550, 600, 650, 700, 750 or more amino acids based on or derived from the amino acid sequence selected from a group consisting of SEQ ID NOs: 66-67. The XTEN may comprise an amino acid sequence comprising 20 or more amino acids based on or derived from the amino acid sequence selected from a group consisting of SEQ ID NOs: 66-67. The XTEN may comprise an amino acid sequence comprising 30 or more amino acids based on or derived from the amino acid sequence selected from a group consisting of SEQ ID NOs: 66-67. The XTEN may comprise an amino acid sequence comprising 40 or more amino acids based on or derived from the amino acid sequence selected from a group consisting of SEQ ID NOs: 66-67. The XTEN may comprise an amino acid sequence comprising 50 or more amino acids based on or derived from the amino acid sequence selected from a group consisting of SEQ ID NOs: 66-67. The XTEN may comprise an amino acid sequence comprising 60 or more amino acids based on or derived from the amino acid sequence selected from a group consisting of SEQ ID NOs: 66-67.

The XTEN may comprise an amino acid sequence less than about 400 amino acids. The XTEN may comprise an amino acid sequence less than about 390, 380, 375, 370, 365, 360, 350, 340, 330, 320, 310, 300, 290, 280, 270, 260, 250, 240, 230, 220, 210, 200, 190, 180, 170, 160, 150, 140, 130, 120, 100, 90, 80, 70, 60, 50, 40, 30, 20, or 10 amino acids. The XTEN may comprise an amino acid sequence less than about 350 amino acids. The XTEN may comprise an amino acid sequence less than about 300 amino acids. The XTEN may comprise an amino acid sequence less than about 250 amino acids.

The XTEN may comprise an amino acid sequence that may be at least about 50% homologous to an amino acid sequence selected from a group consisting of SEQ ID NOs: 66-67. The XTEN may comprise an amino acid sequence that may be at least about 55%, 60%, 65%, 70%, 75%, 80%, 85%, 90%, 92%, 95%, 97%, or 99% homologous to an amino acid sequence selected from a group consisting of SEQ ID NOs: 66-67. The XTEN may comprise an amino acid sequence that may be at least about 60% homologous to an amino acid sequence selected from a group consisting of SEQ ID NOs: 66-67. The XTEN may comprise an amino acid sequence that may be at least about 70% homologous to an amino acid sequence selected from a group consisting of SEQ ID NOs: 66-67. The XTEN may comprise an amino acid sequence that may be at least about 80% homologous to an amino acid sequence selected from a group consisting of SEQ ID NOs: 66-67.

The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence characterized in that the sum of glycine (G), alanine (A), serine (S), threonine (T), glutamate (E), aspartate (D), leucine (L) and proline (P) residues constitutes more than about 75% of the total amino acid sequence. The XTEN may comprise an amino acid sequence characterized in that the sum of glycine (G), alanine (A), serine (S), threonine (T), glutamate (E), aspartate (D), leucine (L) and proline (P) residues constitutes more than about 80% of the total amino acid sequence. The XTEN may comprise an amino acid sequence characterized in that the sum of glycine (G), alanine (A), serine (S), threonine (T), glutamate (E), aspartate (D), leucine (L) and proline (P) residues constitutes more than about 85% of the total amino acid sequence. The XTEN may comprise an amino acid sequence characterized in that the sum of glycine (G), alanine (A), serine (S), threonine (T), glutamate (E), aspartate (D), leucine (L) and proline (P) residues constitutes more than about 90% of the total amino acid sequence. The XTEN may comprise an amino acid sequence characterized in that the sum of glycine (G), alanine (A), serine (S), threonine (T), glutamate (E), aspartate (D), leucine (L) and proline (P) residues constitutes more than about 95% of the total amino acid sequence.

The XTEN may be attached to the N-terminus, C-terminus, or the N- and C-terminus of the TA. The XTEN may be attached to a cysteine residue located at the N- or C-terminus of the TA. The XTEN may be chemically attached to a cysteine residue located at the N- or C-terminus of the TA. The XTEN may be attached to the sulfur atom of a cysteine residue located at the N- or C-terminus of the TA. The XTEN may be chemically attached to the sulfur atom of a cysteine residue located at the N- or C-terminus of the TA. The XTEN may be attached to an internal residue of the TA. The XTEN may be attached to a cysteine residue located at an internal position of the TA. The XTEN may be chemically attached to a cysteine residue located at an internal position of the TA. The XTEN may be attached to the sulfur atom of a cysteine residue located at an internal position of the TA. The XTEN may be chemically attached to the sulfur atom of a cysteine residue located at internal position of the TA.

The XTEN-mTAs may comprise one or more TAs. The XTEN-mTA may comprise 2, 3, 4, 5, 6, 7, 8, 9, 10, 11, 12, 13, 14, 15, 16, 17, 18, 19, 20 or more TAs. The XTEN-mTA may comprise 2 or more TAs. The XTEN-mTA may comprise 3 or more TAs. The XTEN-mTA may comprise 4 or more TAs.

The TA may comprise an amino acid sequence comprising at least a portion of a polypetide sequence selected from a group consisting of SEQ ID NOs: 10-56. The TA may comprise an amino acid sequence comprising 10 or more amino acids based on or derived from the amino acid sequence selected from a group consisting of SEQ ID NOs: 10-56. The TA may comprise an amino acid sequence comprising 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180 or more amino acids based on or derived from the amino acid sequence selected from a group consisting of SEQ ID NOs: 10-56. The TA may comprise an amino acid sequence comprising 20 or more amino acids based on or derived from the amino acid sequence selected from a group consisting of SEQ ID NOs: 10-56. The TA may comprise an amino acid sequence comprising 30 or more amino acids based on or derived from the amino acid sequence selected from a group consisting of SEQ ID NOs: 10-56. The TA may comprise an amino acid sequence comprising 50 or more amino acids based on or derived from the amino acid sequence selected from a group consisting of SEQ ID NOs: 10-56. The TA may comprise an amino acid sequence comprising 70 or more amino acids based on or derived from the amino acid sequence selected from a group consisting of SEQ ID NOs: 10-56. The amino acids based on or derived from the amino acid sequence selected from a group consisting of SEQ ID NOs: 10-56 may be consecutive. amino acids based on or derived from the amino acid sequence selected from a group consisting of SEQ ID NOs: 10-56 may be non-consecutive.

The TA may comprise an amino acid sequence less than about 400 amino acids. The TA may comprise an amino acid sequence less than about 375, 350, 325, 300, 275, 250, 225, 200, 190, 180, 170, 160, 150, 140, 130, 120, 100, 90, 80, 70, 60, 50, 40, 30, 20, or 10 amino acids.

The TA may comprise an amino acid sequence that is at least about 50% homologous to an amino acid sequence selected from a group consisting of SEQ ID NOs: 10-56. The TA may comprise an amino acid sequence that is at least about 55%, 60%, 65%, 70%, 75%, 80%, 85%, 90%, 92%, 95%, 97%, or 99% homologous to an amino acid sequence selected from a group consisting of SEQ ID NOs: 10-56. The TA may comprise an amino acid sequence that is at least about 60% homologous to an amino acid sequence selected from a group consisting of SEQ ID NOs: 10-56. The TA may comprise an amino acid sequence that is at least about 70% homologous to an amino acid sequence selected from a group consisting of SEQ ID NOs: 10-56. The TA may comprise an amino acid sequence that is at least about 80% homologous to an amino acid sequence selected from a group consisting of SEQ ID NOs: 10-56. The TA may comprise an amino acid sequence that is at least about 90% homologous to an amino acid sequence selected from a group consisting of SEQ ID NOs: 10-56.

The TA may be relaxin or an analog thereof. The XTEN may be attached to the N-terminus, C-terminus, or the N- and C-terminus of relaxin or an analog thereof. The XTEN may be attached to a cysteine residue located at the N- or C-terminus of relaxin or an analog thereof. The XTEN may be chemically attached to a cysteine residue located at the N- or C-terminus of relaxin or an analog thereof. The XTEN may be attached to the sulfur atom of a cysteine residue located at the N- or C-terminus of relaxin or an analog thereof. The XTEN may be chemically attached to the sulfur atom of a cysteine residue located at the N- or C-terminus of relaxin or an analog thereof. The XTEN may be attached to a cysteine residue located at the N- or C-terminus of relaxin or an analog thereof. The XTEN may be chemically attached to a cysteine residue located at an internal position of relaxin or an analog thereof. The XTEN may be attached to the sulfur atom of a cysteine residue located at an internal position of relaxin or an analog thereof. The XTEN may be chemically attached to the sulfur atom of a cysteine residue located at an internal position of relaxin or an analog thereof.

The TA may be FGF21 or an analog thereof. The XTEN may be attached to the N-terminus, C-terminus, or the N- and C-terminus of FGF21 or an analog thereof. The XTEN may be attached to a cysteine residue located at the N- or C-terminus of FGF21 or an analog thereof. The XTEN may be chemically attached to a cysteine residue located at the N- or C-terminus of FGF21 or an analog thereof. The XTEN may be attached to the sulfur atom of a cysteine residue located at the N- or C-terminus of FGF21 or an analog thereof. The XTEN may be chemically attached to the sulfur atom of a cysteine residue located at the N- or C-terminus of FGF21 or an analog thereof. The XTEN may be attached to an internal residue of FGF1 or an analog thereof. The XTEN may be attached to a cysteine residue located at an internal position of FGF21 or an analog thereof. The XTEN may be chemically attached to a cysteine residue located at an internal position of FGF21 or an analog thereof. The XTEN may be attached to the sulfur atom of a cysteine residue located at an internal position of FGF21 or an analog thereof. The XTEN may be chemically attached to the sulfur atom of a cysteine residue located at an internal position of FGF21 or an analog thereof.

The TA may be leptin or an analog thereof. The XTEN may be attached to the N-terminus, C-terminus, or the N- and C-terminus of leptin or an analog thereof. The XTEN may be attached to a cysteine residue located at the N- or C-terminus of leptin or an analog thereof. The XTEN may be chemically attached to a cysteine residue located at the N- or C-terminus of leptin or an analog thereof. The XTEN may be attached to the sulfur atom of a cysteine residue located at the N- or C-terminus of leptin or an analog thereof. The XTEN may be chemically attached to the sulfur atom of a cysteine residue located at the N- or C-terminus of leptin or an analog thereof. The XTEN may be attached to an internal residue of leptin or an analog thereof. The XTEN may be attached to a cysteine residue located at an internal position of leptin or an analog thereof. The XTEN may be chemically attached to a cysteine residue located at an internal position of leptin or an analog thereof. The XTEN may be attached to the sulfur atom of a cysteine residue located at an internal position of leptin or an analog thereof. The XTEN may be chemically attached to the sulfur atom of a cysteine residue located at an internal position of leptin or an analog thereof.

The TA may be Toxin-550 or an analog thereof. The XTEN may be attached to the N-terminus, C-terminus, or the N- and C-terminus of Toxin-550 or an analog thereof. The XTEN may be attached to a cysteine residue located at the N- or C-terminus of Toxin-550 or an analog thereof. The XTEN may be chemically attached to a cysteine residue located at the N- or C-terminus of Toxin-550 or an analog thereof. The XTEN may be attached to the sulfur atom of a cysteine residue located at the N- or C-terminus of Toxin-550 or an analog thereof. The XTEN may be chemically attached to the sulfur atom of a cysteine residue located at the N- or C-terminus of Toxin-550 or an analog thereof. The XTEN may be attached to an internal residue of Toxin-550 or an analog thereof. The XTEN may be attached to a cysteine residue located at an internal position of Toxin-550 or an analog thereof. The XTEN may be chemically attached to a cysteine residue located at an internal position of Toxin-550 or an analog thereof. The XTEN may be attached to the sulfur atom of a cysteine residue located at an internal position of Toxin-550 or an analog thereof. The XTEN may be chemically attached to the sulfur atom of a cysteine residue located at an internal position of Toxin-550 or an analog thereof.

The XTEN-mTAs disclosed herein may further comprise one or more linkers. The XTEN-mTAs disclosed herein may further comprise two or more linkers. The XTEN-mTAs disclosed herein may further comprise three or more linkers. The XTEN-mTAs disclosed herein may further comprise four or more linkers. The XTEN-mTAs disclosed herein may further comprise five or more linkers.

Each of the one or more linkers on the XTEN-mTAs may be formed from a reactive precursor comprising a halogen atom. The reactive precursor may be a haloacetamide attached to the XTEN. The haloacetamide may be located at the N-terminus of the XTEN. The haloacetamide may be chloroacetamide, bromoacetamide, or iodoacetamide.

The TAs disclosed herein may further comprise one or more linkers. The TAs disclosed herein may further comprise two or more linkers. The TAs disclosed herein may further comprise three or more linkers. The TAs disclosed herein may further comprise four or more linkers. The TAs disclosed herein may further comprise five or more linkers.

The one or more linkers may enable attachment of an XTEN to a therapeutic agent or to another XTEN.

Therapeutic Agent (TA)

The mTAs disclosed herein may comprise one or more therapeutic agents. The mTAs may comprise two or more therapeutic agents. The mTAs may comprise 3, 4, 5, 6, 7 or more therapeutic agents. The therapeutic agents may be different. The therapeutic agents may be the same. As used herein, the term "therapeutic agent" refers to candidate proteins or peptides that modulate the activity of a target protein, target peptide, target cell or target tissue. Modulating the activity can comprise increasing, decreasing, stimulating, or preventing the activity or expression of the target protein, peptide, cell or tissue. Target proteins or peptides include proteins involved in the etiology of a disease or disorder by virtue of expression or activity. TAs may comprise at least a portion of a protein, biomolecule, chemical, toxin, drug or any combination thereof. Exemplary TAs may include, but are not limited to, at least a portion of a hormone, kinase, receptor, ligand, growth factor, regulatory protein, metabolic protein, cytokine, chemokine, interferon, phosphatase, antibody or any combination thereof. The TA may be a wild-type peptide or a modified peptide comprising one or more amino acid additions, deletions, substitutions, or a combination thereof. The one or more amino acid additions or substitutions may be located at the C-terminus of the peptide. The one or more amino acid additions or substitutions may be located at the N-terminus of the peptide. The one or more amino acid additions or substitutions may be located at the N-terminus or the C-terminus of the peptide. The one or more amino acid additions or substitutions may be located at both the N-terminus and C-terminus of the peptide. The one or more amino acid additions or substitutions may be located at a non-terminus position of the peptide.

The TA may be a hormone. Examples of hormones include, but are not limited to, peptide hormones, lipid and phospholipid-derived hormones, and monoamines. Peptide hormones generally consist of chains of amino acids. Examples of small peptide hormones include, but are not limited to thyrotropin-releasing hormone (TRH) and vasopressin. Peptides composed of scores or hundreds of amino acids may be referred to as proteins. Examples of protein hormones include insulin and growth hormone. More complex protein hormones may bear carbohydrate side-chains and may be called glycoprotein hormones. Luteinizing hormone, follicle-stimulating hormone and thyroid-stimulating hormone are examples of glycoprotein hormones. Lipid and phospholipid-derived hormones are generally derived from lipids such as linoleic acid and arachidonic acid and phospholipids. Protein hormones may comprise steroid hormones that are derived from cholesterol and the eicosanoids. Examples of steroid hormones are testosterone and cortisol.

Eicosanoids may comprise prostaglandins. Monoamines may be derived from aromatic amino acids like phenylalanine, tyrosine, tryptophan by the action of aromatic amino acid decarboxylase enzymes. The TA may be oxyntomodulin. The TA may be exendin-4. The TA may be exenatide. The TA may be glucagon-like peptide (GLP-1). The TA may be glucagon. The TA may be leptin. The TA may be betatrophin.

The TA may be a relaxin peptide or derivative thereof. The relaxin peptide may comprise a modified relaxin peptide. The modified relaxin peptide may comprise at least a portion of a wild-type relaxin peptide comprising one or more amino acid mutations. The relaxin peptide may comprise at least a portion of an A chain and/or B chain of a relaxin peptide. The relaxin peptide may comprise one or more amino acid mutations. The one or more amino acid mutations may comprise a deletion, substitution, addition or a combination thereof. The one or more amino acid mutations may comprise addition of one or more amino acid residues to the wild-type relaxin polypeptide. The one or more amino acid mutations may comprise substitution of one or more amino acid residues of the wild-type relaxin polypeptide. The one or more amino acid mutations may comprise deletion of one or more amino acid residues of the wild-type relaxin polypeptide. The one or more amino acid mutations may comprise one or more amino acid substitutions of one or more amino acid residues in an A chain and/or B chain of a wild-type relaxin peptide. The one or more amino acid mutations may comprise one or more amino acid substitutions of one or more amino acid residues in an A chain of a wild-type relaxin peptide. The one or more amino acid substitutions of one or more amino acid residues in the A chain may be selected from a group consisting of Y3C, A7C, T16C, R18C, S19C, or a combination thereof. The one or more amino acid mutations may comprise one or more amino acid substitutions of one or more amino acid residues in a B chain of a wild-type relaxin peptide. The one or more amino acid substitutions of one or more amino acid residues in the B chain may be selected from a group consisting of D1A, S2C, M4C, S26C, and S29C, or any combination thereof. The one or more amino acid mutations may comprise a Y3C substitution in an A chain of a wild-type relaxin peptide. The one or more amino acid mutations may comprise an A7C substitution in an A chain of a wild-type relaxin peptide. The one or more amino acid mutations may comprise a T16C substitution in an A chain of a wild-type relaxin peptide. The one or more amino acid mutations may comprise a R18C substitution in an A chain of a wild-type relaxin peptide. The one or more amino acid mutations may comprise a S19C substitution in an A chain of a wild-type relaxin peptide. The one or more amino acid mutations may comprise a S2C substitution in a B chain of a wild-type relaxin peptide. The one or more amino acid mutations may comprise a D1A substitution in a B chain of a wild-type relaxin peptide. The one or more amino acid mutations may comprise a M4C substitution in a B chain of a wild-type relaxin peptide. The one or more amino acid mutations may comprise a S26C substitution in a B chain of a wild-type relaxin peptide. The one or more amino acid mutations may comprise a S29C substitution in a B chain of a wild-type relaxin peptide. The one or more amino acid mutations may comprise substituting one or more amino acid residues of a wild-type relaxin peptide with a cysteine residue. The one or more amino acid residues of the wild-type relaxin peptide are selected from a group consisting of alanine, methionine, arginine, serine, threonine, and tyrosine. The one or more amino acid mutations may comprise adding one or more amino acid residues to a wild-type relaxin peptide.

The TA may be a growth factor. Growth factors may include, but are not limited to, cytokines and hormones. Examples of growth factors include, but are not limited to, adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β), tumor necrosis factor-alpha (TNF-α) and vascular endothelial growth factor (VEGF). The TA may be fibroblast growth factor 21 (FGF21).

The TA may be a cell regulatory protein. The TA may be a cell regulatory protein of the transforming growth factor beta superfamily. The TA may be a member of the decapentaplegic-Vg related (DVR) related subfamily. The TA may be a member of the activin/inhibin subfamily. The TA may be a member of the TGF-beta subfamily. The TA may be a growth differentiation factor (GDF). The GDF may be GDF1, GDF2, GDF3, GDF5, GDF6, GFD8, GDF9, GDF10, GDF11, and GDF15. The TA may be growth differentiation factor 11 (GDF11).

The TA may be a protein. The protein may be a member of the angiopoietin-like family of secreted factors. The protein may be an angiopoietin-like protein (ANGPTL). Examples of ANGPTLs include, but are not limited to, ANGPTL1, ANGPTL2, ANGPTL3, ANGPTL4, ANGPTL5, ANGPTL6 and ANGPTL7. The TA may be ANGPTL3.

The TA may comprise a peptide selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, and derivatives thereof, the derivative being a peptide comprising one or more amino acid additions, deletions, or substitutions, or a combination thereof. The TA may comprise relaxin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, or VM-24, or a derivative thereof, the derivative being a peptide comprising one or more amino acid additions, deletions, or substitutions, or a combination thereof. The TA may comprise oxyntomodulin, exenatide, exendin-4, glucagon-like protein-1 (GLP-1), GLP-2, glucagon, a GLP-1R and GIPR dual agonist, or a GLP-1R and GCGR dual agonist, or a derivative thereof, the derivative being a peptide comprising one or more amino acid additions, deletions, or substitutions, or a combination thereof. The TA may comprise H1 relaxin, H2 relaxin, H3 relaxin, human INSL3, human INSL4, human INSL6, human IGF1, human IGFII, or human insulin, or a derivative thereof, the derivative being a peptide comprising one or more amino acid additions, deletions, or substitutions, or a combination thereof. The TA may comprise H1 relaxin, H2 relaxin, or H3 relaxin, or a derivative thereof, the derivative being a peptide comprising one or more amino acid additions, deletions, or substitutions, or a combination thereof. The TA may comprise human INSL3, human INSL4, human INSL6, human IGF1, or human IGFII, or a derivative thereof, the derivative being a peptide comprising one or more amino acid additions, deletions, or substitutions, or a combination thereof. The TA may comprise a peptidyl toxin or a derivative thereof, the derivative being a peptide comprising one or more amino acid additions, deletions, or substitutions, or a combination thereof. The TA may comprise Toxin-550, Moka, or VM-24, or a derivative thereof, the derivative being a peptide comprising one or more amino acid additions, deletions, or substitutions, or a combination thereof. The TA may comprise human insulin or a derivative thereof, the derivative being a peptide comprising one or more amino acid additions, deletions, or substitutions, or a combination thereof.

The TA may be encoded by a nucleotide sequence based on or derived from a nucleotide sequence selected from the group comprising SEQ ID NO: 1-9. The TA may be encoded by a nucleotide sequence that is at least about 50% homologous to a nucleotide sequence selected from the group comprising SEQ ID NO: 1-9. The TA may be encoded by a nucleotide sequence that is at least about 55%, 60%, 65%, 70%, 75%, 80%, 85%, 90%, 92%, 95%, 97%, 99%, or 100% homologous to a nucleotide sequence selected from the group comprising SEQ ID NO: 1-9. The TA may be encoded by a nucleotide sequence that is at least about 70% homologous to a nucleotide sequence selected from the group comprising SEQ ID NO: 1-9. The TA may be encoded by a nucleotide sequence that is at least about 75% homologous to a nucleotide sequence selected from the group comprising SEQ ID NO: 1-9. The TA may be encoded by a nucleotide sequence that is at least about 80% homologous to a nucleotide sequence selected from the group comprising SEQ ID NO: 1-9. The TA may comprise one or more nucleotide sequences selected from the group comprising SEQ ID NO: 1-9. The TA may comprise two or more nucleotide sequences selected from the group comprising SEQ ID NO: 1-9. The TA may comprise three or more nucleotide sequences selected from the group comprising SEQ ID NO: 1-9. The TA may comprise four or more nucleotide sequences selected from the group comprising SEQ ID NO: 1-9. The TA may comprise 5, 6, 7, 8, or 9 nucleotide sequences selected from the group comprising SEQ ID NO: 1-9.

The TA may comprise an amino acid sequence selected from the group comprising SEQ ID NO: 10-56. The TA may comprise an amino acid sequence that is at least about 50% homologous to an amino acid sequence selected from the group comprising SEQ ID NO: 10-56. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 10-56. The TA may comprise an amino acid sequence that is at least about 70% homologous to an amino acid sequence selected from the group comprising SEQ ID NO: 10-56. The TA may comprise an amino acid sequence that is at least about 75% homologous to an amino acid sequence selected from the group comprising SEQ ID NO: 10-56. The TA may comprise an amino acid sequence that is at least about 80% homologous to an amino acid sequence selected from the group comprising SEQ ID NO: 10-56. The TA may comprise one or more amino acid sequences selected from the group comprising SEQ ID NO: 10-56. The TA may comprise two or more amino acid sequences selected from the group comprising SEQ ID NO: 10-56. The TA may comprise three or more amino acid sequences selected from the group comprising SEQ ID NO: 10-56. The TA may comprise four or more amino acid sequences selected from the group comprising SEQ ID NO: 10-56. The TA may comprise 5, 6, 7, 8, 9, 10, 11, 12, 13, 14, or 15 or more amino acid sequences selected from the group comprising SEQ ID NO: 10-56.

The TA may comprise 20 or more consecutive amino acids from an amino acid sequence selected from the group comprising SEQ ID NO: 10-56. The TA may comprise 30, 40, 50, 60, 70, 80, 90, 100, 110, 120, 130 or more consecutive amino acids from an amino acid sequence selected from the group comprising SEQ ID NO: 10-56.

The TAs may be from a mammal or non-mammal. The TAs may be from a human.

Alternatively, the TAs may be from a goat, sheep, cow, rabbit, monkey, dog, cat or a combination thereof. The TAs may be from a reptile. The TAs may be from a snake or lizard. The TAs may be from an amphibian. The TAs may be from a frog or toad. The TAs may be from an avian. The TAs may be recombinant.

The TAs disclosed herein may further comprise one or more linkers. The TAs disclosed herein may further comprise two or more linkers. The TAs disclosed herein may further comprise three or more linkers. The TAs disclosed herein may further comprise four or more linkers. The TAs disclosed herein may further comprise five or more linkers.

Pharmacokinetics

Mechanisms by which the modified therapeutic agents positively influence pharmacokinetic or pharmacodynamic behavior include, but are not limited to, (i) preventing or mitigating in vivo proteolytic degradation or other activity-diminishing chemical modification of the therapeutic agent; (ii) improving half-life or other pharmacokinetic properties by reducing renal filtration, decreasing receptor-mediated clearance or increasing bioavailability; (iii) reducing toxicity; (iv) improving solubility; and/or (v) increasing biological activity and/or target selectivity of the therapeutic agent.

The half-life extending moieties may enhance one or more pharmacokinetic properties of a therapeutic agent (TA) when attached to the TA.

The modified therapeutic agents disclosed herein may enhance the one or more pharmacokinetic properties of the TA by at least about 200% as measured by pharmacodynamics when compared to the TA alone. The modified therapeutic agents disclosed herein may enhance the one or more pharmacokinetic properties of the TA by at least about 300%, 400%, 500%, 600%, 700%, 800%, 900%, 1000% as measured by pharmacodynamics when compared to the TA alone. The modified therapeutic agents disclosed herein may enhance the one or more pharmacokinetic properties of the TA by at least about 250% as measured by pharmacodynamics when compared to the TA alone. The modified therapeutic agents disclosed herein may enhance the one or more pharmacokinetic properties of the TA by at least about 300% as measured by pharmacodynamics when compared to the TA alone. The modified therapeutic agents disclosed herein may enhance the one or more pharmacokinetic properties of the TA by at least about 350% as measured by pharmacodynamics when compared to the TA alone. The modified therapeutic agents disclosed herein may enhance the one or more pharmacokinetic properties of the TA by at least about 400% as measured by pharmacodynamics when compared to the TA alone. The modified therapeutic agents disclosed herein may enhance the one or more pharmacokinetic properties of the TA by at least about 500% as measured by pharmacodynamics when compared to the TA alone.

The pharmacokinetic properties may comprise a half-life. The half-life of the modified therapeutic agent may be at least about two-fold longer compared to the half-life of the TA alone. The half-life of the modified therapeutic agent disclosed herein may be at least about 3-fold, 4-fold, or 5-fold longer compared to the half-life of the TA alone. The half-life of the modified therapeutic agent disclosed herein may be at least about 6-, 7-, 8-, 9-, 10-, 15-, 20-, 25-, 30-, 35-, 40-, 45-, or 50-fold longer compared to the half-life of the TA alone. The half-life of the modified therapeutic agent disclosed herein may be at least about 5-fold longer compared to the half-life of the TA alone. The half-life of the modified therapeutic agent disclosed herein may be at least about 10-fold longer compared to the half-life of the TA alone.

In addition, the modified therapeutic agents may have positive effects on terms of increasing manufacturability, and/or reducing immunogenicity of the therapeutic agent-compared to an unconjugated form of the therapeutic agent.

A modified therapeutic agent may have comparable activity to the TA alone. A modified therapeutic agent may have similar activity to the TA alone. A modified therapeutic agent may have increased activity to the TA alone. A modified therapeutic agent may have decreased activity to the TA alone.

Attachment of one or more lipids to a TA to form an LC may diminish the activity of the LC relative to the TA alone by no more than 2-, 3-, 4-, 5-, 6-, 7-, 8-, 9-, or 10-fold less activity. Attachment of a polyglycol region to a TA to form a modified therapeutic agent may diminish the activity of the modified therapeutic agent relative to the TA alone by no more than 2-, 3-, 4-, 5-, 6-, 7-, 8-, 9-, or 10-fold less activity.

Therapeutic Use

Further disclosed herein are mTAs for treating, alleviating, inhibiting and/or preventing one or more diseases and/or conditions. The disease and/or condition may be a chronic disease or condition. Alternatively, the disease and/or condition may be an acute disease or condition. The disease or condition may be recurrent, refractory, accelerated, or in remission. The disease or condition may affect one or more cell types. The one or more diseases and/or conditions may be an autoimmune disease, inflammatory disease, cardiovascular disease and pregnancy. The mTAs disclosed herein may be administered to a subject in need thereof.

Disclosed herein are methods of treating a disease or condition in a subject in need thereof, the method comprising administering to the subject a composition comprising an LC, wherein the LC comprises a lipid attached to a therapeutic agent, wherein the therapeutic agent is relaxin or a derivative thereof. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition may be pregnancy. The LC may be used to treat preeclampsia or induce labor. The LC may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin.

Further disclosed herein are methods for treating a disease or condition in a subject in need thereof, the method comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more therapeutic agents (TAs), wherein the one or more lipids are attached to at least one cysteine residue in the one or more therapeutic agents. The one or more TAs may comprise relaxin. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The LC may be used to treat preeclampsia or induce labor. The LC may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin.

Further disclosed herein are methods for treating a disease or condition in a subject in need thereof, the method comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, fatty amines, and fatty alcohols, and derivatives thereof; and (b) a therapeutic agent (TA), wherein TA is a peptide and the one or more lipids are attached to the peptide via an amino acid on the peptide. The TA may comprise relaxin. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The LC may be used to treat preeclampsia or induce labor. The LC may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin.

Further disclosed herein are methods of treating a disease or condition in a subject in need thereof, the method comprising administering to the subject one or more lipid conjugates (LCs) of Formula (Ia): TA-A$^1$-P$^1$-L, wherein TA is a therapeutic agent; $A^1$ is a chemical group linking TA and $P^1$; $P^1$ is a bond or $-PEG-A^2-$; PEG is a chemical group comprising one or more polyethyleneglycol subunits; $A^2$ is a chemical group linking PEG and L; and L is a lipid. The TA may comprise relaxin. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The LC may be used to treat preeclampsia or induce labor. The LC may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin.

Further disclosed herein are methods of treating a disease or condition in a subject in need thereof, the method comprising administering to the subject one or more lipid conjugates (LCs) of Formula (I): $TA-A^1-P^1-L$, wherein TA is a therapeutic agent; $A^1$ is a chemical group linking TA and $P^1$ or L; $P^1$ is a bond or comprises polyglycol; and L is a lipid. The TA may comprise relaxin. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The LC may be used to treat preeclampsia or induce labor. The LC may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin.

Provided herein is a method of preventing or treating a metabolic disease or condition in a subject in need thereof comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more therapeutic agents (TA), wherein the one or more lipids are attached to the one or more cysteine residues in the one or more therapeutic agents. The one or more TAs may comprise GLP-1, Exendin-4, exenatide, oxyntomodulin, glucagon, FGF21, or derivative thereof. The GLP-1 may be a human GLP-1. The FGF21 may be a human FGF21. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a metabolic disease or condition in a subject in need thereof comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, fatty amines, and fatty alcohols, and derivatives thereof and (b) a therapeutic agent (TA), wherein the TA is a peptide and the one or more lipids are attached to the TA via an amino acid residue on the peptide. The TA may comprise GLP-1, Exendin-4, exenatide, oxyntomodulin, glucagon, FGF21, or derivative thereof. The GLP-1 may be a human GLP-1. The FGF21 may be a human FGF21. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a metabolic disease or condition in a subject in need thereof comprising administering to the subject one or more lipid conjugates (LCs) of Formula (Ia): $TA-A^1-P^1-L$, wherein TA is a therapeutic agent; $A^1$ is a chemical group linking TA and $P^1$; $P^1$ is a bond or $-PEG-A^2-$; PEG is a chemical group comprising one or more polyethyleneglycol subunits; $A^2$ is a chemical group linking PEG and L; and L is a lipid. The TA may comprise GLP-1, Exendin-4, exenatide, oxyntomodulin, glucagon, FGF21, or derivative thereof. The GLP-1 may be a human GLP-1. The FGF21 may be a human FGF21. The one or more lipids may comprise one or more sterols, sterol derivatives, bile acids, vitamin E derivatives, fatty di-acids, fatty acids, fatty amides, and fatty alcohols. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a metabolic disease or condition in a subject in need thereof comprising administering to the subject one or more lipid conjugates (LCs) of Formula (I): $TA-A^1-P^1-L$, wherein TA is a therapeutic agent; $A^1$ is a chemical group linking TA and $P^1$ or L; $P^1$ is a bond or comprises polyglycol; and L is a lipid. The TA may comprise GLP-1, exendin-4, exenatide, oxyntomodulin, glucagon, FGF21, or derivative thereof. The GLP-1 may be a human GLP-1. The FGF21 may be a human FGF21. The one or more lipids may comprise one or more sterols, sterol derivatives, bile acids, vitamin E derivatives, fatty di-acids, fatty acids, fatty amides, and fatty alcohols. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a central nervous system (CNS) disorder in a subject in need thereof comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more therapeutic agents (TAs), wherein the one or more lipids are attached to at least one cysteine residue in the one or more therapeutic agents. The one or more TAs may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a central nervous system (CNS) disorder in a subject in need thereof comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, fatty amines, and fatty alcohols, and derivatives thereof and (b) a therapeutic agent (TA), wherein the TA is a peptide and the one or more lipids are attached to the TA via an amino acid residue on the peptide. The TA may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a central nervous system (CNS) disorder in a subject in need thereof comprising administering to the subject one or more lipid conjugates (LCs) of Formula (Ia): TA-$A^1$-$P^1$-L, wherein TA is a therapeutic agent; $A^1$ is a chemical group linking TA and $P^1$; $P^1$ is a bond or -PEG-$A^2$-; PEG is a chemical group comprising one or more polyethyleneglycol subunits; $A^2$ is a chemical group linking PEG and L; and L is a lipid. The one or more lipids may comprise one or more sterols, sterol derivatives, bile acids, vitamin E derivatives, fatty di-acids, fatty acids, fatty amides, and fatty alcohols. The one or more lipids may comprise one or more sterols, sterol derivatives, bile acids, vitamin E derivatives, fatty di-acids, fatty acids, fatty amides, and fatty alcohols. The TA may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a central nervous system (CNS) disorder in a subject in need thereof comprising administering to the subject one or more lipid conjugates (LCs) of Formula (I): TA-$A^1$-$P^1$-L, wherein TA is a therapeutic agent; $A^1$ is a chemical group linking TA and $P^1$ or L; $P^1$ is a bond or comprises polyglycol; and L is a lipid. The one or more lipids may comprise one or more sterols, sterol derivatives, bile acids, vitamin E derivatives, fatty di-acids, fatty acids, fatty amides, and fatty alcohols. The one or more lipids may comprise one or more sterols, sterol derivatives, bile acids, vitamin E derivatives, fatty di-acids, fatty acids, fatty amides, or fatty alcohols, or derivatives thereof. The TA may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a disease or condition which benefits from a GLP-1R and/or glucagon receptor (GCGR) agonist in a subject in need thereof comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more therapeutic agents (TAs), wherein the one or more lipids are attached to at least one cysteine residue in the one or more therapeutic agents. The one or more TAs may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a disease or condition which benefits from a GLP-1R and/or glucagon receptor (GCGR) agonist in a subject in need thereof comprising administering to the subject one or more LCs, wherein the one or more lipid conjugates (LCs) comprise (a) one or more lipids, the lipids selected from a group consisting of sterols, sterol derivatives, bile acids, vitamin E derivatives, fatty di-acids, fatty acids, fatty amides, fatty amines, and fatty alcohols, and derivatives thereof and (b) a therapeutic agent (TA), wherein the TA is a peptide and the one or more lipids are attached to the TA via an amino acid residue on the peptide. The TA may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a disease or condition which benefits from a GLP-1R and/or glucagon receptor (GCGR) agonist in a subject in need thereof comprising administering to the subject one or more lipid conjugates (LCs) of Formula (Ia): TA-$A^1$-$P^1$-L, wherein TA is a therapeutic agent; $A^1$ is a chemical group linking TA and $P^1$; $P^1$ is a bond or -PEG-$A^2$-; PEG is a chemical group comprising one or more polyethyleneglycol subunits; $A^2$ is a chemical group linking PEG and L; and L is a lipid. The one or more lipids may comprise one or more sterols, sterol derivatives, bile acids, vitamin E derivatives, fatty di-acids, fatty acids, fatty amides, and fatty alcohols.

The one or more lipids may comprise one or more sterols, sterol derivatives, bile acids, vitamin E derivatives, fatty di-acids, fatty acids, fatty amides, and fatty alcohols. The TA may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a disease or condition which benefits from a GLP-1R and/or glucagon receptor (GCGR) agonist in a subject in need thereof comprising administering to the subject one or more lipid conjugates (LCs) of Formula (I): TA-$A^1$-$P^1$-L, wherein TA is a therapeutic agent; $A^1$ is a chemical group linking TA and $P^1$ or L; $P^1$ is a bond or comprises polyglycol; and L is a lipid. The one or more lipids may comprise one or more sterols, sterol derivatives, bile acids, vitamin E derivatives, fatty di-acids, fatty acids, fatty amides, and fatty alcohols, or derivatives thereof. The one or more lipids may comprise one or more sterols, sterol derivatives, bile acids, vitamin E derivatives, fatty di-acids, fatty acids, fatty amides, or fatty alcohols, or derivatives thereof. The TA may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Further disclosed herein are mTAs for use in treating, alleviating, inhibiting and/or preventing one or more diseases and/or conditions. The disease and/or condition may be a chronic disease or condition. Alternatively, the disease and/or condition may be an acute disease or condition. The disease or condition may be recurrent, refractory, accelerated, or in remission. The disease or condition may affect one or more cell types. The one or more diseases and/or conditions may be an autoimmune disease, inflammatory disease, cardiovascular disease and/or pregnancy. The modified therapeutic agents (mTAs) may comprise a therapeutic agent and one or more half-life extending moieties, wherein the therapeutic agent is a peptide that is covalently attached to each of the one or more half-life extending moieties via a cysteine residue on the peptide; and the half-life of the modified therapeutic agent is longer than the half-life of the peptide alone. The mTAs may comprise two or more half-life extending moieties. The two or more half-life extending moieties may be identical. The two or more half-life extending moieties may be different. Each of the one or more half-life extending moieties may comprise a lipid, a polyglycol region, or a combination thereof. Each of the one or more half-life extending moieties may comprise a lipid. Each of the one or more half-life extending moieties may comprise a polyglycol region. Each of the one or more half-life extending moieties may comprise a lipid and a polyglycol region. Each of the one or more half-life extending moieties may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The peptide may comprise one or more amino acid additions, deletions, or substitutions, or a combination thereof. The peptide may be selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof. The peptide may be selected from relaxin, H1 relaxin, H2 relaxin, H3 relaxin, human INSL3, human INSL4, human INSL6, human IGF1, human IGFII, human insulin, oxyntomodulin, exenatide, exendin-4, glucagon-like protein-1 (GLP-1), GLP-2, glucagon, a GLP-1R and GIPR dual agonist, a GLP-1R and GCGR dual agonist, leptin, betatrophin, FGF 21, GDF 11, ANGPTL3, peptide-based toxin, Moka, and VM-24, or a derivative thereof, the derivative being a peptide comprising one or more amino acid additions, deletions, or substitutions, or a combination thereof. The peptide may be relaxin or a derivative thereof, the derivative being a peptide comprising one or more amino acid additions, deletions, or substitutions, or a combination thereof. The peptide may be encoded by an amino acid sequence comprising at least a portion of a polypeptide sequence selected from a group consisting of SEQ ID NO: 10-56. The peptide may be encoded by an amino acid sequence comprising 10 or more amino acids based on or derived from a polypeptide sequence selected from a group consisting of SEQ ID NO: 10-56. The peptide may comprise an amino acid sequence that is at least about 50% homologous to an amino acid sequence selected from the group comprising SEQ ID NO: 10-56. The peptide may comprise an amino acid sequence that is at least 80% homologous to an amino acid sequence selected from the group comprising SEQ ID NO: 10-56. The peptide may comprise one or more amino acid sequences selected from the group comprising SEQ ID NO: 10-56. The peptide may comprise two or more amino acid sequences selected from the group comprising SEQ ID NO: 10-56. The peptide may further comprise a linker. The cysteine residue may be located on the N-terminus or C-terminus of the peptide. The cysteine residue may be located on a non-terminus position of the peptide. The cysteine residue may be an amino acid addition or substitution on the peptide. The mTAs disclosed herein may be administered to a subject in need thereof. The mTA may be an XTEN-mTA. The mTA may be a LC.

Disclosed herein are methods of treating a disease or condition in a subject in need thereof, the method comprising administering to the subject a composition comprising an mTA, wherein the mTA comprises a half-life extending moiety attached to a therapeutic agent, wherein the therapeutic agent is relaxin or a derivative thereof. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The therapeutic agent may further comprise a linker. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition may be pregnancy. The mTA may be used to treat preeclampsia or induce labor. The mTA may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin. The mTA may be an XTEN-mTA.

Further disclosed herein are methods for treating a disease or condition in a subject in need thereof, the method comprising administering to the subject one or more mTAs, wherein the one or more modified therapeutic agents (mTAs) comprise (a) one or more half-life extending moieties, the half-life extending moieties comprising an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) a therapeutic agents (TA), wherein the one or more half-life extending moieties are attached to at least one cysteine residue in the one or more therapeutic agents. The TA may comprise relaxin. The TA may comprise a linker. The TA may comprise a modified polypeptide. The modified polypeptide may comprise a polypeptide comprising one or more mutations. The one or more mutations may be a substitution, deletion, or insertion. The modified peptide may comprise a polypeptide attached to a linker. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The mTA may be used to treat preeclampsia or induce labor. The mTA may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin. The mTA may be an XTEN-mTA.

Further disclosed herein are methods for treating a disease or condition in a subject in need thereof, the method comprising administering to the subject one or more mTAs, wherein the one or more modified therapeutic agents (mTAs) comprise (a) one or more half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) a therapeutic agent (TA), wherein TA is a peptide and the one or more half-life extending moieties are attached to the peptide via an amino acid on the peptide. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise relaxin. The TA may further comprise a linker. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The mTA may be used to treat preeclampsia or induce labor. The mTA may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin. The mTA may be an XTEN-mTA.

Further disclosed herein are methods of treating a disease or condition in a subject in need thereof, the method comprising administering to the subject one or more modified therapeutic agents (mTAs) of Formula IIa): TA-$A^1$-$P^1$-X, wherein TA is a therapeutic agent; $A^1$ is a chemical group linking TA and $P^1$; $P^1$ is a bond or -PEG-$A^2$-; PEG is a chemical group comprising one or more polyethyleneglycol subunits; $A^2$ is a chemical group linking PEG and X; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence; and $P^1$ is a bond. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise relaxin. The TA may further comprise a linker. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The mTA may be used to treat preeclampsia or induce labor. The mTA may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin.

Further disclosed herein are methods of treating a disease or condition in a subject in need thereof, the method comprising administering to the subject one or more modified therapeutic agents (mTAs) of Formula (II): TA-$A^1$-$P^1$-X, wherein TA is a therapeutic agent; $A^1$ is a chemical group linking TA and $P^1$ or X; $P^1$ is a bond or comprises polyglycol; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence; and $P^1$ is a bond. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise relaxin. The TA may further comprise a linker. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The mTA may be used to treat preeclampsia or induce labor. The mTA may be administered with one or more additional therapeutic agents. The additional therapeutic agents may comprise one or more of anti-inflammatory drugs, statins, diuretics, beta-blockers, angiotensin converting enzyme inhibitors and angiotensin II receptor blockers. The additional therapeutic agent may be aspirin. The mTA may be an XTEN-mTA.

Provided herein is a method of preventing or treating a metabolic disease or condition in a subject in need thereof comprising administering to the subject one or more mTAs, wherein the one or more modified therapeutic agents (mTAs) comprise (a) one or more half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) one or more therapeutic agents (TA), wherein the one or more half-life extending moieties are attached to the one or more cysteine residues in the one or more therapeutic agents. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The one or more TAs may comprise GLP-1, Exendin-4, exenatide, oxyntomodulin, glucagon, FGF21, or derivative thereof. The GLP-1 may be a human GLP-1. The FGF21 may be a human FGF21. The one or more TAs may further comprise a linker. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease. The mTA may be an XTEN-mTA.

Provided herein is a method of preventing or treating a metabolic disease or condition in a subject in need thereof comprising administering to the subject one or more mTAs, wherein the one or more modified therapeutic agents (mTAs) comprise (a) one or half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) a therapeutic agent (TA), wherein the TA is a peptide and the one or more half-life extending moieties are attached to the TA via an amino acid residue on the peptide. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The peptide may comprise GLP-1, Exendin-4, exenatide, oxyntomodulin, glucagon, FGF21, or derivative thereof. The GLP-1 may be a human GLP-1. The FGF21 may be a human FGF21. The peptide may further comprise a linker. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease. The mTA may be an XTEN-mTA.

Provided herein is a method of preventing or treating a metabolic disease or condition in a subject in need thereof comprising administering to the subject one or more modified therapeutic agents (mTAs) of Formula IIa): TA-A$^1$-P$^1$-X, wherein TA is a therapeutic agent; A$^1$ is a chemical group linking TA and P$^1$; P$^1$ is a bond or -PEG-A$^2$-; PEG is a chemical group comprising one or more polyethyleneglycol subunits; A$^2$ is a chemical group linking PEG and X; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and P$^1$ is a bond. The TA may comprise GLP-1, Exendin-4, exenatide, oxyntomodulin, glucagon, FGF21, or derivative thereof. The GLP-1 may be a human GLP-1. The FGF21 may be a human FGF21. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease. The mTA may be an XTEN-mTA.

Provided herein is a method of preventing or treating a metabolic disease or condition in a subject in need thereof comprising administering to the subject one or more modified therapeutic agents (mTAs) of Formula (I): TA-A$^1$-P$^1$-X, wherein TA is a therapeutic agent; A$^1$ is a chemical group linking TA and P$^1$ or X; P$^1$ is a bond or comprises polyglycol; and X is a half-life extending moiety. The half-life extending moiety comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, FGF21, or derivative thereof. The GLP-1 may be a human GLP-1. The FGF21 may be a human FGF21. The metabolic disease or condition may be diabetes. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease. The mTA may be an XTEN-mTA.

Provided herein is a method of preventing or treating a central nervous system (CNS) disorder in a subject in need thereof comprising administering to the subject one or more mTAs, wherein the one or more modified therapeutic agents (mTAs) comprise (a) one or more half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) one or more therapeutic agents (TAs), wherein the one or more half-life extending moieties are attached to at least one cysteine residue in the one or more therapeutic agents. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The one or more TAs may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis. The mTA may be an XTEN-mTA.

Provided herein is a method of preventing or treating a central nervous system (CNS) disorder in a subject in need thereof comprising administering to the subject one or more mTAs, wherein the one or more modified therapeutic agents (mTAs) comprise (a) one or more half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) a therapeutic agent (TA), wherein the TA is a peptide and the one or more half-life extending moieties are attached to the TA via an amino acid residue on the peptide. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis. The mTA may be an XTEN-mTA.

Provided herein is a method of preventing or treating a central nervous system (CNS) disorder in a subject in need thereof comprising administering to the subject one or more modified therapeutic agents (mTAs) of Formula IIa): TA-$A^1$-$P^1$-X, wherein TA is a therapeutic agent; $A^1$ is a chemical group linking TA and $P^1$; $P^1$ is a bond or -PEG-$A^2$-; PEG is a chemical group comprising one or more polyethyleneglycol subunits; $A^2$ is a chemical group linking PEG and X; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence; and $P^1$ is a bond. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis. The mTA may be an XTEN-mTA.

Provided herein is a method of preventing or treating a central nervous system (CNS) disorder in a subject in need thereof comprising administering to the subject one or more modified therapeutic agents (mTAs) of Formula (II): TA-$A^1$-$P^1$-X, wherein TA is a therapeutic agent; $A^1$ is a chemical group linking TA and $P^1$ or X; $P^1$ is a bond or comprises polyglycol; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence; and $P^1$ is a bond. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, or derivative thereof. The GLP-1 may be a human GLP-1. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis. The mTA may be an XTEN-mTA.

Provided herein is a method of preventing or treating a disease or condition which benefits from a GLP-1R and/or glucagon receptor (GCGR) agonist in a subject in need thereof comprising administering to the subject one or more mTAs, wherein the one or more modified therapeutic agents (mTAs) comprise (a) one or more half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) one or more therapeutic agents (TAs), wherein the one or more half-life extending moieties are attached to at least one cysteine residue in the one or more therapeutic agents. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The one or more TAs may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases. The mTA may be an XTEN-mTA.

Provided herein is a method of preventing or treating a disease or condition which benefits from a GLP-1R and/or glucagon receptor (GCGR) agonist in a subject in need thereof comprising administering to the subject one or more mTAs, wherein the one or more modified therapeutic agents (mTAs) comprise (a) one or more half-life extending moieties, wherein the one or more half-life extending moieties comprises an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets; and (b) a therapeutic agent (TA), wherein the TA is a peptide and the one or more half-life extending moieties are attached to the TA via an amino acid residue on the peptide. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases. The mTA may be an XTEN-mTA.

Provided herein is a method of preventing or treating a disease or condition which benefits from a GLP-1R and/or glucagon receptor (GCGR) agonist in a subject in need thereof comprising administering to the subject one or more modified therapeutic agents (mTAs) of Formula IIa): TA-$A^1$-$P^1$-X, wherein TA is a therapeutic agent; $A^1$ is a chemical group linking TA and $P^1$; $P^1$ is a bond or -PEG-$A^2$-; PEG is a chemical group comprising one or more polyethyleneglycol subunits; $A^2$ is a chemical group linking PEG and X; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii) a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence; and $P^1$ is a bond. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases. The mTA may be an XTEN-mTA.

Provided herein is a method of preventing or treating a disease or condition which benefits from a GLP-1R and/or glucagon receptor (GCGR) agonist in a subject in need thereof comprising administering to the subject one or more modified therapeutic agents (mTAs) of Formula (I): TA-$A^1$-$P^1$-X, wherein TA is a therapeutic agent; $A^1$ is a chemical group linking TA and $P^1$ or X; $P^1$ is a bond or comprises polyglycol; and X is a half-life extending moiety. The half-life extending moiety may comprise an extended recombinant polypeptide (XTEN) comprising (i) an amino acid sequence characterized in that the sum of glycine (G), alanine (A), serine (S), threonine (T), glutamate (E), aspartate (D), leucine (L) and proline (P) residues constitutes more than about 70% of the total amino acid sequence; (ii)

a substantially non-repetitive amino acid sequence; (iii) an amino acid sequence that has less than about 10% alpha helices; and/or (iv) an amino acid sequence that has less than about 10% beta-sheets. The XTEN may comprise an amino acid sequence characterized in that the sum of glycine (G), alanine (A), serine (S), threonine (T), glutamate (E), aspartate (D), leucine (L) and proline (P) residues constitutes more than about 75%, 77%, 80%, 83%, 85%, 87%, 90%, 92%, 95%, 97%, or 99% the total amino acid sequence. The XTEN may comprise an amino acid sequence selected from SEQ ID NOs: 66-67. The XTEN may comprise an amino acid sequence that is at least about 50%, 55%, 60%, 65%, 70%, 75%, 80%, 83%, 85%, 87%, 90%, 93%, 95%, 97%, or 99% or more homologous to an amino acid sequence of SEQ ID NOs: 66-67. The TA may comprise GLP-1, exendin-4, exenatide, oxyntomodulin, glucagon, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases. The mTA may be an XTEN-mTA.

Further disclosed herein are XTEN-mTAs for treating, alleviating, inhibiting and/or preventing one or more diseases and/or conditions. The disease and/or condition may be a chronic disease or condition. Alternatively, the disease and/or condition may be an acute disease or condition. The disease or condition may be recurrent, refractory, accelerated, or in remission. The disease or condition may affect one or more cell types. The one or more diseases and/or conditions may be an autoimmune disease, inflammatory disease, cardiovascular disease and pregnancy. The XTEN-mTAs disclosed herein may be administered to a subject in need thereof.

Compositions

Disclosed herein are pharmaceutical compositions comprising a modified therapeutic agent disclosed herein. The compositions may comprise 1, 2, 3, 4, 5, 6, 7, 8, 9, 10 or more modified therapeutic agents. The modified therapeutic agents may be different. Alternatively, the modified therapeutic agents may be the same or similar. The modified therapeutic agents may comprise different therapeutic agents, different half-life extending moieties, or a combination thereof. The half-life extending moieties may be the same or similar.

Further disclosed herein are pharmaceutical compositions comprising an LC disclosed herein. The compositions may comprise 1, 2, 3, 4, 5, 6, 7, 8, 9, 10 or more LCs. The LCs may be different. Alternatively, the LCs may be the same or similar. The LCs may comprise different therapeutic agents, different lipids, or a combination thereof. The lipids may be the same or similar.

The compositions described herein may further comprise one or more pharmaceutically acceptable salts, excipients, or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically may be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of LCs, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(-)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(-)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141).

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and triglycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which an LC, nucleic acid encoding at least a portion of an LC, or vector comprising a nucleic acid encoding at least a portion of an LC disclosed herein has been absorbed or encapsulated. Where an implantation device is used, the device may be implanted into any suitable tissue or organ, and delivery of an LC, nucleic acid encoding at least a portion of an LC, or vector comprising a nucleic acid encoding at least a portion of an LC disclosed herein can be directly through the device via bolus, or via continuous administration, or via catheter using continuous infusion.

A pharmaceutical composition comprising an LC, nucleic acid encoding at least a portion of an LC, or vector comprising a nucleic acid encoding at least a portion of an LC disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Certain formulations comprising an LC, nucleic acid encoding at least a portion of an LC, or vector comprising a nucleic acid encoding at least a portion of an LC disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of an antibody comprising an LC, nucleic acid encoding at least a portion of an LC, or vector comprising a nucleic acid encoding at least a portion of an LC disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that may be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

Vectors, Host Cells and Recombinant Methods

A TA, as disclosed herein, may be expressed by recombinant methods. Generally, a nucleic acid encoding a TA may be isolated and inserted into a replicable vector for further cloning (amplification of the DNA) or for expression. DNA encoding the LC may be prepared by PCR amplification and sequenced using conventional procedures (e.g., by using oligonucleotide probes that are capable of binding specifically to nucleotides encoding LC). In an exemplary embodiment, a nucleic acid encoding an LC is PCR amplified, restriction enzyme digested and gel purified. The digested LC may be inserted into a replicable vector. The replicable vector containing the digested LC insertion may be transformed or transduced into a host cell for further cloning (amplification of the DNA) or for expression. Host cells may be prokaryotic or eukaryotic cells.

Polynucleotide sequences encoding polypeptide components of the LCs disclosed herein may be obtained by PCR amplification with overlapping oligonucleotide primers. Polynucleotide sequences may be isolated and sequenced from TA producing cells. Alternatively, polynucleotides may be synthesized using nucleotide synthesizer or PCR techniques. Once obtained, sequences encoding the polypeptides are inserted into a recombinant vector capable of replicating and expressing heterologous polynucleotides in prokaryotic and/or eukaryotic hosts.

In addition, phage vectors containing replicon and control sequences that are compatible with the host microorganism may be used as transforming vectors in connection with these hosts. For example, bacteriophage such as λGEM™-11 may be utilized in making a recombinant vector which can be used to transform susceptible host cells such as *E. coli* LE392.

TAs may be expressed intracellularly (e.g., cytoplasm) or extracellularly (e.g., secretion). For extracellular expression, the vector may comprise a secretion signal which enables translocation of the TA to the outside of the cell.

Suitable host cells for cloning or expression of TA-encoding vectors include prokaryotic or eukaryotic cells. The host cell may be a eukaryotic. Examples of eukaryotic cells include, but are not limited to, Human Embryonic Kidney (HEK) cell, Chinese Hamster Ovary (CHO) cell, fungi, yeasts, invertebrate cells (e.g., plant cells and insect cells), lymphoid cell (e.g., YO, NSO, Sp20 cell). Other examples of suitable mammalian host cell lines are monkey kidney CV1 line transformed by SV40 (COS-7); baby hamster kidney cells (BHK); mouse Sertoli cells; monkey kidney cells (CV 1); African green monkey kidney cells (VERO-76); human cervical carcinoma cells (HELA); canine kidney cells (MDCK; buffalo rat liver cells (BRL 3A); human lung cells (W138); human liver cells (HepG2); mouse mammary tumor (MMT 060562); TR1 cells; MRC 5 cells; and FS4 cells. The host cell may be a prokaryotic cell (e.g., *E. coli*).

Host cells may be transformed with vectors containing nucleotides encoding a TA. Transformed host cells may be cultured in media. The media may be supplemented with one or more agents for inducing promoters, selecting transformants, or amplifying or expressing the genes encoding the desired sequences. Methods for transforming host cells are known in the art and may include electroporation, calcium chloride, or polyethylene glycol/DMSO.

Alternatively, host cells may be transfected or transduced with vectors containing nucleotides encoding a TA. Transfected or transduced host cells may be cultured in media. The media may be supplemented with one or more agents for inducing promoters, selecting transfected or transduced cells, or expressing genes encoding the desired sequences.

The expressed TAs may be secreted into and recovered from the periplasm of the host cells or transported into the culture media. Protein recovery from the periplasm may involve disrupting the host cell. Disruption of the host cell may comprise osmotic shock, sonication or lysis. Centrifugation or filtration may be used to remove cell debris or whole cells. The TAs may be further purified, for example, by affinity resin chromatography.

Alternatively, TAs that are secreted into the culture media may be isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

TA production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors may use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described herein. Cells may be grown for shorter periods prior to induction. Cells are usually induced for about 12-50 hours, although longer or shorter induction times may be used.

To improve the production yield and quality of the TAs disclosed herein, various fermentation conditions can be modified. For example, to improve the proper assembly and folding of the secreted TA polypeptides, additional vectors overexpressing chaperone proteins, such as Dsb proteins (DsbA, DsbB, DsbC, DsbD and or DsbG) or FkpA (a peptidylprolyl cis, trans-isomerase with chaperone activity) may be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, hydroxylapatite chromatography, gel electrophoresis, dialysis, and affinity chromatography and gel filtration using, for example, Sephadex G-75.

TAs may be concentrated using a commercially available protein concentration filter, for example, an Amicon or Millipore Pellicon® ultrafiltration unit.

Protease inhibitors or protease inhibitor cocktails may be included in any of the foregoing steps to inhibit proteolysis of the TA.

In some cases, a TA or fragment thereof may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. The refolding/oxidation solution may also contain a reducing agent or the reducing agent plus its oxidized form in a specific ratio to generate a particular redox potential allowing for disulfide shuffling to occur in the formation of the protein's cysteine bridge(s). Some of the commonly used redox couples include cystein/cystamine, glutathione (GSH)/dithiobis GSH, cupric chloride, dithiothreitol(DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like. Choice of buffer may determine the three-dimensional structure of the refolded peptide. Use of a buffer comprising ammonium sulfate may result in the desired refolded peptide in better yield than other types of buffers.

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g. a mTA alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises a mTA as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the modified therapeutic agent composition.

In certain embodiments, the composition comprising the modified therapeutic agent is formulated in accordance with routine procedures as a pharmaceutical composition adapted for intravenous administration to mammals, such as humans, bovines, felines, canines, and murines. Typically, compositions for intravenous administration are solutions in sterile isotonic aqueous buffer. Where necessary, the composition may also include a solubilising agent and a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the composition described herein which may be effective in the treatment, inhibition and prevention of a disease or disorder associated with aberrant expression and/or activity of a protein can be determined by standard clinical techniques. In addition, in vitro assays may optionally be employed to help identify optimal dosage ranges. The precise dose to be employed in the formulation may also depend on the route of administration, and the seriousness of the disease or disorder, and should be decided according to the judgment of the practitioner and each patient's circumstances. Effective doses are extrapolated from dose-response curves derived from in vitro or animal model test systems.

Definitions

The terms below, as used herein, have the following meanings, unless indicated otherwise:

"Amino" refers to the —$NH_2$ radical.
"Cyano" or "nitrile" refers to the —CN radical.
"Hydroxy" or "hydroxyl" refers to the —OH radical.
"Nitro" refers to the —$NO_2$ radical.
"Oxo" refers to the =O substituent.
"Oxime" refers to the =N—OH substituent.
"Thioxo" refers to the =S substituent.

"Alkyl" refers to a straight or branched hydrocarbon chain radical, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

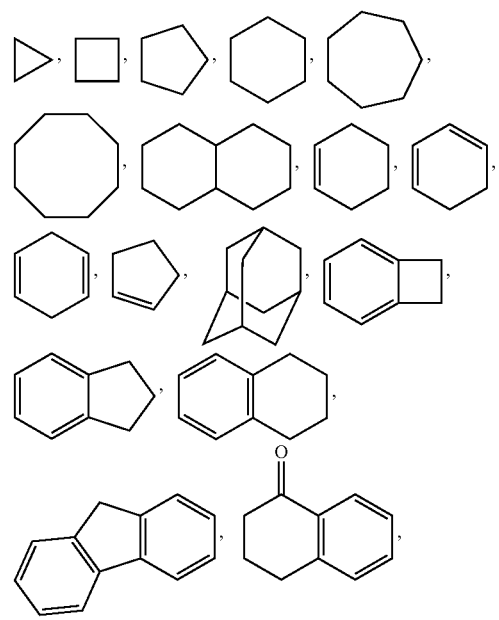

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —$OR_a$ where $R_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

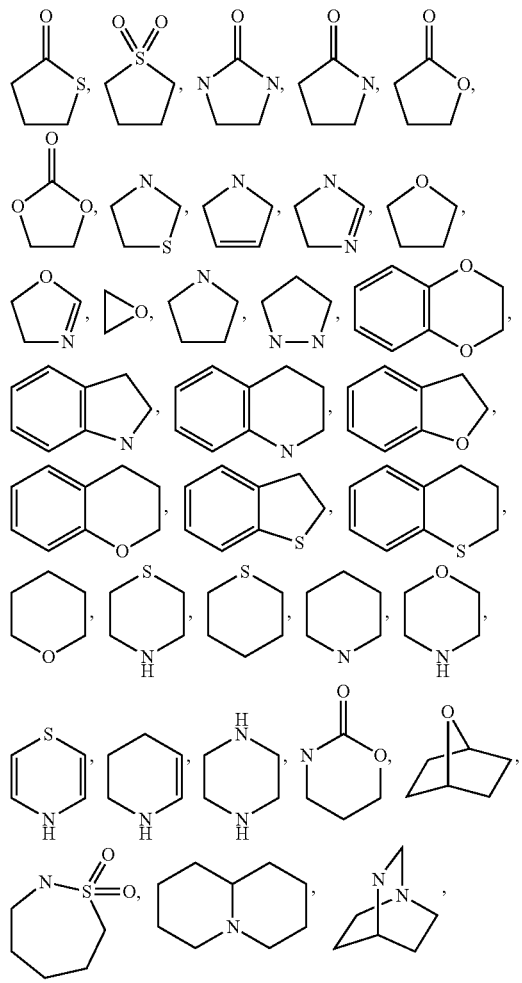

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, azepinyl, phenazinyl, benzimidazolyl, benzindolyl, benzofuranyl, benzofuranonyl, benzoxazolyl, benzothiazolyl, benzothiadiazolyl, benzothiophenyl, benzoxadiazolyl, benzodioxolyl, benzo[b][1,4]dioxepinyl, 1,4-benzodioxanyl, benzonaphthofuranyl, benzotriazolyl, benzodioxolyl, benzodioxinyl, benzopyranyl, benzopyranonyl, benzothienyl (benzothiophenyl), benzo[4,6]imidazo[1,2-a]pyridinyl, carbazolyl, cinnolinyl, dibenzofuranyl, dibenzothiophenyl, furanonyl, imidazolyl, indolyl, isoxazolyl, isoquinolinyl, indolizinyl, indazolyl, isoindolyl, indolinyl, isoindolinyl, indolizinyl, isothiazolyl, isoindolyloxadiazolyl, indazolyl, naphthyridinyl, oxadiazolyl, 2-oxoazepinyl, oxiranyl, 1-oxidopyridinyl, 1-oxidopyrimidinyl, 1-oxidopyrazinyl, 1-oxidopyridazinyl, 1-phenyl-1H-pyrrolyl, phenothiazinyl, phenoxazinyl, pyridinyl, pyridazinyl, pyrimidinyl, pyrazinyl, pyrrolyl, pyrazinyl, pyrazolyl, purinyl, phthalazinyl, pteridinyl, quinolinyl, quinazolinyl, quinoxalinyl, quinuclidinyl, triazolyl, tetrazolyl, thiazolyl, triazinyl, thiadiazolyl, tetrahydroquinolinyl, thiazolyl, and thiophenyl and the like, and their oxides, such as for example pyridyl-N-oxide. Illustrative examples of heteroaryl groups include the following moieties:

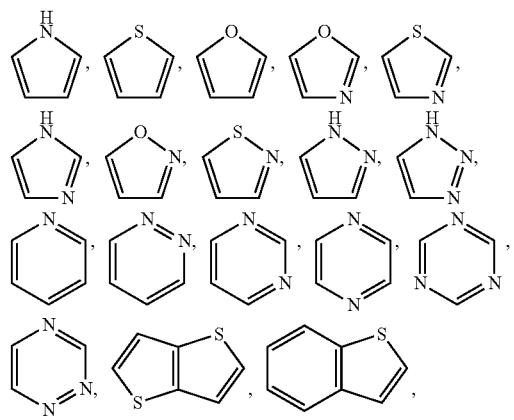

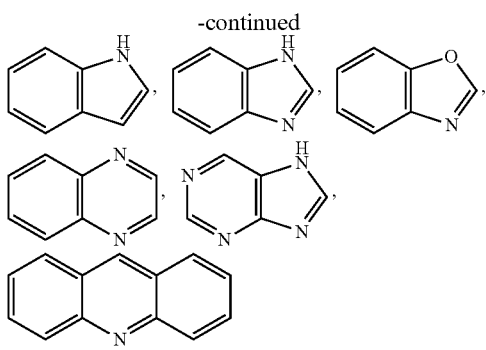

and the like.

All the above groups may be either substituted or unsubstituted. The term "substituted" as used herein means any of the above groups (e.g., alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

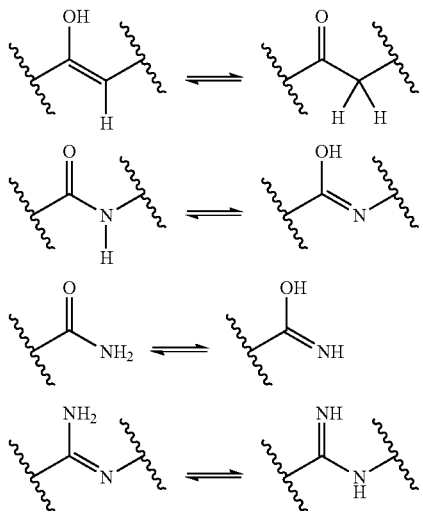

-continued

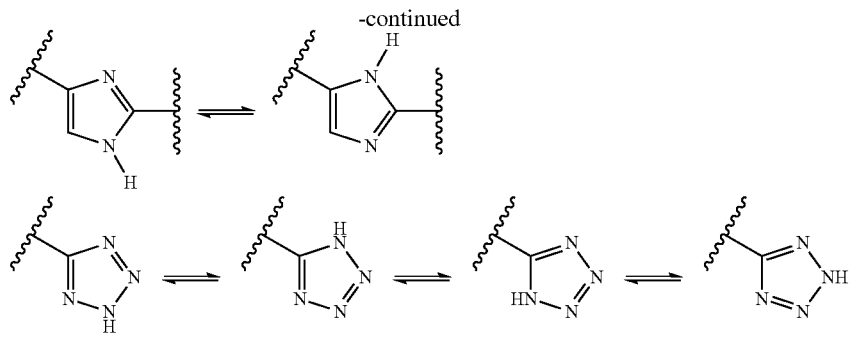

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. Metabolites of a compound may be formed by oxidative processes and correspond to the corresponding hydroxy-containing compound. A compound may be metabolized to one or more pharmacologically active metabolites.

As used herein, a "derivative" of a peptide refers to, but is not limited to, a modified peptide that allows for lipid attachment (such as one or more amino acid residue replacements or L- vs D-amino acid replacements), a fragment, an analog with one or more additional amino acids, a complex and/or an aggregate of the peptide. A derivative of a peptide may be a homolog that has at least 50% homology with respect to the peptide. A derivative of a peptide may be a homolog that has at least 60% homology with respect to the peptide. A derivative of a peptide may be a homolog that has at least 70% homology with respect to the peptide. A derivative of a peptide may be a homolog that has at least 80% homology with respect to the peptide. A derivative of a peptide may be a homolog that has at least 90% homology with respect to the peptide.

Terms such as "treating" or "treatment" or "to treat" or "alleviating" or "to alleviate" may refer to: 1) therapeutic measures that cure, slow down, lessen symptoms of, and/or halt progression of a diagnosed pathologic condition or disorder; and/or 2) prophylactic or preventative measures that prevent and/or slow the development of a targeted pathologic condition or disorder. Thus those in need of treatment include those already with the disorder; those prone to have the disorder; and those in whom the disorder is to be prevented.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

As used herein, the term "therapeutic agent" or "peptide therapeutic agent" refers to a protein or peptide that modulates the activity of another protein, peptide, cell or tissue. Modulating the activity can comprise increasing, decreasing, stimulating, or preventing the activity or expression of the protein, peptide, cell or tissue. Therapeutic agents may modulate the activity of proteins or peptides involved in the etiology of a disease or disorder. Exemplary TAs may include, but are not limited to, at least a portion of a hormone, kinase, receptor, ligand, growth factor, regulatory protein, metabolic protein, cytokine, chemokine, interferon, phosphatase, antibody or any combination thereof.

"Disorder" or "disease" refers to a condition that would benefit from treatment with a substance/molecule (e.g., a mTA as disclosed herein) or method disclosed herein. This includes chronic and acute disorders or diseases including those pathological conditions which predispose the mammal to the disorder in question.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

The terms "modified therapeutic agent," "mTA," "lipid conjugate," and "LC" may be used interchangeably. These terms may refer to a therapeutic agent (TA) attached to a half-life extending moiety.

EXAMPLES

Example 1. Construction and Expression of Recombinant Relaxin 2 with Linker Between Chain B and Chain a as a CBD Fusion with Mutation S26C and S29C The purpose of this experiment was to construct and express a GGGRGGR (SEQ ID NO: 68) linker between chain B and chain A recombinant relaxin 2 with mutation S26C and S29C.

Materials
Materials used for this experiment include:
pVB008 relaxin 2 linker linear
pVB008 relaxin 2 linker linear S26C
pVB008 relaxin 2 linker linear S29C
Oligo stock solution 100 µM of SEQ ID NOs: 38-46 as disclosed in Table 6.

FIG. 4 depicts a schematic of pVB008 relaxin2 linker vector.

Step 1. Assembling PCR—Amplification of Relaxin Fragments

PCR reactions to generate relaxin fragments wild type or with S26C or S29C mutations were prepared as follows:

| Reagent | Reaction 1 (µl) | Reaction 2 (µl) | Reaction 3 (µl) | Reaction 4 (µl) |
| --- | --- | --- | --- | --- |
| Oligo mix | 1 | 2 | 4 | 8 |
| 5× Buffer | 20 | 20 | 20 | 20 |
| 10 mM dNTP | 4 | 4 | 4 | 4 |
| One Taq | 1 | 1 | 1 | 1 |
| H₂O | 74 | 73 | 61 | 67 |

Figure 5:
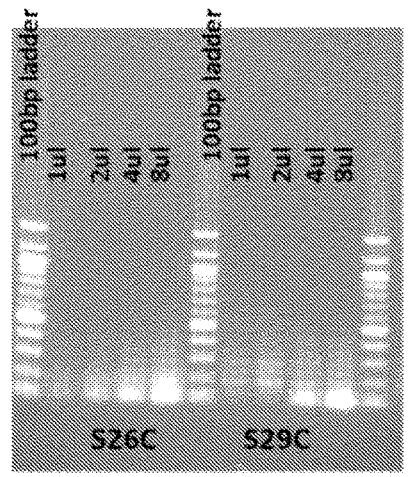
FIG. 5. shows an agarose gel of the Relaxin2 S26C and Relaxin2 S29C PCR products FIG. 6. shows an agarose gel of the Relaxin2 S26C linker and Relaxin2 S29C linker PCR products.

Step 2. PCR Program
Relaxin2 fragments (wild type, S26C and S29C) were amplified by conducting the following PCR program: 94° C.-2 Min, followed by 20 cycles of 94° C.-15 Sec, 42° C.-30 Sec, and 68° C.-15 Sec PCR products of the relaxin-2 fragments were run on a 0.8% agarose gel. As shown in FIG. 5, Lanes 1, 6 and 11 contain the 100 bp ladder, Lane 2-5 contain the S26C oligo mix Step 1 Reaction 1-4 reactions, respectively, Lane 7-10 contain the S29C oligo mix Step 1 Reaction 1-4 reactions, respectively.

Step 3. Amplification of Relaxin2 Linker
PCR reactions to generate a relaxin2 linker were prepared as follows:

| Reagent | Reaction 1 (µl) | Reaction 2 (µl) | Reaction 3 (µl) |
| --- | --- | --- | --- |
| Assembling mix | 1 | 2 | 4 |
| 5× Buffer | 20 | 20 | 20 |
| 10 mM dNTP | 4 | 4 | 4 |
| 10 µM Primer mix | 4 | 4 | 4 |
| One Taq | 1 | 1 | 1 |
| H₂O | 70 | 69 | 67 |

The 10 µM Primer mix contained a Relaxin2 forward primer (pVB008 Relaxin2 Amp for (#60): AATCTGTATTTCCAGGGATCCGGTGGTGA=SEQ ID NO: 64 and a Relaxin2 reverse primer (Relaxin2 Linker Amp rev (#211) TGGCTAAGC TTTAGCAGAAAC-GAGCCAGAGAACGTTTGGTGC AACCAACGTGGC=SEQ ID NO: 65). The PCR amplified reaction 1 mix from step 2 was used for the assembling mix.

Relaxin 2 linker was amplified by conducting the following PCR program: 94° C.-2 Min, followed by 25 cycles of 94° C.-15 Sec, 52° C.-15 Sec, and 68° C.-60 Sec.

Figure 6:
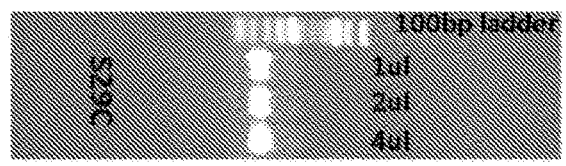

PCR products of the relaxin-2 linker amplification were run on a 0.8% agarose gel. As shown in FIG. 6, Lane 1 contains the 100 ladder, Lane 2 contains S29C Step 3 Reaction 1, Lane 3 contains S29C Step 3 Reaction 2, and Lane 4 contains S29C Step 3 Reaction 3.

Step 4. Digestion of Vector pVB008 and pAC145
A restriction digest of vector pVB008 and pAC145 was performed to prepare the vectors for insertion of the Relaxin 2 linker PCR product. The restriction digest was prepared as follows:
20 µl pVB008/pAC045
10 µl 10× Buffer #4
2 µl HindIII-HF
2 µl BamHI-HF
66 µl H₂O The restriction digest reaction was incubated at 37° C. for 1 hour.

Step 5. Digestion of Insert
A restriction digest of the Relaxin 2 linker PCR products (wild type, S26C, and S29C) was performed to prepare the PCR product for insertion into pVB008 and pAC145 vectors. The restriction digest was prepared as follows:
20 µl full length fragment
10 µl 10× Buffer #4
2 µl HindIII-HF
2 µl BamHI-HF
66 µl H₂O The restriction digest reaction was incubated at 37° C. for 1 hour.

Figure 7:
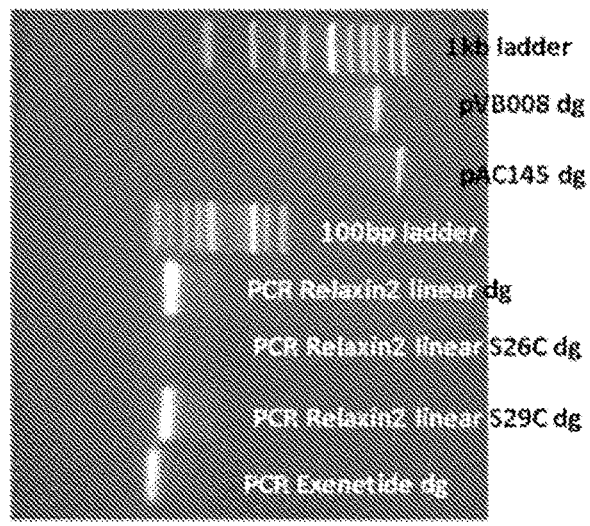
FIG. 7. shows an agarose gel of restriction enzyme digested vectors (pVB008 and pAC145) and PCR products (Relaxin2, Relaxin2 S26C linker, Relaxin2 S29C linker, and Exenatide).

Step 6. Gel Purification
The pVB008 digested vector, pAC145 digested vector and Relaxin2 linker insert were run on an agarose gel. As shown in FIG. 7, Lane 1 contains the 1 kb ladder, Lane 2 contains the digested pVB008 vector, Lane 3 contains the digested pAC145 vector, Lane 4 contains the 100 bp ladder, Lane 5 contains the Relaxin2-linker insert, Lane 6 contains the Relaxin2 S26C-linker insert and Lane 7 contains the Relaxin2 S29C-linker insert. The digested vectors and Relaxin2 PCR products were gel purified as per the manufacturer's instructions (NucleoSpin Gel and PCR Cleanup Macherey-Nagel).

Step 7. Ligation/Transformation

The gel-purified digested vector (vector dg) and the digested PCR product (relaxin-2 linear dg (Insert)) were ligated by the following ligation reaction:
5 μl Vector dg
1 μl relaxin-2 linear dg (Insert)
2 μl 10× Buffer
1 μl T4 DNA Ligase
11 μl H$_2$O The ligation reaction was incubated at room temperature (RT) for 1 hour.

The ligated product was then used to transform NEB turbo Competent cells, 2 μl of the ligation reaction was transformed into NEB turbo Competent Cells according to protocol. The transformed cells were plated on LB/Kan plates.

5 colonies were picked and inoculated in 5 ml LB+Kan. The cells were grown for 6 hours at 37° C.

Step 8. Preparation of DNA for Sequencing

DNA was prepared from 1.5 ml of each of the 5 cultures using a NucleoSpin DNA Mini Prep Macherey-Nagel according to the protocol. Sequencing of the DNA was performed to verify the insertion of Relaxin2 into the pVB008 and pAC145 vector.

Step 9. Expression and Purification of Relaxin Peptides

Figure 8:
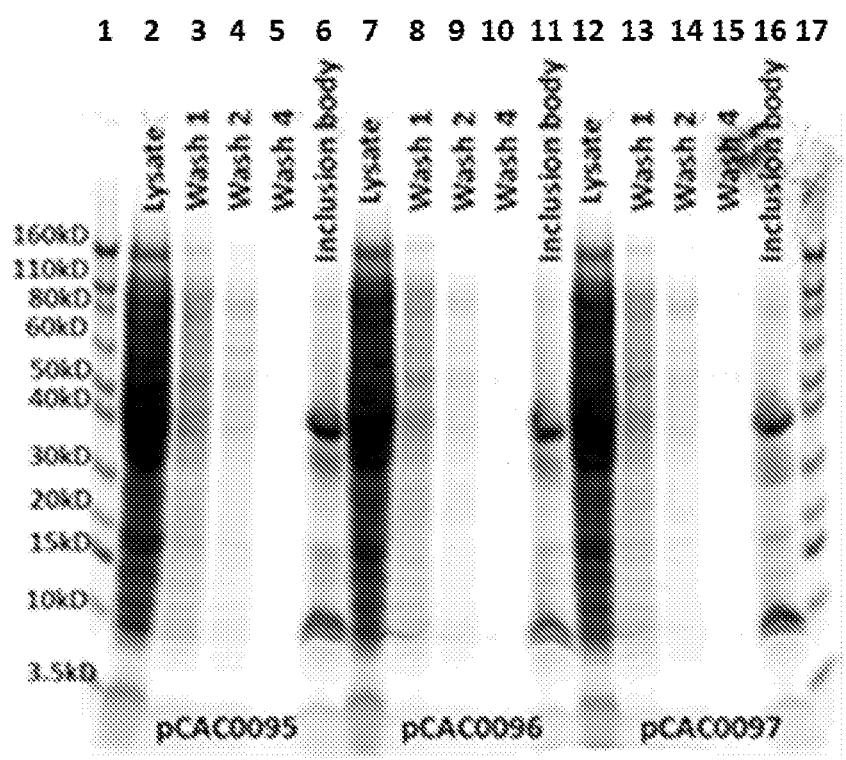
FIG. 8. shows a SDS-PAGE gel of relaxin and relaxin mutants.
Figure 9:
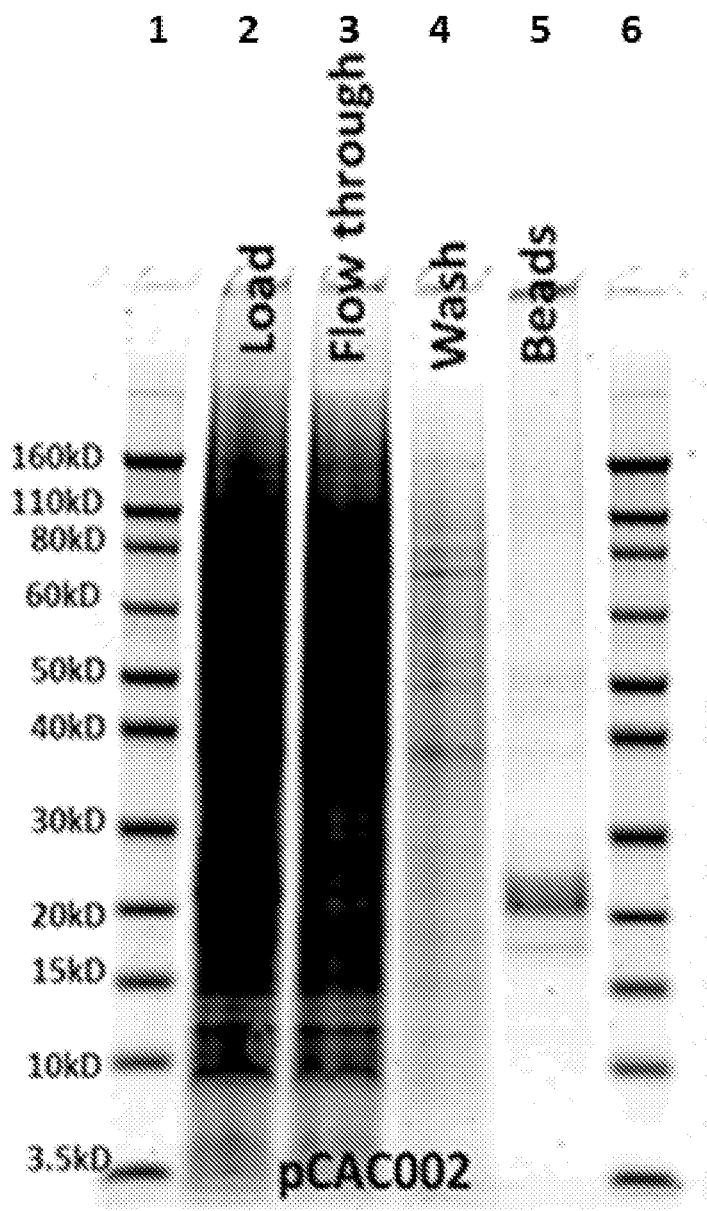
FIG. 9. shows a SDS-PAGE gel of wild type relaxin with CBD tag at the N-terminus.

Relaxin or modified relaxin peptides were expressed through transient transfections of free style HEK293 cells with nucleotide vectors encoding such peptides. Expressed peptides were secreted into the culture medium and harvested at 48 and 96 hours after transfection. The fusion proteins were purified by Protein A/G chromatography (Thermo Fisher Scientific, IL), and analyzed by SDS-PAGE gel. FIG. 8 shows an SDS-PAGE gel of expression of relaxin and relaxin mutants. As shown in FIG. 8, Lanes 1 and 17 show protein standards; Lanes 2-6 show pCAC0095 lysate, Wash 1, Wash 2, Wash 4 and Inclusion Body, respectively; Lanes 7-11 show pCAC0096 lysate, Wash 1, Wash 2, Wash 4 and Inclusion Body, respectively; and Lanes 12-16 show pCAC0097 lysate, Wash 1, Wash 2, Wash 4 and Inclusion Body, respectively. PCAC0095 represents wild type relaxin with GGGRGG (SEQ ID NO: 69) linker and N-terminus 8×His (SEQ ID NO: 70). PCAC0096 represents S26C relaxin with GGGRGG (SEQ ID NO: 69) linker and N-terminus 8×His (SEQ ID NO: 70). PCAC0097 represents S29C relaxin with GGGRGG (SEQ ID NO: 69) linker and N-terminus 8×His (SEQ ID NO: 70). As shown in FIG. 9, Lanes 1 and 6 show protein standards; Lanes 2-5 show pCAC002 Load, Flowthrough, Wash and Beads, respectively. PCAC002 represents wild type relaxin with CBD tag at the N-terminus.

Example 2. Measuring Bioactivity of Relaxin Peptides

Relaxin 2 signals through leucine-rich repeat-containing GPCRs (i.e. LGR7 (RFXR1)). The bioactivity of wild-type relaxin peptides was determined based on the stimulation of adenylate cyclase activity in HEK293T cells stably expressing recombinant LGR7. Stable LGR7 expressing cells were maintained in Dulbecco's modified Eagle's medium/F-12 media supplemented with 200 ng/ml Zeocin (Invitrogen). A cyclic AMP responsive element driven luciferase (CRE-Luc) reporter line was generated by lentiviral transduction of these LGR7 expressing HEK293T cells with CRE-Luc lentivirus (Qiagen) and selected with puromycine (2 μg/mL) for two weeks. A reporter gene assay was used to detect cAMP levels and LGR7 activation by relaxin.

Assay detail: HEK293T cells expressing LGR7 and CRE-Luc are seeded at a density of 5×10$^3$ cells per well in 50 μl of Dulbecco's modified Eagle's medium/F-12 medium containing 10% FBS in 384-well solid bottom white plates. Cells are pre-incubated at 37° C. for overnight. Different concentrations of relaxin peptides (from 0.01 nM to 1000 nM) were added in triplicate, incubated for 18 hours and luciferase activity was detected by adding 104 of Bright Glo (Promega). Luminescence was recorded on Envision (Perkin Elmer). EC$_{50}$ is calculated after non-linear curve fitting (see FIG. 3 for relaxin H2 dose response curve). Select data is shown in Tables 2 and 3.

Example 3. Synthesis of Pegylated Lipid (Amide Linkage) Conjugated Relaxin (Scheme A)

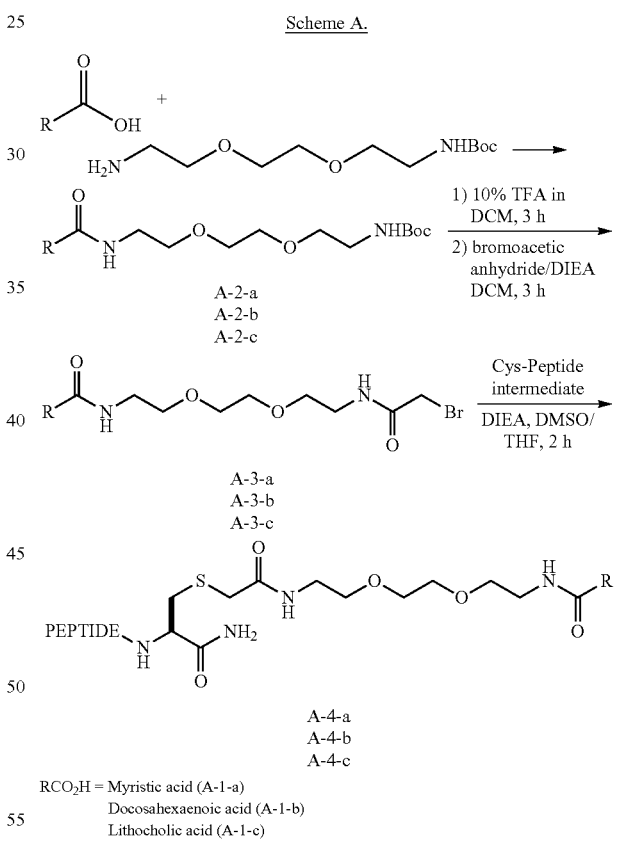

tert-Butyl (2-(2-(2-tetradecanamidoethoxy)ethoxy) ethyl)carbamate (A-2-a)

N-t-Boc-amido-dPEG3-amine (0.5 g, 2.0 mmol) was added to a solution of myristic acid (0.46 g, 2.0 mmol) in 10 ml of dry DMF, followed by HATU (0.8 g, 2.1 mmol) and DIEA (0.45 mL, 2.4 mmol). The mixture was stirred at RT for 6 h and the solvent was evaporated in vacuo. The crude material was dissolved in EtOAc, washed with cold 1% HCl, saturated NaHCO₃ and brine, dried over Na₂SO₄, filtered and concentrated. The crude material was purified by flash column chromatography on silica gel with a gradient 25-50% EtOAc in hexanes to afford 0.83 g of desired compound as white solids (Yield 90%). m/z (ESI+) 459.6 (M+H).

tert-Butyl (2-(2-(2-((4Z,7Z,10Z,13Z,16Z,19Z)-docosa-4,7,10,13,16,19-hexaenamido)ethoxy)ethoxy)ethyl)carbamate (A-2-b)

The title compound was prepared using analogous conditions as the procedure for A-2-a, using N-t-Boc-amido-dPEG3-amine (0.25 g, 1.0 mmol), docosahexaenoic acid (0.33 g, 1.0 mmol), HATU (0.41 g, 1.1 mmol) and DIEA (0.22 mL, 1.2 mmol in dry DMF (5 mL). Yield 68%, brown oil. ¹H NMR (500 MHz; CDCl₃): δ 0.97 (t, J=6.0 Hz, 3H), 1.44 (s, 9H), 2.07 (t, J=5.0 Hz, 2H), 2.25 (J=5.0 Hz, 2H), 2.41 (dd, J=5.0, 6.5 Hz, 2H), 2.79-2.87 (m, 10H), 3.32 (t, J=5.5 Hz, 2H), 3.45 (dd, J=5.0, 6.0 Hz, 2H), 3.55 (t, J=5.0 Hz, 4H), 3.59-3.62 (m, 4H), 4.97 (s, 1H), 5.30-5.42 (m, 12H), 6.03 (s, 1H); m/z (ESI+) 459.6 (M+H).

tert-Butyl (2-(2-(2-((R)-4-((3R,5R,8R,9S,10S,13R,14S,17R)-3-hydroxy-10,13-dimethylhexadecahydro-1H-cyclopenta[a]phenanthren-17-yl)pentanamido)ethoxy)ethoxy) ethyl)carbamate (A-2-c)

N-t-Boc-amido-dPEG3-amine (0.14 g, 0.55 mmol) was added to a solution of NHS-activated lithocholic acid ester (0.24 g, 0.5 mmol) in 5 ml of dry DMF, followed by DIEA (0.18 mL, 1.0 mmol). The mixture was stirred at RT for 16 h, and the solvent was evaporated in vacuo. The crude material is dissolved in DCM, washed with cold 1% HCl, saturated NaHCO₃ and brine, dried over Na₂SO₄, filtered and concentrated. The crude material was purified by flash column chromatography on silica gel with a gradient 1-5% methanol in DCM to afford 0.48 g of desired compound as a white solid (Yield 80%). ¹H NMR (500 MHz; CDCl₃): δ 0.62 (s, 3H), 0.90-2.25 (m, 30H), 3.31 (s, 2H), 3.43-3.46 (s, 2H), 3.52-3.56 (m, 4H), 3.59-3.60 (m, 6H), 4.94 (s, 1H), 6.05 (s, 1H); m/z (ESI+) 628.6 (M+H) m/z (ESI+) 607.5 (M+H).

N-(2-(2-(2-(2-Bromoacetamido)ethoxy)ethoxy) ethyl)tetradecanamide (A-3-a)

TFA (2 ml, 26 mmol) was added to a solution of A-2-a (0.46 g, 1 mmol) in 10 ml of DCM, and the mixture was stirred at RT for 3 h. The reaction mixture was concentrated, and the crude material was lyophilized to obtain a colorless oil that was dissolved in 10 ml of DCM. Bromoacetic anhydride (0.31 g, 1.2 mmol) was added, followed by DIEA (0.52 ml, 2.5 mmol), and the mixture was stirred at RT for 3 h. The reaction mixture was extracted with DCM and EtOAc, washed with 1% HCl, saturated NaHCO₃ and brine, dried over Na₂SO₄, filtered and concentrated. The crude material was purified by flash column chromatography on silica gel with a gradient 20-50% EtOAc in petroleum ether with 5% methanol to obtain 0.37 g of desired compound as a white solid (combined yield over two steps, 78%). ¹H NMR (500 MHz; CDCl₃): δ 0.88 (t, J=6.5 Hz, 3H), 1.25-1.32 (m, 20H), 1.62 (t, J=7.5 Hz, 2H), 2.18 (t, J=8.0 Hz, 2H), 3.47 (dd, J=5.0, 10.0 Hz, 2H), 3.50 (dd, J=5.0, 10.0 Hz, 2H), 3.56-3.58 (m, 2H), 3.59-3.62 (m, 2H), 3.63 (d, J=5.5 Hz, 5H), 3.88 (s, 2H), 5.92-5.93 (m, 1H), 6.94 (s, 1H); 7.04-7.17 (m, 1H); 13C NMR (100 MHz; CDCl3): δ 14.55, 23.12, 26.20, 29.76, 29.79, 29.95, 30.06, 30.08, 30.09, 30.11, 32.35, 37.23, 69.84, 70.46, 70.83 (2), 166.06, 173.84; m/z (ESI+) 480.6 (M+H).

(4Z,7Z,10Z,13Z,16Z,19Z)-N-(2-(2-(2-(2-bromoacetamido)ethoxy)ethoxy)ethyl) docosa-4,7,10,13,16,19-hexaenamide (A-3-b)

The title compound was prepared using analogous conditions as the procedure for A-3-a. Yield 67%, brown oil. ¹H NMR (500 MHz; CDCl₃): δ 0.96 (t, J=5.0 Hz, 3H), 2.07 (q, J=7.6 Hz, 2H), 2.23 (J=7.2 Hz, 2H), 2.40 (dd, J=7.2, 13.8 Hz, 2H), 2.79-2.84 (m, 10H), 3.44-3.51 (m, 4H), 3.55-3.62 (m, 4H), 3.63 (s, 4H), 3.88 (s, 2H), 5.78-5.42 (m, 12H), 5.94 (s, 1H), 6.92 (s, 1H); m/z (ESI+) 559.8 (M+H).

(R)-N-(2-(2-(2-(2-bromoacetamido)ethoxy)ethoxy) ethyl)-4-((3R,5R,8R,9S,10S,13R,14S,17R)-3-hydroxy-10,13-dimethylhexadecahydro-1H-cyclopenta [a]phenanthren-17-yl)pentanamide (A-3-c)

The title compound was prepared using analogous conditions as the procedure for A-3-a, replacing A-2-a with A-2-c. Yield 87%, white solid. ¹H NMR (500 MHz; CDCl₃): δ 0.83 (t, J=4.0 Hz, 3H), 0.85-0.94 (m, 6H), 1.00-1.91 (m, 28H), 3.41-3.64 (m, 12H), 3.85-3.88 (m, 2H), 4.86-4.94 (m, 1H), 6.05 (t, J=7.2 Hz, 1H), 7.04 (s, 1H); m/z (ESI+) 628.6 (M+H).

Synthesis of Peptides Derivatized with Fatty Acid or Bile Acid (A-4-a, A-4-b, or A-4-c)

The Cys peptide intermediate (1 equiv) is dissolved in DMSO and is reacted with any one of A-3-a, A-3-b, or A-3-c (2 equiv) dissolved in THF, followed by addition of DIEA (3% by volume). Reaction completion is assessed by HPLC-MS. The reaction is quenched by addition of TFA to a final pH of 4, and directly purified by preparative reverse-phase HPLC using eluents (A) 0.05% TFA in water and (B) 0.05% TFA in acetonitrile, and the following gradient for eluent (B): 10% (1 min) 40-55% (10 min), flow rate 80 ml/min. The purified peptides are lyophilized, and structure and purity are confirmed by analytical HPLC and electrospray mass spectrometry.

Example 4. Synthesis of Pegylated Lipid (Ether Linkage) Conjugated Relaxin (Schemes B-1 and B-2)

Scheme B-1

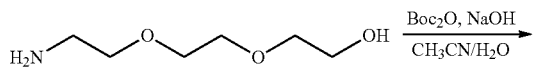

-continued

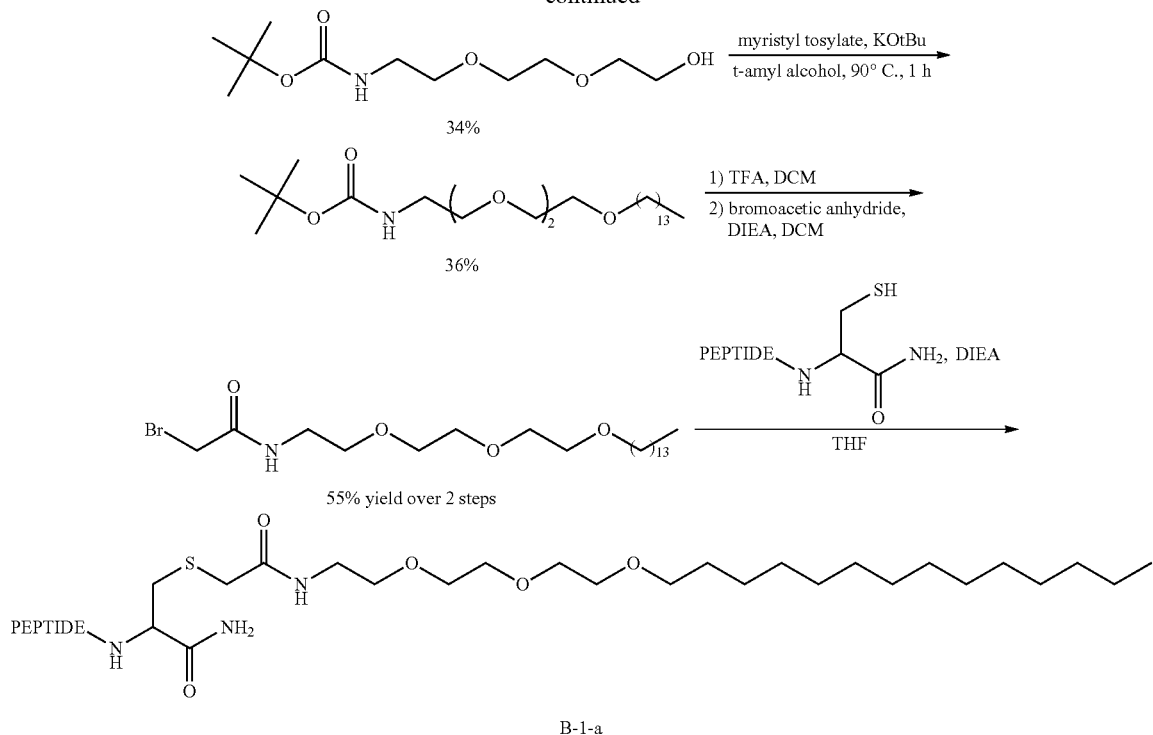

B-1-a

A solution of 2-(2-(2-aminoethoxy)ethoxy)ethanol (100 mg, 0.671 mmol, 89 μL) in 4.8 mL of acetonitrile/water (6:1) was treated with di-tert-butyl dicarbonate (151 mg, 0.691 mmol), followed by 0.5 mL of 1 N NaOH (aq). After stirring at RT for 45 min, the organic solvent was removed in vacuo, the residue was dissolved in saturated NH$_4$Cl (aq), and the desired carbamate was extracted with EtOAc. Removal of EtOAc provided 57 mg (34% yield) of tert-butyl 2-(2-(2-hydroxyethoxy)ethoxy)ethylcarbamate as a colorless oil.

A solution of tert-butyl 2-(2-(2-hydroxyethoxy)ethoxy)ethylcarbamate (68.5 mg, 0.275 mmol) and myristyl tosylate (101 mg, 0.275 mmol) in 1.4 mL of t-amyl alcohol was treated with potassium tert-butoxide (61.6 mg, 0.550 mmol) and potassium iodide (4.6 mg, 0.028 mmol). After heating to 90° C. for 2 h, the reaction was allowed to cool to rt, quenched with saturated NH$_4$Cl (aq), then extracted with EtOAc and dried over Na$_2$SO$_4$. Concentration and subsequent purification via flash column chromatography on silica gel afforded 44 mg (36% yield) of tert-butyl 2-(2-(2-(tetradecyloxy)ethoxy)ethoxy)ethylcarbamate as a colorless oil.

A solution of tert-butyl 2-(2-(2-(tetradecyloxy)ethoxy)ethoxy)ethylcarbamate (26 mg, 0.058 mmol) in 1.2 mL of DCM was treated with 0.29 mL of trifluoroacetic acid. After stirring at rt for 50 min, the mixture was concentrated and re-dissolved in 2 mL DCM. A 1-mL aliquot of this solution was taken into a separate vial, which was cooled to 0° C. and subsequently charged with bromoacetic anhydride (10.3 mg, 0.040 mmol) and DIEA (11 μL, 0.063 mmol). After stirring at rt for 12 h, the reaction mixture was purified via flash column chromatography to provide 7.5 mg (55% yield over 2 steps) of 2-bromo-N-(2-(2-(2-(tetradecyloxy)ethoxy)ethoxy)-ethyl)acetamide as an off-white solid.

A solution of the Cys-peptide intermediate (1 equiv) in DMSO (4 mM) is treated with 2-bromo-N-(2-(2-(2-(tetradecyloxy)ethoxy)ethoxy)-ethyl)acetamide (2.1 equiv) in THF (5.4 mM) and DIEA (114 equiv). Upon reaction completion, the reaction mixture is purified by preparative reverse-phase HPLC to provide the lipid conjugate (B-1-a).

Scheme B-2

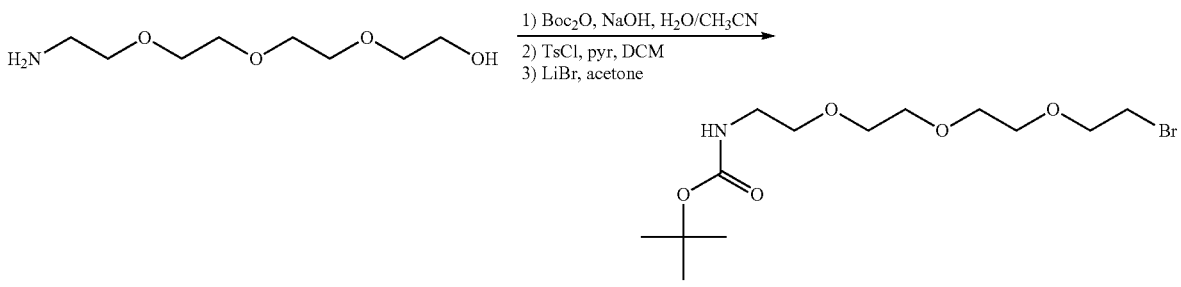

B-2-a

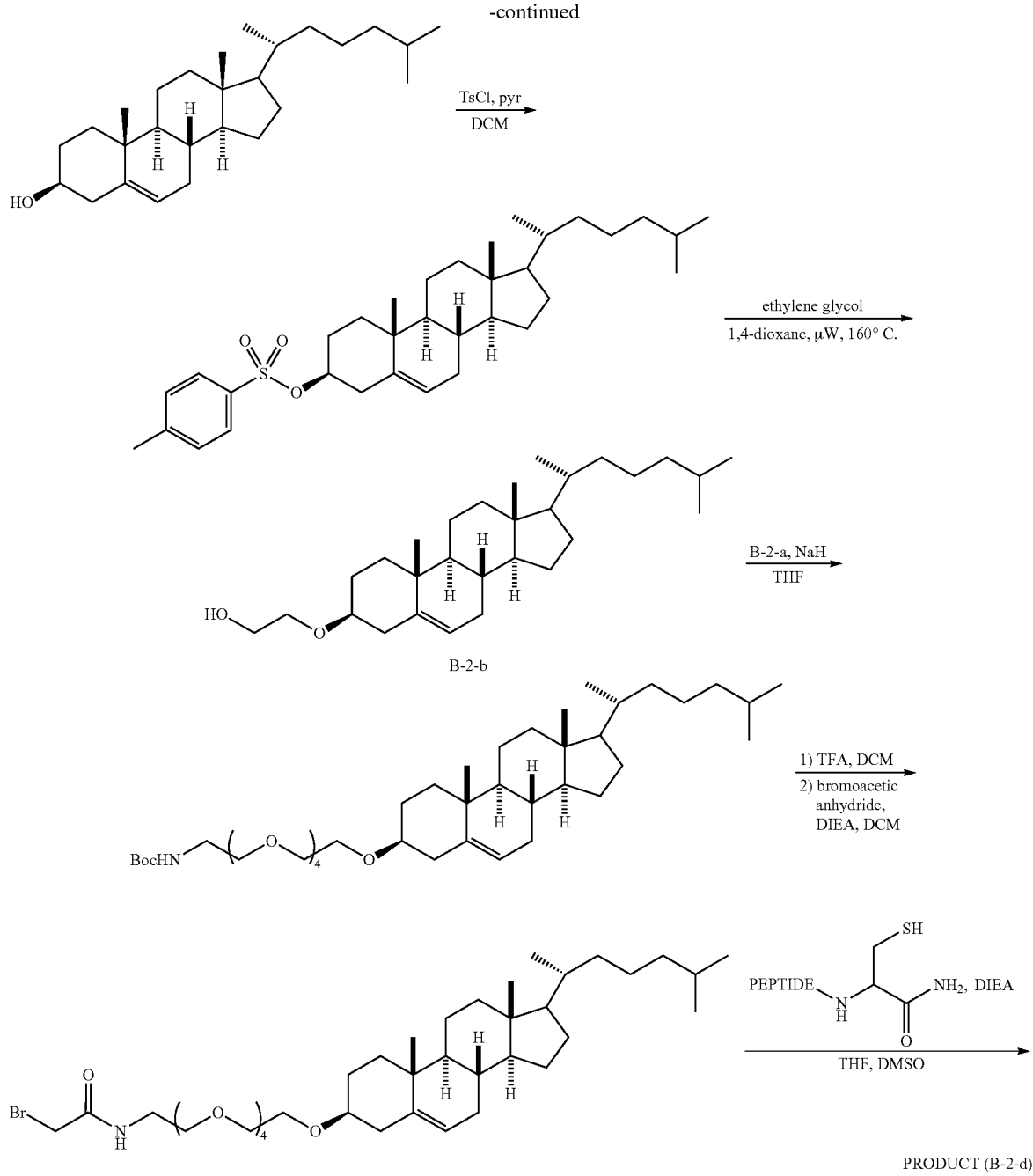

PRODUCT (B-2-d)

tert-Butyl 2-(2-(2-(2-bromoethoxy)ethoxy)ethoxy) ethylcarbamate (B-2-a)

A solution of 2-(2-(2-(2-aminoethoxy)ethoxy)ethoxy) ethanol (400 mg, 2.07 mmol, 0.33 mL) in 15 mL of acetonitrile/water (6:1) was treated with di-tert-butyl dicarbonate (603 mg, 2.77 mmol), followed by 2.8 mL of 1 N NaOH (aq). After stirring at RT for 45 min, the organic solvent was removed in vacuo, the residue was dissolved in saturated NH₄Cl (aq), and the desired carbamate was extracted with EtOAc. Removal of EtOAc provided the crude carbamate as a colorless oil.

This oil was dissolved in DCM and treated with p-toluenesulfonyl chloride (1.18 g, 6.21 mmol) and pyridine (0.84 mL, 10.4 mmol). After stirring at 40° C. for 12 h, the mixture was diluted with DCM and washed with 1N HCl (2×10 mL), H₂O (10 mL), and brine (10 mL), then dried over Na₂SO₄ and concentrated. Purification via flash column chromatography on silica gel gave 330 mg (36% yield over 2 steps) of the tosylate as a colorless oil.

A solution of the tosylate (203 mg, 0.453 mmol) in 3.1 mL of anhydrous acetone was treated with LiBr (385 mg, 4.53 mmol). After stirring at 60° C. for 8 h, the solvent was removed and the resulting residue was dissolved in EtOAc. The organic mixture was washed with water, dried over MgSO₄, filtered, and concentrated. Purification via flash column chromatography on silica gel gave 126 mg (78% yield) of the title compound as a colorless oil.

2-((3S,8S,9S,10R,13R,14S,17R)-10,13-Dimethyl-17-(6-methylheptan-2-yl)-2,3,4,7,8,9,10,11,12,13,14,15,16,17-tetradecahydro-1H-cyclopenta[a]phenanthren-3-yloxy)ethanol (B-2-b)

A solution of cholesterol (1.50 g, 3.89 mmol) in 4 mL of DCM was treated with p-toluenesulfonyl chloride (1.49 g, 7.78 mmol), pyridine (4 mL), and DMAP (94.9 mg, 0.780 mmol). After stirring at RT for 12 h, the mixture was diluted with DCM and washed with 1N HCl (2×5 mL), H₂O (5 mL), and brine (5 mL), then dried over Na₂SO₄ and concentrated in vacuo. Recrystallization from chloroform and methanol gave 1.66 g (79% yield) of the tosylate intermediate as a white solid.

A microwave vial charged with the tosylate intermediate (500 mg, 0.926 mmol) in 7.7 mL of 1,4-dioxane was treated with 2.6 mL of ethylene glycol. After heating to 160° C. by microwave irradiation for 10 min, the solvent was removed, and the residue was dissolved in chloroform and washed with saturated NaHCO₃ (5 mL), H₂O (5 mL), and brine (5 mL), then dried over Na₂SO₄ and concentrated in vacuo. Purification of the crude material by flash column chromatography using silica gel provided 270 mg (68% yield) of the title compound as a white solid.

2-Bromo-N-(14-((3S,8S,9S,10R,13R,14S,17R)-10,13-dimethyl-17-(6-methylheptan-2-yl)-2,3,4,7,8,9,10,11,12,13,14,15,16,17-tetradecahydro-1H-cyclopenta[a]phenanthren-3-yloxy)-3,6,9,12-tetraoxatetradecyl)acetamide (B-2-c)

A solution of B-2-b (219 mg, 0.509 mmol) in 2.5 mL of THF was treated with sodium hydride (60% dispersion in mineral oil, 20.4 mg, 0.509 mmol) and stirred for 30 min. The mixture was cooled to 0° C. and treated with B-2-a (139 mg, 0.392 mmol) in 2.5 mL of THF. After heating to 40° C. for 6 h, the reaction was quenched with saturated NH₄Cl (aq) and extracted with EtOAc. Purification of the crude material by flash column chromatography using silica gel provided 101 mg (36% yield) of the ether intermediate as a colorless oil.

A solution of the ether intermediate (74 mg, 0.105 mmol) in 2.1 mL of DCM was treated with 0.53 mL of TFA. After stirring at RT for 40 min, the mixture was concentrated in vacuo and dissolved in 10 mL DCM. A 4-mL aliquot of this solution was taken into a separate vial, concentrated to a 1-mL volume, cooled to 0° C., and charged with bromoacetic anhydride (13.6 mg, 0.053 mmol) and DIEA (15 μL, 0.088 mmol). After stirring at RT for 12 h, the reaction mixture was directly purified by flash column chromatography using silica gel to give 12.6 mg (41% over 2 steps) of the title compound as an colorless oil.

Lipid conjugate B-2-d is prepared in an analogous manner as lipid conjugate B-1-a of Example 4, Scheme B-1.

Example 5. Preparation of Br-FA₁

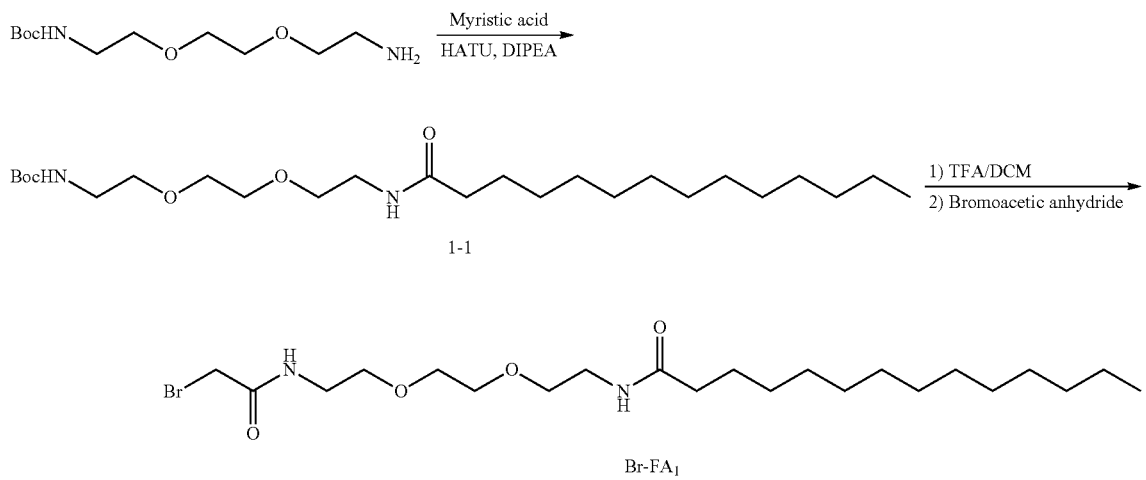

Step A. Tert-butyl (2-(2-(2-tetradecanamidoethoxy)ethoxy)ethyl)carbamate (1-1)

Myristic acid (0.46 g, 2 mmol) was dissolved in 5 mL of DMF. HATU (0.8 g, 2.1 mmol) and DIPEA (0.4 mL, 2.2 mmol) were added followed by the addition of Boc-NH-PEG2-COOH (0.5 g, 2 mmol). The reaction mixture was then stirred for 6 h, and the solvent was removed. The product was extracted with EtOAc (3×15 mL). The organic layer was successively washed with sat. NaHCO₃, cooled HCl (1 M) and brine, dried over Na₂SO₄, filtered, and concentrated. Purification by flash column chromatography on silica gel provided 0.81 g of desired compound as white solids in 90% product yield. ESI-MS: calcd MW 458.4. found 459.6 [M+1]⁺.

Step B. N-(2-(2-(2-(2-bromoacetamido)ethoxy)ethoxy)ethyl)tetradecanamide (Br-FA₁)

A solution of 1-1 (0.23 g, 0.5 mmol) in DCM (10 mL) was treated with TFA (2 mL) for 2 h. The mixture was concentrated and followed by the addition of bromoacetic anhydride (0.14 g, 0.55 mmol), DIPEA (0.17 mL, 1 mmol) in 10 mL of DCM at 0° C. The reaction mixture was then stirred for 2 h, and the solvent was removed. The product was extracted with EtOAc (3×15 mL). The organic layer was successively washed with sat. NaHCO₃, cooled HCl (1 M) and brine, dried over Na₂SO₄, filtered, and concentrated. Purification by flash column chromatography on silica gel provided 0.2 g of the title compound as white solids in 83% product yield. ESI-MS: calcd MW 479.5. found 480.4 [M+1]⁺.

Example 6. Solid-Phase Synthesis of Br-FA₂

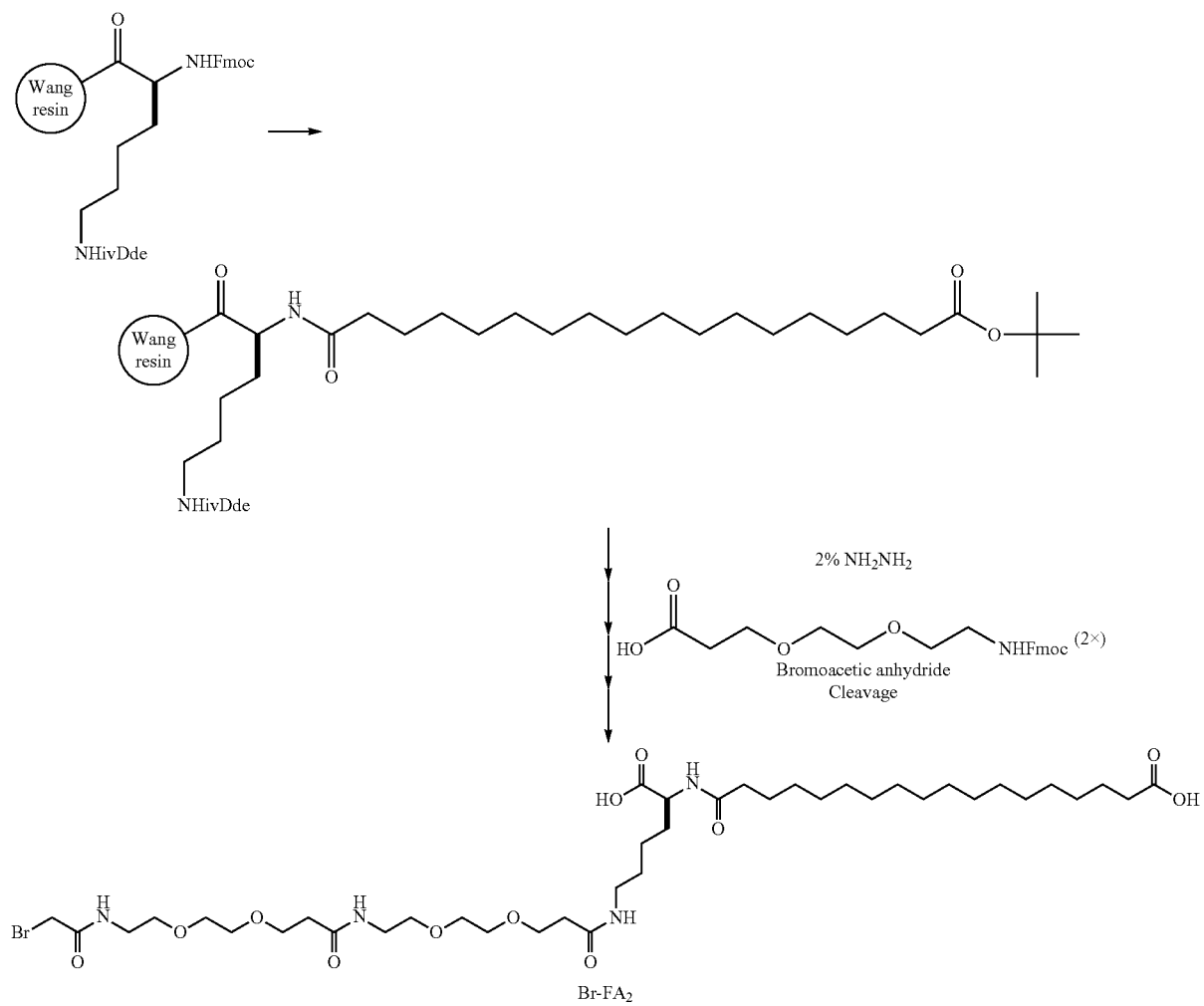

Fmoc-Lys(ivDde)-OH (60 mg, 100 µmol) was attached to 2-chlorotrityl chloride resin (Novabiochem) (100 mg, 80 µmol) by mixing the amino acid, the resin, and DIPEA (70 µL, 400 µmol) in 5 mL of DMF and stirring for 30 min. The resin was then washed with DMF (3×), DCM (3×) and treated with CH₃OH/DCM/DIPEA (8:1:1) for 10 min to cap the unreacted trityl chloride sites, dried under vacuum, and stored in a desiccator.

To this resin (50 mg, 40 µmol) was added piperidine in DMF (20%, 5 mL). The mixture was shaken for 1 min and drained. Another 5 mL of 20% piperidine was added and this time the mixture was shaken for 15 min. Positive ninhydrin test was observed. The resin was then washed as described above.

The resin was then treated with octadecanedioic acid mono-tert-butyl ester (AstaTech) (74 mg, 200 µmol) using coupling reagent HATU (76 mg, 200 µmol), and DIPEA (35 µL, 200 µmol) in DMF (5 mL) for 2 h or repeated until a negative ninhydrin test was observed. After washing with DMF and DCM, the resin was treated with 2% hydrazine in DMF (5 mL, 2×5 min). Positive ninhydrin test was observed. The resin was then washed as described above.

The resin was then treated with Fmoc-PEG2-propionic acid (Quanta BioDesign) (80 mg, 200 µmol) using HATU (76 mg, 200 µmol), and DIPEA (35 µL, 200 µmol) in DMF (5 mL) for 2 h or repeated until a negative ninhydrin test was observed. The resin was then washed as described above. Then the protecting group is removed and the above steps are repeated.

The resin was then treated with bromoacetic anhydride (55 mg, 200 µmol), and DIPEA (35 µL, 200 µmol) in 2 mL of DCM and stirring for 30 min. After washing with DCM (3×), the product was cleaved from the resin using 5 mL of 10% TFA in DCM containing 10% H₂O and 10% triisopropylsilane for 1 h. After cleavage, TFA was removed under reduced pressure. The resulting yellow residue was washed several times with cold diethyl ether and was finally dried to a crude product as yellow powder under nitrogen flow.

Attempts to dissolve 50 mg of the crude product in up to 0.5 mL of 50% CH₃CN in water (0.1% TFA) have been unsuccessful. Therefore, as an alternative, the crude peptide, (50 mg) was dissolved in DMSO (0.1 mL) and this solution was diluted to a final volume of 0.5 mL with 50% CH₃CN-water. The solution was filtered. The filtered solution was loaded onto the preparative HPLC column (Phenomenex, Prep C18, 300A, 50×250 mm) equilibrated with 10% CH₃CN (0.1% TFA) in water (0.1% TFA), and the column was eluted with 10% CH$_3$CN (0.1% TFA) in water (0.1% TFA) to wash DMSO from the column. The composition of the eluent then was ramped to 35% CH$_3$CN-water (0.1% TFA) over 1 min, and a linear gradient was initiated at a rate of 0.5%/min of CH$_3$CN (0.1% TFA) into water (0.1% TFA) and run for 50 min. Eluted fractions were checked for purity on an analytical reversed phase C18 column (Phenomenex, C18, 120A, 4.6×50 mm) and fractions containing the product in >95% purity were combined and freeze-dried to afford the title compound (15 mg, 41% yield). The molecular weight of product was analyzed by ESI-MS: calcd MW 880.9. found 881.3 [M+1]$^+$, 882.6 [M+2]$^+$.

Example 7. Solid-Phase Synthesis of Br-FA$_3$

Example 8. Preparation of Br-FA$_4$

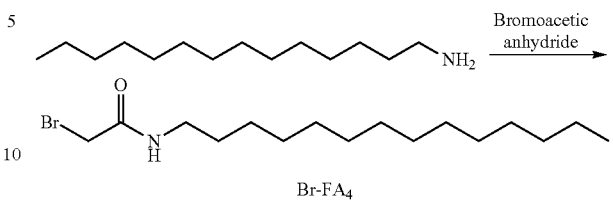

A solution of tetradecylamine (107 mg, 0.5 mmol) in DCM (10 mL) was treated with bromoacetic anhydride

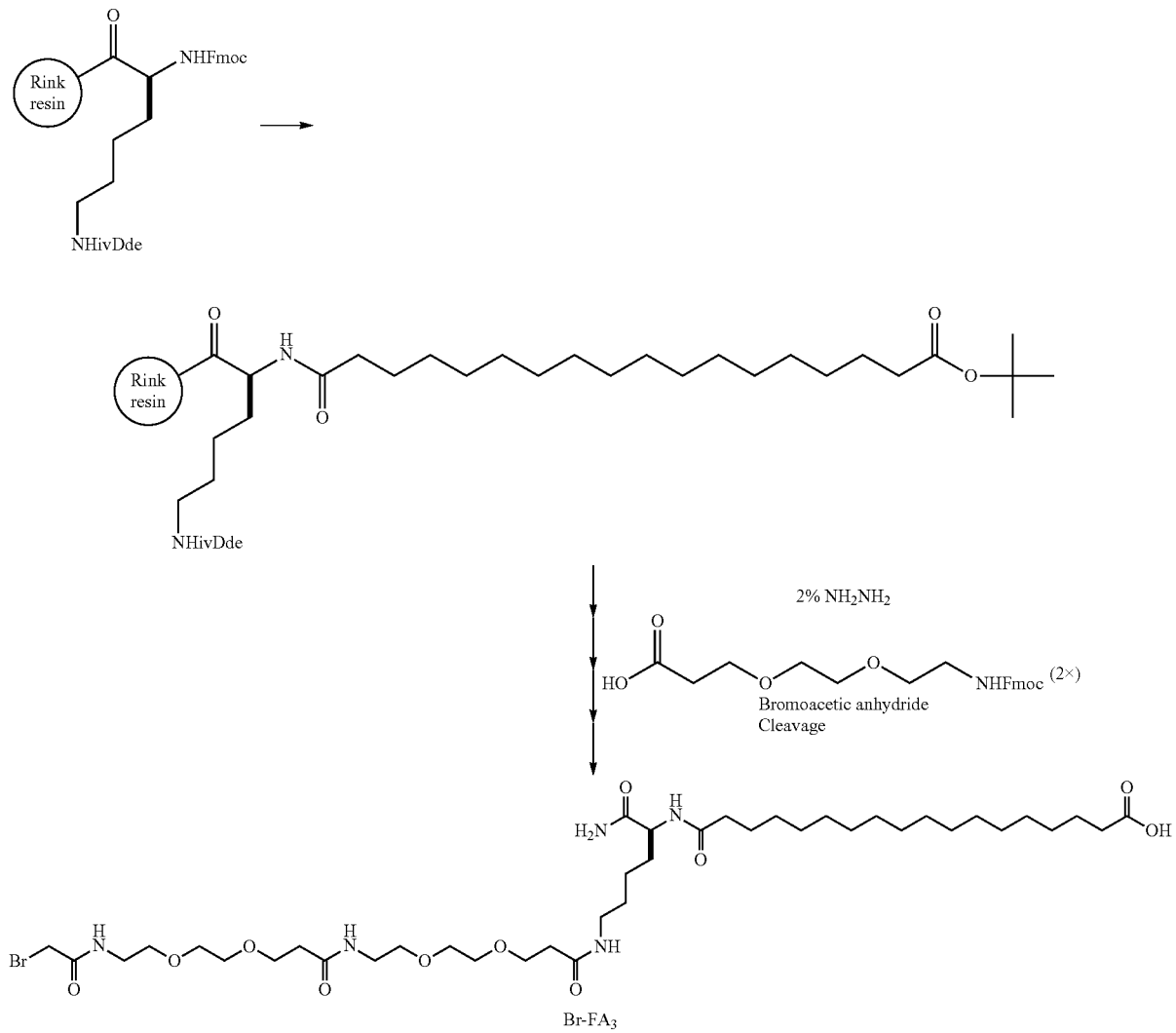

The title compound was prepared in an analogous manner as Br-FA$_2$ by substituting 2-chlorotrityl chloride resin with rink amide resin. Purification by preparative HPLC and lyophilization gave the title compound as a white powder with greater than 95% purity in about 45% product yield. The molecular weight of peptide was analyzed by ESI-MS: calcd MW 881.0. found 882.2 [M+1]$^+$, 883.7 [M+2]$^+$.

(0.14 g, 0.55 mmol), DIPEA (100 μL, 0.55 mmol) at 0° C. The reaction mixture was then stirred for 2 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 145 mg of the title compound as white solids in 87% product yield. ESI-MS: calcd MW 334.3. found 335.6 [M+1]$^+$.

Example 9. Preparation of Br-FA₅

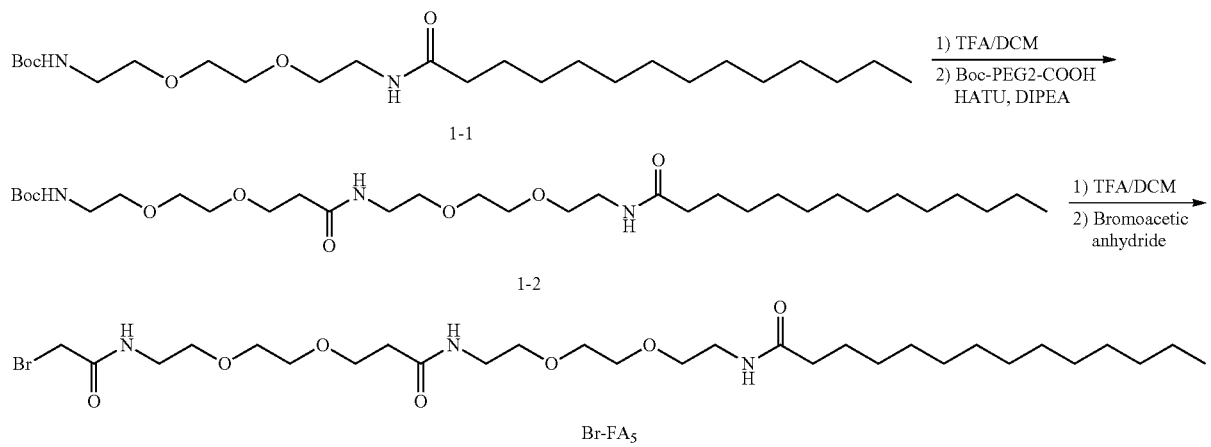

Step A. Tert-butyl (9,20-dioxo-3,6,13,16-tetraoxa-10,19-diazatritriacontyl)carbamate (1-2)

A solution of 1-1 (115 mg, 0.25 mmol) in DCM (10 mL) was treated with TFA (2 mL) for 2 h. The mixture was concentrated and followed by the addition of Boc-NH-PEG2-acid (70 mg, 0.25 mmol), HATU (95 mg, 0.25 mmol) and DIPEA (90 µL, 0.5 mmol) in 5 mL of DMF. The reaction mixture was then stirred for 2 h, and the solvent was removed. The product was extracted with EtOAc (3×15 mL). The organic layer was successively washed with sat. NaHCO₃, cooled HCl (1 M) and brine, dried over Na₂SO₄, filtered, and concentrated. Purification by flash column chromatography on silica gel provided 122 mg of desired compound as white solids in 77% product yield. ESI-MS: calcd MW 617.9. found 618.4 [M+1]⁺.

Step B. N-(1-bromo-2,12-dioxo-6,9,16,19-tetraoxa-3,13-diazahenicosan-21-yl)tetradecanamide (Br-FA₅)

A solution of 1-2 (122 mg, 0.2 mmol) in DCM (10 mL) was treated with TFA (2 mL) for 2 h. The mixture was concentrated and followed by the addition of bromoacetic anhydride (52 mg, 0.2 mmol), DIPEA (70 µL, 0.4 mmol) in 5 mL of DCM at 0° C. The reaction mixture was then stirred for 2 h, and the solvent was removed. The product was extracted with EtOAc (3×15 mL). The organic layer was successively washed with sat. NaHCO₃, cooled HCl (1 M) and brine, dried over Na₂SO₄, filtered, and concentrated. Purification by HPLC provided 88 mg of the title compound as white solids in 69% product yield. ESI-MS: calcd MW 638.7. found 639.4 [M+1]⁺.

Example 10. Preparation of Br-FA₆

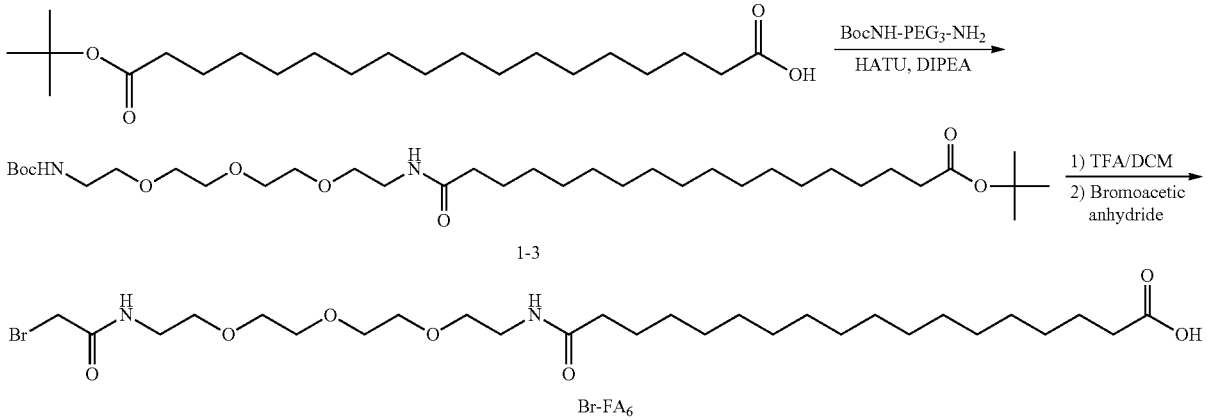

Step A. tert-Butyl (2-(2-(2-tetradecanamidoethoxy)ethoxy)ethyl)carbamate (1-3)

Octadecanedioic acid mono-tert-butyl ester acid (0.18 g, 0.5 mmol) was dissolved in 5 mL of DMF. HATU (0.2 g, 0.55 mmol) and DIPEA (0.1 mL, 0.55 mmol) were added followed by the addition of Boc-NH-PEG3-NH₂ (0.12 g, 0.5 mmol). The reaction mixture was then stirred for 6 h, and the solvent was removed. The product was extracted with EtOAc (3×10 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.28 g of tert-butyl (2-(2-(2-tetradecanamidoethoxy)ethoxy)ethyl)carbamate as white solids in 87% product yield. ESI-MS: calcd MW 644.5. found 645.5 [M+1]$^+$.

Step B. 1-Bromo-2,16-dioxo-6,9,12-trioxa-3,15-diazatritriacontan-33-oic acid (Br-FA$_6$)

A solution of 1-3 (65 mg, 0.1 mmol) in DCM (2 mL) was treated with TFA (4 mL) for 4 h. The mixture was concentrated and followed by the addition of bromoacetic anhydride (26 mg, 0.1 mmol), DIPEA (35 μL, 0.2 mmol) in 5 mL of DCM at 0° C. The reaction mixture was then stirred for 2 h, and the solvent was removed. The product was purified by HPLC provided 35 mg of the title compound as white solids in 70% product yield. ESI-MS: calcd MW 608.3. found 609.4 [M+1]$^+$.

Example 11. Solid Phase Synthesis of Br-FA$_7$

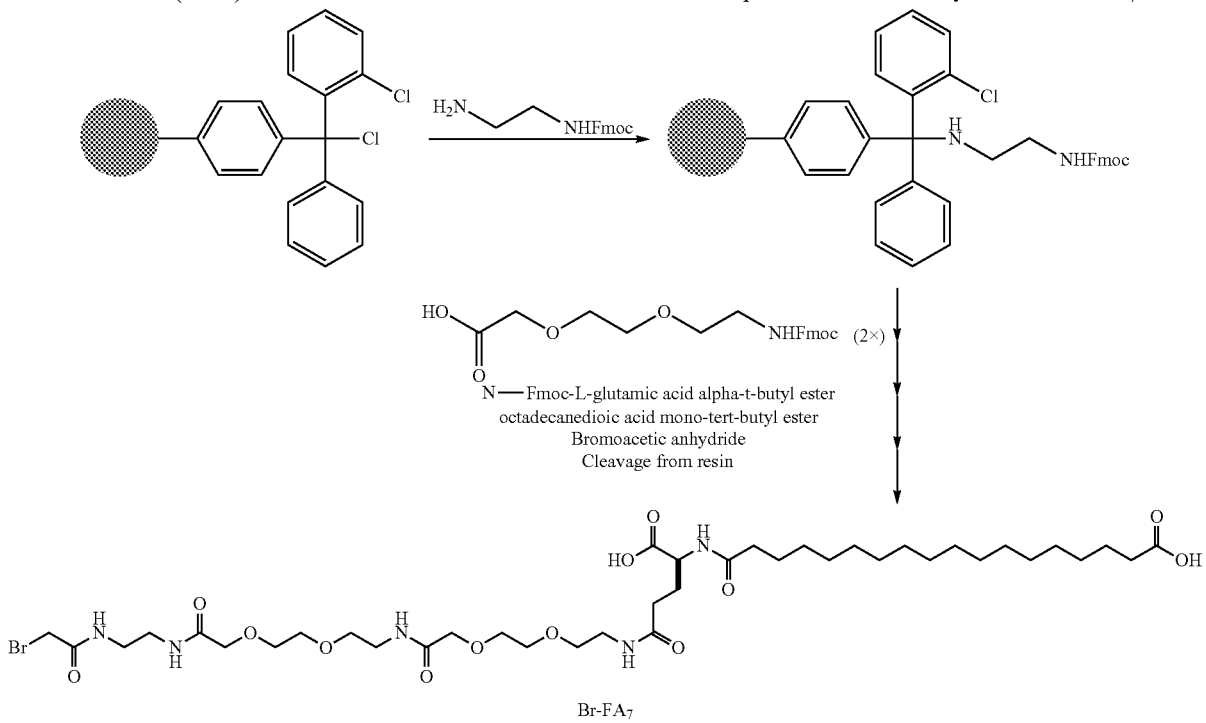

The title compound was prepared in an analogous manner as Br-FA$_2$ by substituting Fmoc-Lys(ivDde)-OH and Fmoc-PEG2-propionic acid with mono-Fmoc ethylene diamine hydrochloride and [2-[2-(Fmoc-amino)ethoxy]ethoxy]acetic acid, respectively. Purification by preparative HPLC and lyophilization afforded the title compound as a white powder with greater than 95% purity in about 25% product yield. The molecular weight of peptide was analyzed by ESI-MS: calcd MW 896.9. found 898.1 [M+1]+.

Example 12. Preparation of Br-FA8

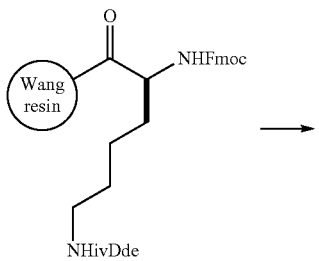

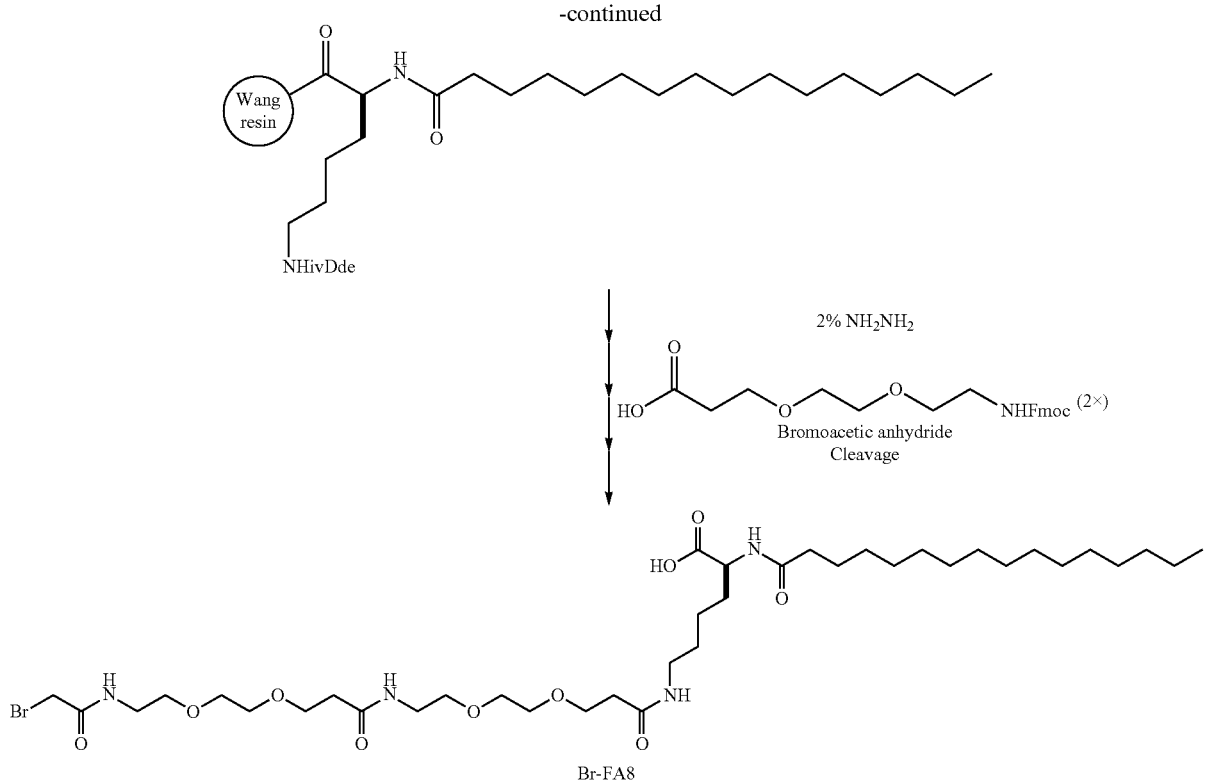

The title compound was prepared in an analogous manner as Br-FA$_2$ by substituting octadecanedioic acid mono-tert-butyl ester with palmitic acid. Purification by preparative HPLC and lyophilization afforded the title compound as a white powder with greater than 95% purity in about 29% product yield. The molecular weight of peptide was analyzed by ESI-MS: calcd MW 822.4. found 823.6 [M+1]$^+$.

Example 13. Preparation of Inclusion Bodies

Cells expressing relaxin analogs were spun down to produce a cell pellet. The cell pellet was re-suspended in lysis buffer (100 mM Tris, pH 8, 100 mM NaCl, 1% Triton-X100, 2 mM EDTA) and lysed by passing through French pressure cell operated at 18,000 psi for at least 3 times while chilling the cell suspension to 4° C. after each pass. Lysed cell suspension was clarified by centrifuging for 45 min at 15,000 rpm, 4° C. The pellet contains intact cells, cellular debris along with inclusion body protein. So the pellet was washed multiple times to isolate the inclusion body protein from the rest, briefly, after decanting the supernatant, the pellet was re-suspended in lysis buffer using a tissue homogenizer and subjected to centrifugation, this procedure was repeated at least thrice. To remove the Triton-X 100 from the pellet, the pellet was washed at least twice with wash buffer (100 mM Tris, pH 8, 100 mM NaCl, 1% Triton-X100, 2 mM EDTA); washing of pellet was performed by resuspension through homogenization followed by centrifugation. The pellet was then directly used for in vitro refolding of the relaxin analog without any further purification.

Example 14. Refolding of Relaxin Analogs

The cell pellet from Example 13 was used for in vitro refolding of relaxin analogs. Refolding of the relaxin analogs was carried using oxidized/reduced glutathione. Inclusion bodies were dissolved in 8M guanidine hydrochloride (GdnHCl). 40 mL of GdnHCl was used to dissolve inclusion body pellet isolated from 1 L E. coli culture. After solubilizing the protein, the insoluble portion was pelleted by centrifuging at 15000 rpm for 30 min. The solubilized protein was then concentrated using 3,000 MW cutoff Amicon Ultra (Fisher Scientific) centrifugal filter unit to 10-15 mL. The denatured protein was then diluted in to 300 mL of refolding buffer (440 mM Arginine, 55 mM Tris, pH 8.2 containing 2 mM GSH, 10 mM GSSG). The refolding was continued for 1-2 hours and quenched by adding TFA to pH 2. The precipitate was then centrifuged to a pellet and the supernatant was transferred in to centrifugal unit and concentrated to 2-3 mg/mL. The concentrated protein mixture was then purified by semi-preparative HPLC using Phenomenex Jupiter C5 column (250×4.6 mm) with the flow rate set at 4.0 mL/min. The fractions were analyzed by LC-MS for the desired protein and then pooled and lyophilized.

Example 15. Conjugation of Lipid to Relaxin

All the enzymatic processing (Trypsin/Cp-B or TEV protease) were performed after capping cysteine, as the free thiol in relaxin was observed to cause scrambling at basic pH where enzymatic digestion are generally performed. The lyophilized protein from Example 14 was dissolved in 0.25% TFA. Pegylated lipid was dissolved in ACN acetonitrile/100 mM NH$_4$HCO$_3$ buffer (1:1), pH 8.5. Relaxin was then added to the mixture and the reaction proceeded at room temperature for 2 hours; the progress of the reaction was checked by LC-MS. After completion of reaction, the mixture was then lyophilized.

Example 16. Enzymatic Conversion of Relaxin Precursor into Two-Chain Precursor The lyophilized powder from Example 15 was resuspended in 50 mM Tris buffer containing 1 mM $CaCl_2$, pH8. Trypsin (1:100) was added to this mixture, and the mixture was incubated for 1 hour at room temperature. After 1 hour, carboxy peptidase-B (10 units for 1 mg of protein) was added in to the mixture and the progress of the cleavage was monitored by LC-MS analysis. After the complete cleavage, the pH of the mixture was brought to 4 by adding acetic acid. The mixture was lyophilized and purified semi-preparative HPLC.

Example 17. Cleavage of His-Tag Through TEV Protease

The lyophilized protein of Example 16 was re-dissolved in PBS buffer containing 3 mM GSH: 0.5 mM GSSG. Tev protease was added in to the mixture and incubated overnight at room temperature. The cleavage of tag was confirmed by LC-MS analysis.

Example 18. Gene Construction and Expression of Toxin-550 Analogs

The inserts were prepared through polymerase cycling assembly, where forward and reverse primers were annealed to generate the DNA fragment which was further enriched by forward and reverse primers. The amplified fragment was then digested with restriction digestion enzymes (Bam I/Hind-III). The prepared insert was then ligated into a vector with a PET backbone, the encoded DNA fragment was then confirmed by DNA sequencing. Toxin-550 constructs (pET/Txin-550) were transformed into E. coli strain BL21 (DE3). The transformed E. coli cells were cultured in terrific broth (with 50 μg/ml kanamycin) to OD600 nm=1.0 at 37° C. with vigorous shaking (250 rpm). To induce expression of the proteins, IPTG stock solution (1M) was added to the final concentration of 0.5 mM, and the cells were continuously incubated with shaking at 250 rpm at 26° C. for 24 h. On the following day, cells were harvested by centrifugation (6000 rpm, 15 min).

Preparation of Inclusion Bodies

A cell pellet was re-suspended in lysis buffer (100 mM Tris, pH 8, 100 mM NaCl, 1% Triton-X100, 2 mM EDTA) and lysed by passing through French pressure cell operated at 18,000 psi for at least 3 times while chilling the cell suspension to 4° C. after each pass. Lysed cell suspension was clarified by centrifuging for 45 min at 15,000 rpm, 4° C. The pellet contained intact cells, cellular debris along with inclusion body protein. The pellet was washed multiple times to isolate the inclusion body protein from the rest of the cells and other cellular debris. Briefly, after decanting the supernatant, the pellet was re-suspended in lysis buffer using a tissue homogenizer and subjected to centrifugation, this procedure was repeated at least thrice. To remove the Triton-X 100 from the pellet, the pellet was washed at least twice with wash buffer (100 mM Tris, pH 8, 100 mM NaCl, 1% Triton-X100, 2 mM EDTA), washing of pellet was performed by suspension through homogenization followed by centrifugation. The pellet was then directly used for in vitro refolding without any further purifications.

Example 19. Refolding of Toxin-550 Analogs

Refolding was carried using oxidized/reduced glutathione. Inclusion bodies (as in Example 18) were dissolved in 8M guanidine hydrochloride (GdnHCl). 10 mL of GdnHCl was used to dissolve the inclusion body pellet isolated from 1 L *E. coli* culture. After solubilizing the protein, another 10 mL of Tris-HCL buffer (50 mM) was added and the insoluble portion was pelleted by centrifuging at 15000 rpm for 30 min. The solubilized supernatant denatured protein was then diluted in to 200 mL of refolding buffer. Various refolding buffers that were used to dilute the solubilized supernatant denatured protein are shown in the table below:

| Refolding Buffer | GSH:GSSG |
|---|---|
| 0.1M Tris, pH 8.2 | 1:10 |
| 0.1M Tris, pH 11 | 1:10 |
| 0.1M $NH_4HCO_3$, pH 8 | 1:10 |
| 0.1M $NH_4OAC$ | 1:10 |
| 2M $NH_4OAC$ | 1:10 |
| 2M $(NH_4)_2SO_4$ | 1:10 |

FIG. 10 shows the disulfide bond pattern for the Toxin-550 peptide (wild-type) and an exemplary in vitro folding pathway of cysteine-knot Toxin-550 peptide, the middle structure depicting a two-sulfide bond intermediate, in which a disulfide bond is formed between cysteine I and cysteine IV and between cysteine II and cysteine V.

Various refolding trails were employed, with most of the refolding buffer conditions leading to a two-disulfide bond intermediate as major product, with the exception of 2 M $(NH_4)_2SO_4$ refolding buffer, where the three disulfide bond product is observed in 4 hours. The three disulfide bond product contains a Toxin-550 peptide with a disulfide bond formed between cysteine I and cysteine IV, between cysteine II and cysteine V, and between cysteine III and cysteine VI.

Example 20. Conjugation of Lipid to Toxin-550

The refolded toxin-550 was then buffer exchanged with PBS, 2% TFA to remove the excess glutathione before conjugation with lipids. Pegylated lipid was dissolved in ACN acetonitrile/100 mM $NH_4HCO_3$ buffer (1:1), pH 8.5. Toxin was then added to the mixture and the reaction proceeded at room temperature for 2 hours; the progress of the reaction was checked by LC-MS. After completion of reaction, the mixture was then lyophilized and purified by RP-HPLC using C18-phenomenex column. The lipid conjugates comprising a lipid attached to toxin-550 are shown in FIG. 16B as entries 11-13. The brackets depict the disulfide bonds formed between cysteine residues in the lipid conjugates Example 21. Conjugation of Lipid to Oxyntomodulin and Exenatide Derivatives The oxyntomodulin Cys38 (e.g., Oxm-Cys38, SEQ ID NO: 24) and exenatide Cys40 (e.g., Ex4-Cys40, SEQ ID NO: 25) were chemically synthesized using solid-phase peptide synthesis. Pegylated lipid was dissolved in ACN acetonitrile/100 mM $NH_4HCO_3$ buffer (1:1), pH 8.5. The cysteine mutant was dissolved in ACN acetonitrile/100 mM $NH_4HCO_3$ buffer and then added to the pegylated lipid mixture and the reaction proceeded at room temperature for 2 hours. Progress of the reaction was checked by LC-MS. After completion of reaction the mixture was then lyophilized and purified by RP-HPLC using C18-phenomenex column.

Example 22. Conjugation of XTEN to Relaxin Derivative

The lyophilized protein, refolded relaxin with free cysteine was re-suspended in 0.25% TFA in water and acetonitrile mixture. Iodoacetylated XTEN 288 or 864 (1.2 equivalents; iodoacetylated at N-terminus) was added and then the pH was adjusted to 8.5 using 1M ammonium bicarbonate. The reaction proceeded at room temperature for 2 hours; the progress of the reaction was checked by LC-MS. After completion of reaction, the mixture was then buffer exchanged prior to purification via anion-exchange chromatography (Mono-Q). The desired fractions were then collected and underwent cleavage of mini-C-chain following similar procedures as exemplified in Example 16. The cleavage reaction was quenched and subjected to RP-HPLC to purify the XTEN-relaxin conjugates. Select data shown in Table 3.

Figure 17:
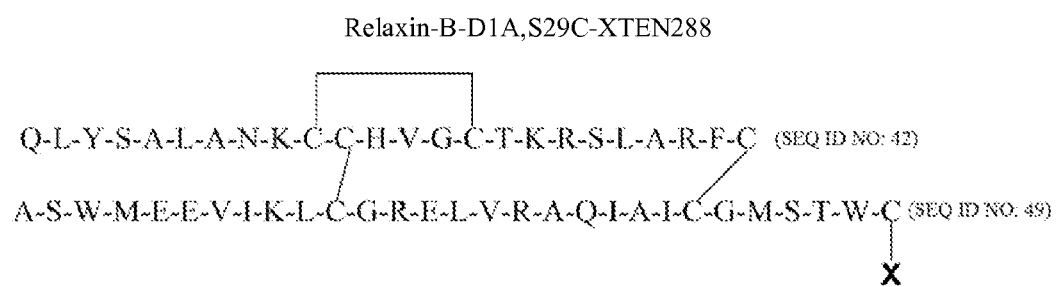
FIG. 17 shows an exemplary mTA. The exemplary mTA comprises a relaxin A-chain and B-chain attached to half-life extending moiety (represented by X). X may be XTEN-288 or XTEN-864. Disulfide bonds are depicted by brackets connecting two cysteine residues or by lines connecting two cysteine residues.

The following compounds in Table 1 were or are prepared using analogous procedures. Additional examples are shown in FIGS. 16A-B and 17.

TABLE 1

| entry | Structure* |
|---|---|
| 1 | 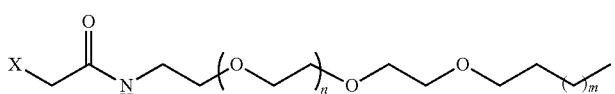<br>PEG: n = 0 to 10<br>m = 1-15 |
| 2 | 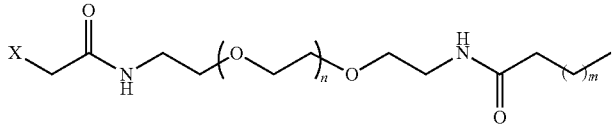<br>PEG: n = 0 to 10<br>m = 1-15 |
| 3 | 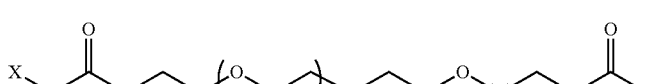<br>PEG: n = 0 to 10<br>m = 1-15 |
| 4 | 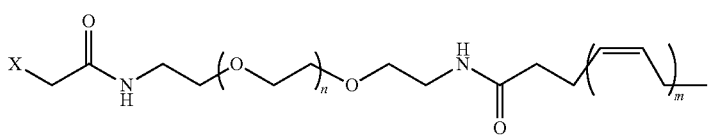<br>PEG: n = 0 to 10<br>m = 1-6 |
| 5 | 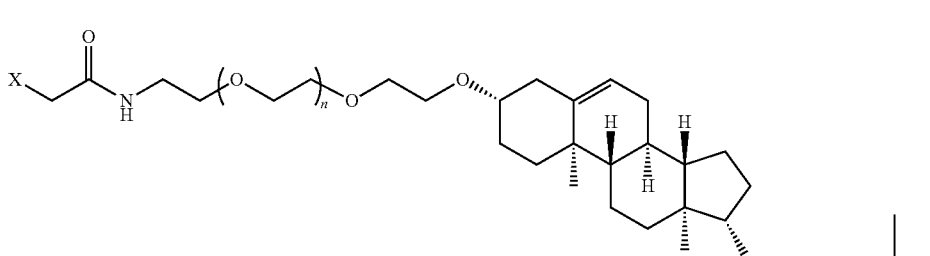<br>PEG: n = 0 to 10 |

TABLE 1-continued
| entry | Structure* |
|---|---|
| 6 | 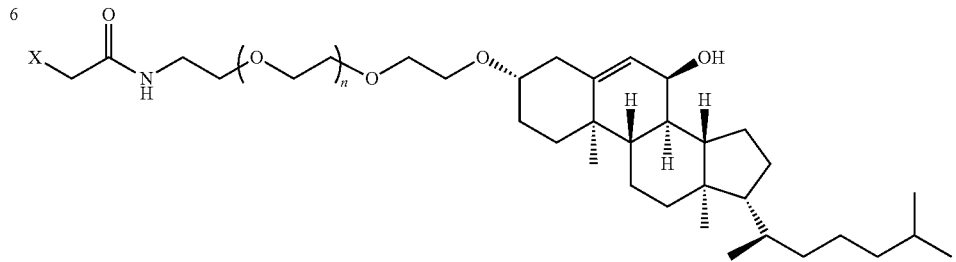<br>PEG: n = 0 to 10 |
| 7 | 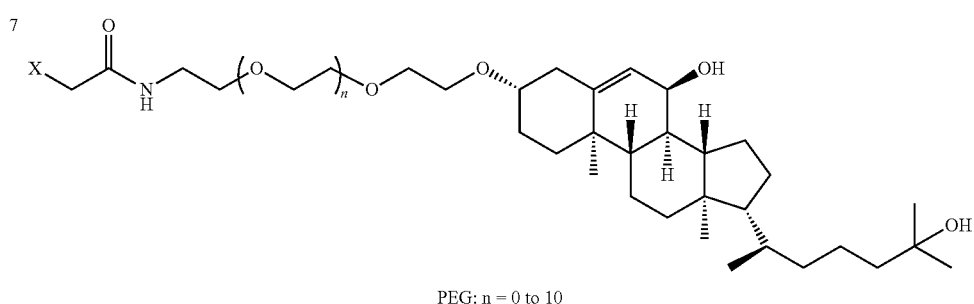<br>PEG: n = 0 to 10 |
| 8 | 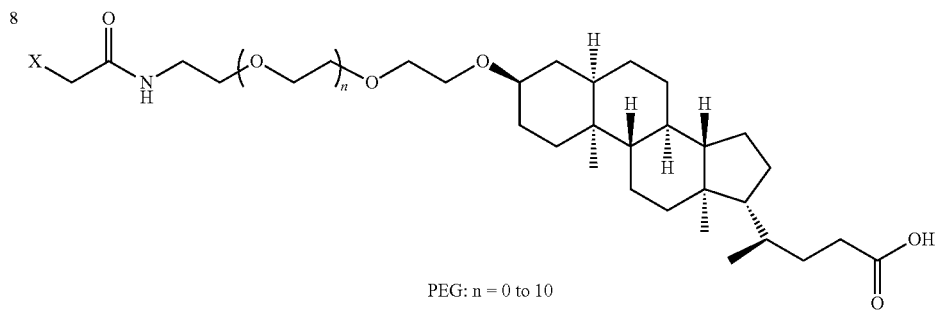<br>PEG: n = 0 to 10 |
| 9 | 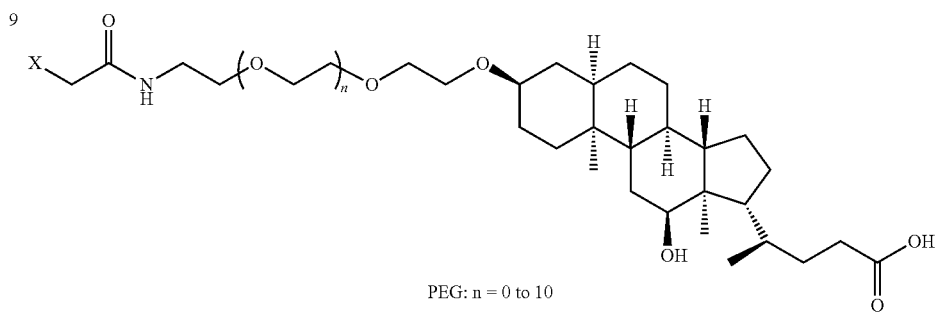<br>PEG: n = 0 to 10 |
| 10 | 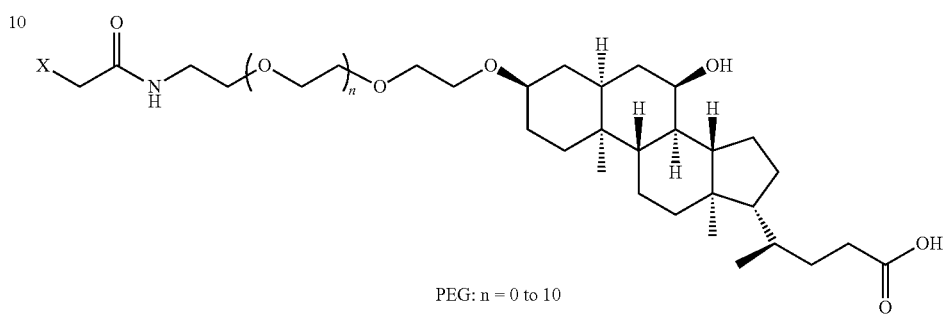<br>PEG: n = 0 to 10 |

TABLE 1-continued
| entry | Structure* |
|---|---|
| 11 | 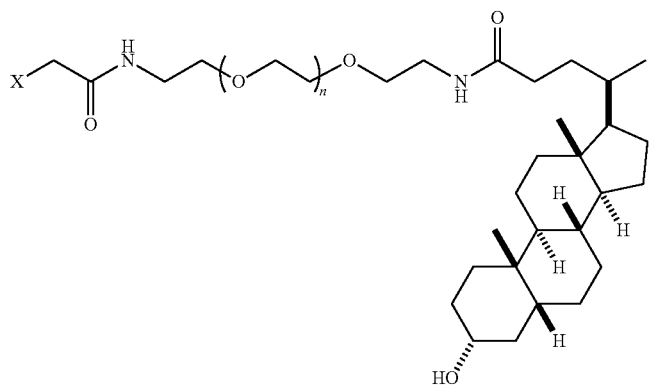
PEG: n = 0 to 10 |
| 12 | 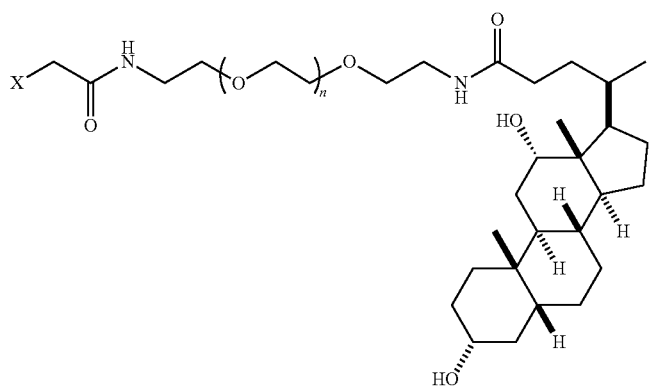
PEG: n = 0 to 10 |
| 13 | 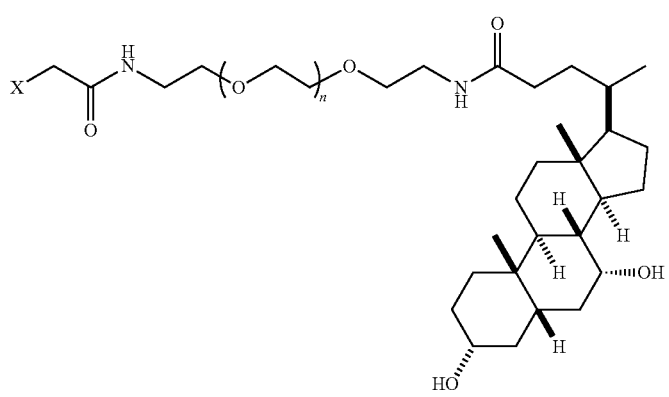
PEG: n = 0 to 10 |
| 14 | 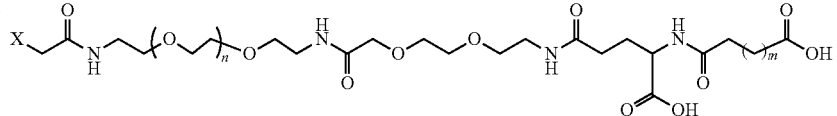
PEG: n = 1 to 10
m = 1-15 |

TABLE 1-continued
| entry | Structure* |
|---|---|
| 15 | 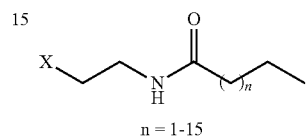
n = 1-15 |
| 16 | 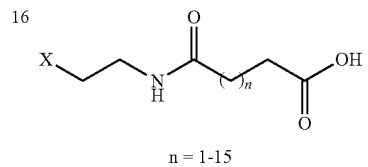
n = 1-15 |
| 17 | 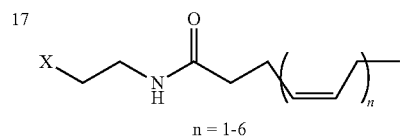
n = 1-6 |
| 18 | 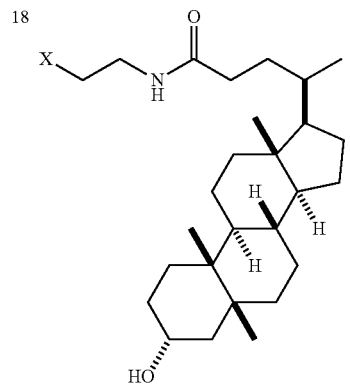 |
| 19 | 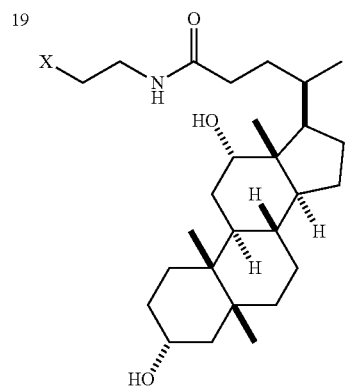 |

TABLE 1-continued
| entry | Structure* |
|---|---|
| 20 | 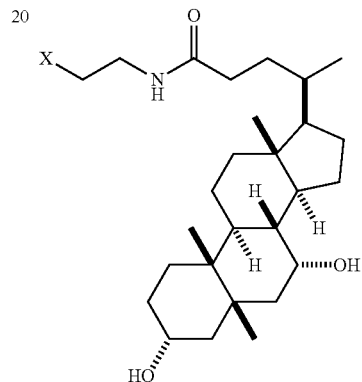 |
| 21 | 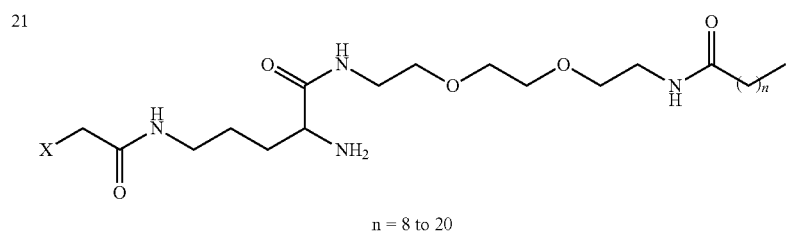
n = 8 to 20 |
| 22 | 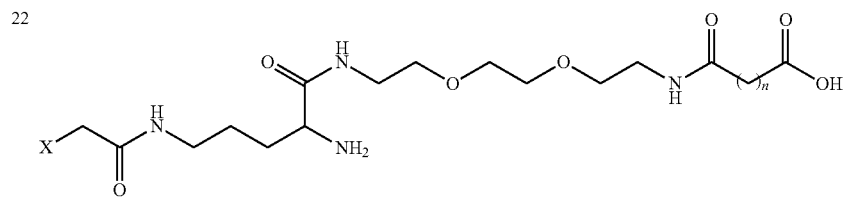
n = 8 to 20 |
| 23 | 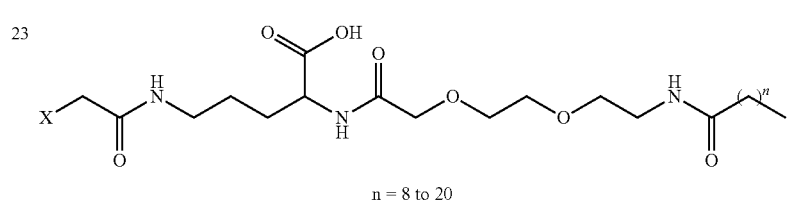
n = 8 to 20 |
| 24 | 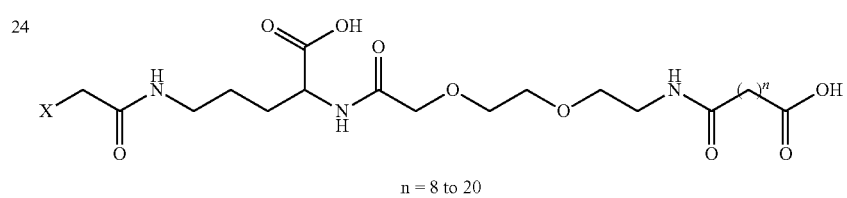
n = 8 to 20 |
| 25 | 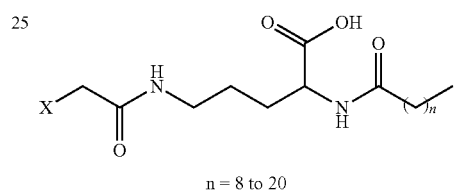
n = 8 to 20 |

TABLE 1-continued

| entry | Structure* |
|---|---|
| 26 | (structure with X, n = 8 to 20) |
| 27 | (structure with Y, NHFmoc, n = 8 to 20) |
| 28 | (structure with Y, NHFmoc, n = 8 to 20) |
| 29 | (structure with Y, NHFmoc, n = 8 to 20) |
| 30 | (structure with Y, NHFmoc, n = 8 to 20) |
| 31 | (structure with Z, n = 8 to 20) |
| 32 | (structure with Z, n = 8 to 20) |
| 33 | (structure with Z, n = 8 to 20) |

TABLE 1-continued

| entry | Structure* |
|---|---|
| 34 | (structure with Z-S-, gem-dimethyl, PEG2 linker, amide, alkyl chain; n = 8 to 20) |
| 35 | X-CH2-C(O)-NH-CH2CH2-O-CH2CH2-O-CH2CH2-NH-C(O)-(long alkyl chain) |
| 36 | (structure with X-acetamido-PEG-PEG-Lys(αCOOH) side chain acylated with HOOC-(CH2)n-C(O)-) |
| 37 | (structure with X-acetamido-PEG-PEG-Lys(αCONH2) side chain acylated with HOOC-(CH2)n-C(O)-) |
| 38 | X-CH2-C(O)-NH-(long alkyl chain) |
| 39 | X-acetamido-PEG-PEG-NH-C(O)-(long alkyl chain) |
| 40 | X-acetamido-PEG3-NH-C(O)-(CH2)n-COOH |
| 41 | (structure with X-acetamido-PEG-PEG-Lys(αCOOH) side chain acylated with HOOC-(CH2)n-C(O)-) |
| 42 | (structure with X-acetamido-PEG-PEG-Glu/Lys derivative-acyl chain) |
| 43 | XCH$_2$C(O)-SAGSPTGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPSASR (core sequence disclosed as SEQ ID NO: 66) |
| 44 | XCH$_2$C(O)-SAGSPGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGTSTEPSEGSA |

TABLE 1-continued

| entry | Structure* |
|---|---|
| | PGSPAGSPTSTEEGTSTEPSEGSAPGTSESATPESGPGSEPATSGSETPGTSESATPESGPGSEPATSGSETPGTSESATPESG<br>PGTSTEPSEGSAPGTSESATPESGPGSPAGSPTSTEEGSPAGSPTSTEEGSPAGSPTSTEEGTSESATPESGPGTSTEPSEGSA<br>PGTSESATPESGPGSEPATSGSETPGTSESATPESGPGSEPATSGSETPGTSESATPESGPGTSTEPSEGSAPGSPAGSPTSTE<br>EGTSESATPESGPGSEPATSGSETPGTSESATPESGPGSPAGSPTSTEEGSPAGSPTSTEEGTSTEP SEGSAPGTSESATPESG<br>PGTSESATPESGPGTSESATPESGPGSEPATSGSETPGSEPATSGSETPGSPAGSPTSTEEGTSTEPSEGSAPGTSTEPSEGSAP<br>GSEPATSGSETPGTSESATPESGPGTESASR (core sequence disclosed as SEQ ID NO: 67) |

*X can be Cl, I, Br, maleimide, or an amino acid which is part of the peptide (TA); Y can be OH or an amino acid which is part of the peptide (TA); Z can be S which is part of an amino acid which is part of the peptide (TA) or S which is part of a lipid derivative (to form a disulfide).

Example 23. Measuring Bioactivity of Ex4 and Oxm Peptides

Ex4 is a GLP1R agonist, and Oxm is a GLP1R and GCGR dual agonist. In vitro activity was determined based on the stimulation of adenylate cyclase activity in Hek293 cells stably expressing the GLP1R and GCGR receptor. Stable GCGR and GLP1R receptor expressing cells were maintained in Dulbecco's modified Eagle's medium/F-12 media supplemented with 200 ng/ml Zeocin (Invitrogen). A cyclic AMP responsive element driven luciferase (CRE-Luc) reporter line was generated by lentiviral transduction of these receptor overexpressing HEK293T cells with CRE-Luc lentivirus (Qiagen) and selected with puromycine (2 µg/mL) for two weeks. A reporter gene assay was used to detect cAMP levels and GLP1R and GCGR activation by Ex-4 or Oxm.

Assay detail: HEK293T cells expressing GLP1R and CRE-Luc were seeded at a density of $5 \times 10^3$ cells per well in 504 of Dulbecco's modified Eagle's medium/F-12 medium containing 10% FBS in 384-well solid bottom white plates. Cells were pre-incubated at 37° C. for overnight. Different concentrations of peptides (from 0.001 nM to 100 nM) were added in triplicate, incubated for 18 hours and luciferase activity was detected by adding 104 of Bright Glo (Promega). Luminescence was recorded on Envision (Perkin Elmer). $EC_{50}$ was calculated after non-linear curve fitting. For GCGR activity, a reporter cell the with GCGR and CRE-Luc was employed. Select data are shown in Table 3.

Example 24. Measuring Bioactivity of Toxin Peptides

Toxin-550 peptides were assayed on the IonFlux HT using standard running conditions for measurement of NaV 1.7 current. Briefly, HEK293 cells overexpressing the alpha and beta-1 subunits of human Nav1.7 (PrecisION, Millipore) were trypsinized, brought up in serum-free media and allowed to shake at room temperature for 30 minutes. Compounds were diluted into standard extracellular Ringer's solution (ECS) at desired concentration. Cells were washed once with ECS and then brought up in ECS at a concentration of 4 million cells/mL. IonFlux HT plate was set up according to standard protocols.

NaV 1.7 current was measured on the IonFlux according to the following voltage step protocol:

1. The cells were held at −90 mV with a period of 10 seconds.
2. The cells were stepped from −90 mV to −120 mV for 100 ms.
   a. then to −10 mV for 30 ms and
   b. then back to −90 mV for 30 ms.

Baseline current was allowed to stabilize for 5 minutes, then a control baseline (ECS only) was established. Compound was applied for 20 minutes, and then a positive control (peptide NaV1.7 blocker) was applied.

Leak subtraction was then performed on the data and the resulting currents are analyzed as follows:

1. Cursor subtraction (baseline-peak) was performed for all current sweeps to determine the amplitude of current (I).
2. ECS baseline current for each patch was taken as maximum current ($I_{max}$).
3. For a given time (e.g. 10 minutes post-compound addition), percent block was calculated as $I/I_{max}$.

Select data are shown in Table 3.

Example 25. In Vivo Pharmacokinetic (PK) Study for Half-Life Extension

Figure 12:
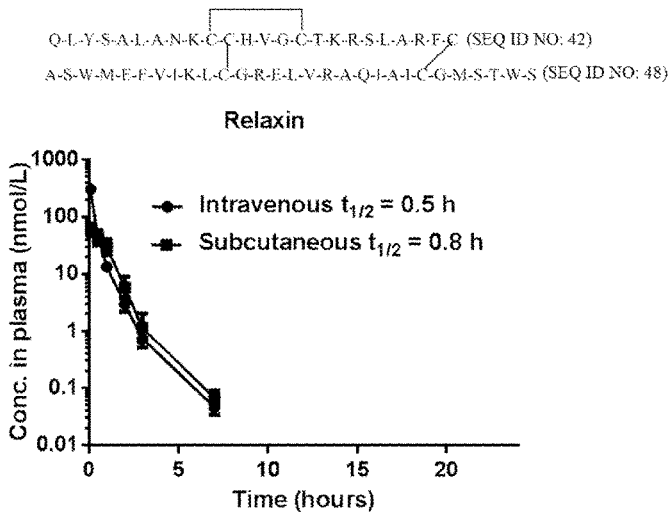
FIG. 12 shows mouse pharmacokinetic data for wild-type relaxin.
Figure 15:
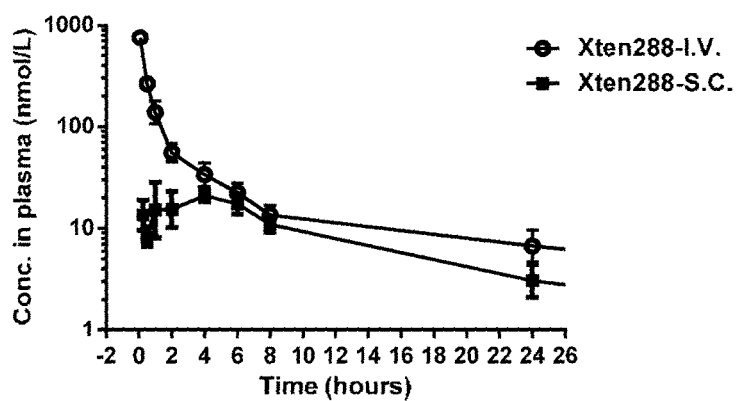
FIG. 15 shows mouse pharmacokinetic data for a non-limiting example of an XTEN-modified therapeutic agent (Relaxin-B-D1A,S29C-XTEN-288).

Lipid conjugated relaxin or other therapeutic agents are dosed in mice using sc, po, iv dosing. Plasma levels of TA are determined by ms, lgr7, glp1r and/or gcgr activation at different time points (e.g., i.v. PK 5 min, 0.5 h, 1 h, 2 h 4 h, 8 h, 24 h, 48 h, 96 h & 144 h and s.c. PK. 15 min, 0.5 h, 1 h, 2 h, 4 h, 8 h, 24 h, 48 h, 96 h and 144 h). Select PK data are shown in FIGS. 11, 12, and 15, and Table 2.

TABLE 2

| Entry | Name | Mass expected | Mass found | Activity, fold drop compared to relaxin | Half-life (hours) i.v., s.c. |
|---|---|---|---|---|---|
| 1 | Pro-Relaxin-B-D1A | 8183.7 | 8184.12 | 10 | |
| 2 | Relaxin-B-D1A | 5936.15 | 5936.92 | 0 | 0.5, 0.8 |
| 3 | Relaxin-B-D1AS29C-FA$_1$[a] | 6349.98 | 6350.52 | 0 | 0.5, 1.2 |
| 4 | Relaxin-B-D1AS29C-FA$_2$ | 6752.87 | 6753.27 | 70 | |
| 5 | Relaxin-B-D1AS29C-FA$_3$ | 6751.90 | 6752.49 | 30 | |
| 6 | Relaxin-B-D1AS29C-FA$_4$ | 6205.14 | 6205.62 | 170 | |
| 7 | Relaxin-B-D1AS29C-FA$_5$ | | | | |
| 8 | Relaxin-B-D1AS29C-PEG20K | | ND | 30 | |
| 9 | Relaxin-B-D1A, A-Q1C-FA$_1$[b] | 6309.10 | 6309.87 | 10 | |

TABLE 2-continued

| Entry | Name | Mass expected | Mass found | Activity, fold drop compared to relaxin | Half-life (hours) i.v., s.c. |
|---|---|---|---|---|---|
| 10 | Relaxin-B-D1A, A-Q1C-FA$_2$ | 6711.72 | 6712.45 | 15 | 3.5, 7.8 |
| 11 | Relaxin-B-D1A, A-Q1C-FA$_3$ | 6710.75 | 6711.33 | 25 | |
| 12 | Relaxin-B-D1A, A-Q1C-PEG20K | | | | 3.0, 7.1 |
| 13 | Relaxin-B-D1A, A-A5C-FA$_1$ | | ND | | |
| 14 | Relaxin-B-D1A, A-A5C-FA$_2$ | 6768.95 | 6769.36 | 25 | |
| 15 | Relaxin-B-D1A, A-A5C-FA$_3$ | 6767.98 | 6768.42 | 15 | |
| 16 | Relaxin-B-D1A, A-A5C-PEG20K | | | | |
| 17 | Relaxin-B-D1C-FA$_1$ | 6366.20 | 6366.82 | 3 | |
| 18 | Relaxin-B-D1C-FA$_2$ | 6768.82 | 6769.34 | 18 | |
| 19 | Relaxin-B-D1C-FA$_3$ | | | | |
| 20 | Relaxin-B-D1C-PEG-20K | | | | |
| 21 | Relaxin-B-D1A, A-R18C-FA$_1$ | 6281.05 | 6281.79 | 15 | |
| 22 | Relaxin-B-D1A, A-R18C-FA$_2$ | 6683.67 | 6684.26 | 30 | |
| 23 | Relaxin-B-D1A, A-R18C-FA$_3$ | 6682.70 | 6683.27 | 30 | |
| 24 | Relaxin-B-D1A, A-R18C-PEG-20K | | ND | | |
| 25 | Relaxin-B-D1AM25KM4K, A-Q1AH12K, B-S29C-FA$_1$ | 6278.29 | 6279.01 | 25 | |
| 26 | Relaxin-B-D1AM25KM4K, A-Q1AH12K, B-S29C-FA$_2$ | 6680.91 | 6681.42 | 150 | |
| 27 | Relaxin-B-D1AM25KM4K, A-Q1AH12K, B-S29C-FA$_3$ | 6679.94 | 6680.63 | 150 | |
| 28 | Relaxin-B-D1AM25KS29C-FA$_2$ | 6749.84 | 6750.32 | 48 | |
| 29 | Relaxin-B-D1AM4KS29C-FA$_2$ | 6749.84 | 6750.58 | 40 | |
| 30 | Relaxin-A-H12K, B-D1AS29C-FA$_2$ | 6743.91 | 6744.60 | 16 | |
| 31 | Relaxin-B-D1AM25KM4K, A-Q1AH12A, B-S29C-FA$_2$ | 6623.97 | 6624.48 | 8 | |
| 32 | Relaxin-B-D1AS29C-XTEN288 | 32236.1 | 32236.8 | 20 | 1.5, 4.5 |

$a$"B-" denotes B-chain.
$b$"A-" denotes A-chain

TABLE 3

| Entry | Name | Mass expected | Mass found | Activity (nM) |
|---|---|---|---|---|
| 1 | Tev-Relaxin-single-chain | 8841.1 | 8841.3 | 14 |
| 2 | GSGG-Relaxin-single-chain ("GSGG" disclosed as SEQ ID NO: 71) | 6817.9 | 6818.0 | 1 |
| 3 | Tev-Relaxin-B-S29C-single-chain | 8857.2 | 8857.3 | 11 |
| 4 | Tev-Relaxin-B-S29C-FA$_1$-single-chain | 9255.8 | 9255.8 | 29 |
| 5 | Tev-Relaxin-C chain | 20411.4 | 20495.5 | 6 |
| 6 | Tev-Relaxin | 8130.4 | 8214.5 | 2 |
| 7 | Tev-Relaxin-B-S29C-FA$_1$-C-Chain | 20826.0 | 20925.9 | 21 |
| 8 | Tev-Relaxin-B-S29C-FA$_1$ | 8544.9 | 8645.0 | 1 |
| 9 | Ex4-Cys40-FA$_1$ | 4688.6 | 1173.1 ([M + 4H]$^{4+}$); 938.6 ([M + 5H]$^{5+}$) | 0.14 (GLP-1R) |
| 10 | Oxm-Cys38-FA$_1$ | 4950.8 | 1238.7 ([M + 4H]$^{4+}$); 991.2 ([M + 5H]$^{5+}$) | 100 (GLP-1R) and 50 (GCGR) |
| 11 | 550- | 3947.1 | 3947.3 | 87% block at 100 nM |
| 12 | 550-4-GSGG ("GSGG" disclosed as SEQ ID NO: 71) | 4310.6 | 4310.2 | ND |
| 13 | 550-4-GSCGG-FA$_1$ ("GSCGG" disclosed as SEQ ID NO: 72) | 4709.4 | 4709.1 | 85% block at 100 nM |
| 14 | 550-GSGG ("GSGG" disclosed as SEQ ID NO: 71) | 4207.5 | 4206.9 | ND |
| 15 | 550-3-GSGG ("GSGG" disclosed as SEQ ID NO: 71) | 4310.7 | 4310.2 | ND |
| 16 | 550-3-GSGG-FA$_1$ ("GSGG" disclosed as SEQ ID NO: 71) | 4709.3 | 4709.1 | ND |
| 17 | 550-3-GGS | 4253.9 | 4253.1 | ND |
| 18 | 550-3-GGS-FA$_1$ | 4652.7 | 4652.3 | ND |

Example 26. Pharmacodynamic (PD) Study and In Vivo Efficacy in Acute Heart Failure Model After determination of the PK, appropriate dose regimen are determined and lipid conjugated relaxin are dosed using sc, po or iv to evaluate the efficacy of lipid conjugated relaxin in efficacy models for blood pressure, urine flow and/or ligament elongation. Also, lipid conjugated relaxin is evaluated in bleomycin induced fibrosis model in lung and liver and/or in diabetic wound healing models in old diabetic zucker fat rats.

Example 27. PD Study Using Mouse Interpubic Ligament Bioassay

Figure 13:
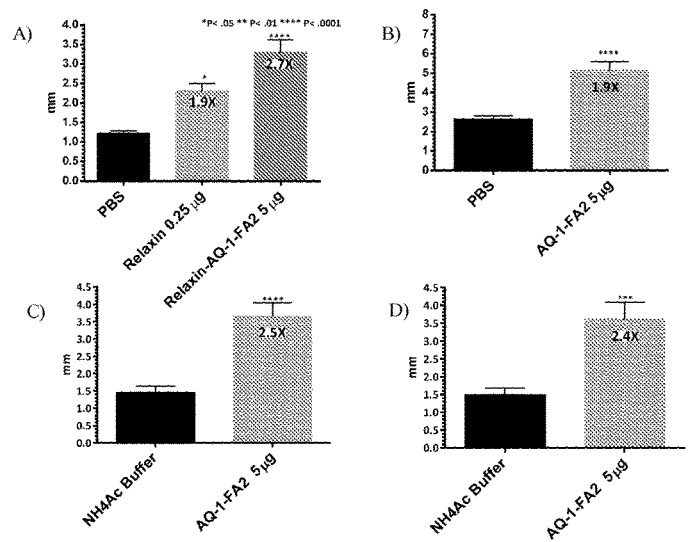
FIG. 13 shows pubic ligament length data for a lipid conjugate at various timepoints.
Figure 14:
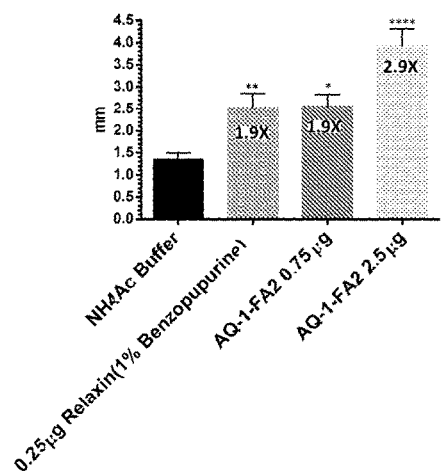
FIG. 14 shows dose response data for a lipid conjugate at a 24-h timepoint.

The bioactivities of relaxin analogs were determined in CD1 mice by employing the well-established and highly specific mouse interpubic ligament bioassays for relaxin as described by Steinetz et al. [Endocrinology (1960) 67:102-115]. Female CD1 virgin mice at 3-4 weeks old were chosen from the study. Animals were group-housed under controlled temperature (25° C.) and photoperiod (12:12-hour light-dark cycle) conditions, and given unrestricted access to standard diet and tap water (or specified drinking solution). On day 1 of treatment, mice were s.c. injected with 10 μg estradiol cypionate in 0.1 ml sesame oil. On day 8, mice were divided into different groups: vehicle control, wt relaxin (dissolved in a suspension of 1% benzopurpurine 4B in PBS buffer) and relaxin analogs (dissolved in 20 mM $NH_4Ac$ buffer, pH 6.5). Wt relaxin or relaxin analogs were administered at different dose through s.c. injection. At different time after relaxin injection, mice were euthanized and the length of interpubic ligaments was determined using caliper measurement. Select data are shown in FIGS. 13 and 14.

Example 28. Efficacy and Safety of Lipid Conjugated Relaxin for the Treatment of Acute Heart Failure Purpose: Different doses of lipid conjugated relaxin are compared to placebo to determine efficacy and safety for the treatment of patients hospitalized with acute heart failure.

| Condition | Intervention | Phase |
|---|---|---|
| Heart Failure, Congestive | Drug: Relaxin | Phase 1 |
| | Drug: Placebo | Phase 1 |

Study Type: Interventional
Study Design: Allocation: Randomized
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures: Relief of dyspnea in acute heart failure [Time Frame: Up to day 5] [Designated as safety issue: No]
Secondary Outcome Measures:
Days alive and out of hospital [Time Frame: Up to day 60] [Designated as safety issue: No]
CV death or rehospitalization due to heart failure or renal failure [Time Frame: Up to day 60] [Designated as safety issue: No]

| Arms | Assigned Intervention |
|---|---|
| Placebo Comparator: Placebo 48 hour iv infusion of placebo | Drug: Placebo Intravenous infusion for 48 h |
| Experimental: Lipid Conjugated Relaxin 48 hour iv infusion of lipid conjugated relaxin at 30 ug/kg/day | Drug: Lipid Conjugated Relaxin Intravenous infusion for 48 h at 30 ug/kg/day |

DETAILED DESCRIPTION

This is an international, randomized, double-blind, placebo-controlled, Phase II/III trial of intravenous recombinant relaxin for the treatment of signs and symptoms in patients hospitalized for acute decompensated heart failure. The Phase II pilot study has completed; the Phase III main portion of the trial is ongoing.
Eligibility
Ages Eligible for Study: 18 Years and older
Genders Eligible for Study: Both
Accepts Healthy Volunteers: No
Criteria
Inclusion Criteria:
Hospitalized for acute heart failure
Dyspnea at rest or with minimal exertion
Pulmonary congestion
Able to provide informed consent
Systolic blood pressure >125 mmHg
Impaired renal function defined as an eGFR of 30-75 mL/min/1.73 m2
Exclusion Criteria:
Use of other IV therapies for acute heart failure
Fever or sepsis
Recent major neurologic event
Recent major surgery
Recent acute coronary syndrome
Other recent investigational drug use

TABLE 4

Therapeutic Agents (TAs)-Nucleotide Sequences

| NAME | SEQ ID NO | SEQUENCE |
|---|---|---|
| Oxyntomodulin | 1 | CACTCTCAGGGTACCTTCACCTCTGACTACTCTAAATAC CTGGACTCTCGTCGTGCTCAGGACTTCGTTCAGTGGCTG ATGAACACCAAACGTAACCGTAACAACATCGCT |
| Relaxin | 2 | GACTCTTGGATGGAAGAAGTTATCAAACTGTGCGGTCGT GAACTGGTTCGTGCTCAGATCGCTATCTGCGGTATGTCT ACCTGGTCTGGTGGCGGTCGTGGCGGTCGTCAGCTGTAC TCTGCTCTGGCTAACAAATGCTGCCACGTTGGTTGCACC AAACGTTCTCTGGCTCGTTTCTGCTAA |
| Relaxin A Chain | 3 | CTGTACTCTGCTCTGGCTAACAAATGCTGCCACGTTGGT TGCACCAAACGTTCTCTGGCTCGTTTCTGC |
| Relaxin SB29C | 4 | GACTCTTGGATGGAAGAAGTTATCAAACTGTGCGGTCGT GAACTGGTTCGTGCTCAGATCGCTATCTGCGGTATGTCT ACCTGGTGC |
| Leptin | 5 | GTTCCGATCCAGAAAGTTCAGGACGACACCAAAACCCT GATCAAAACCATCGTTACCCGTATCAACGACATCTCTCA CACCCAGTCTGTTTCTGCTAAACAGCGTGTTACtGGTCTG GACTTCATCCCGGGTCTGCACCCGATCCTGTCTCTGTCTA AAATGGACCAGACCCTGGCTGTTTACCAGCAGGTTCTGA CCTCTCTGCCGTCTCAGAACGTTCTGCAGATCGCTAACG ACCTGGAAAACCTGCGTGACCTGCTGCACCTGCTGGCTT TCTCTAAATCTTGCTCTCTGCCGCAGACCTCTGGTCTGCA |

TABLE 4-continued

Therapeutic Agents (TAs)-Nucleotide Sequences

| NAME | SEQ ID NO | SEQUENCE |
|---|---|---|
| | | GAAACCGGAATCTCTGGACGGTGTTCTGGAgGCTTCTCT<br>GTACTCTACCGAAGTTGTTGCTCTGTCTCGTCTGCAGGG<br>TTCTCTGCAGGACATCCTGCAGCAGCTGGACGTTTCTCC<br>GGAATGCTAA |
| Betatrophin | 6 | GCTCCTCTGGGCGGTCCTGAACCAGCACAGTACGAGGA<br>ACTGACACTGTTGTTCCATGGAGCCTTGCAGCTGGGCCA<br>GGCCCTCAACGGCGTGTACCGCGCCACAGAGGCACGTTT<br>GACCGAGGCCGGACACAGCCTGGGTTTGTACGACAGAG<br>CCCTGGAGTTTCTGGGTACCGAAGTGCGTCAGGGCCAGG<br>ACGCAACTCAGGAGCTGAGAACCTCCCTCTCTGAGATCC<br>AGGTGGAGGAGGACGCCCTGCGCGCCGAGGCG<br>ACAGCACGCTCTTTGGGAGAAGTTGCTCGCGCTCAGCAG<br>GCCCTGCGTGATACCGTGCGGAGACTCCAAGTTCAGCTC<br>AGAGGCGCTTGGCTCGGACAGGCGCATCAGGAGTTCGA<br>GACCCTGAAAGCTCGTGCCGACAAACAGTCCCACCTGCT<br>GTGGGCGCTCACCGGTCACGTCCAGCGCCAGCAACGCG<br>AAATGGCCGAGCAGCAGCAATGGCTGCGCCAAATCCAG<br>CAGCGCCTGCATACCGCGGCCCTGCCAGCGTAA |
| FGF 21 | 7 | CACCCGATCCCGGACTCTTCTCCGCTGCTGCAGTTCGGT<br>GGTCAGGTTCGTCAGCGTTACCTGTACACCGACGACGCT<br>CAGCAGACCGAAGCTCACCTGGAAATCCGTGAAGACGG<br>TACtGTTGGTGGTGCTGCTGACCAGTCTCCGGAATCTCTG<br>CTGCAGCTGAAAGCTCTGAAACCGGGTGTTATCCAGATC<br>CTGGGTGTTAAAACCTCTCGTTTCCTGTGCCAGCGTCCG<br>GACGGTGCTCTGTACGGTTCTCTGCACTTCGACCCGGAG<br>GCATGCTCTTTCCGTGAACGTCTGCTGGAAGACGGTTAC<br>AACGTTTACCAGTCTGAAGCTCACGGTCTGCCGCTGCAC<br>CTGCCGGGTAACAAATCTCCGCACCGTGACCCGGCTCCG<br>CGTGGTCCGGCTCGTTTCCTGCCGCTGCGGGTCTGCCG<br>CCGGCTCTGCCGGAACCGCCGGGTATCCTGGCTCCGCAG<br>CCGCCGGACGTTGGTTCTTCTGACCCGCTGTCTATGGTT<br>GGTGGTTCTCAGGGTCGTTCTCCGTCTTACGAATCTCCGT<br>AA |
| GDF 11 | 8 | AACCTGGGTCTGGACTGCGACGAACACTCTTCTGAATCT<br>CGTTGCTGCCGTTACCCGCTGACCGTTGACTTCGAGGCG<br>TTCGGTTGGGACTGGATCATCGCTCCGAAACGTTACAAA<br>GCTAACTACTGCTCTGGTCAGTGCGAATACATGTTCATG<br>CAGAAATACCCGCACACCCACCTGGTTCAGCAGGCTAA<br>CCCCGCGTGGTTCTGCTGGTCCGTGCTGCACCCCGACCAA<br>AATGTCTCCGATCAACATGCTGTACTTCAACGACAAACA<br>GCAGATCATCTACGGTAAAATCCCGGGTATGGTTGTTGA<br>CCGTTGCGGTTGCTCTTAA |
| ANGPTL3 | 9 | GGATCCGGTGGTTTCACCATCAAACTGCTGCTGTTCATC<br>GTTCCGCTGGTTATCTCTTCTCGTATCGACCAGGACAAC<br>TCTTCTTTCGACTCTCTGTCTCCGGAACCGAAATCTCGTT<br>TCGCTATGCTGGACGACGTTAAAATCCTGGCTAACGGTC<br>TGCTGCAGCTGGGTCACGGTCTGAAAGACTTCGTTCACA<br>AAACCAAAGGTCAGATCAACGACATCTTCCAGAAACTG<br>AACATCTTCGACCAGTCTTTCTACGACCTGTCTCTGCAG<br>ACCTCTGAAATCAAAGAAGAAGAAAAAGAACTGCGTCG<br>TACCACCTACAAACTGCAGGTTAAAAACGAAGAAGTTA<br>AAAACATGTCTCTGGAACTGAACTCTAAACTGGAATCTC<br>TGCTGGAAGAAAAAATCCTGCTGCAGCAGAAAGTTAAA<br>TACCTGGAAGAACAGCTGACCAACCTGATCCAGAACCA<br>GCCGGAAACCCCGGAACACCCGGAAGTTACCTCTCTGA<br>AAACCTTCGTTGAAAAACAGGACAACTCTATCAAAGAC<br>CTGCTGCAGACCGTTGAAGACCAGTACAAACAGCTGAA<br>CCAGCAGCACTCTCAGATCAAAGAAATCGAAAACCAGC<br>TGCGTCGTACCTCTATCCAGGAACCGACCGAAATCTCTC<br>TGTCTTCTAAACCGCGTGCTCCGCGTACCACCCCGTTCCT<br>GCAGCTGAACGAAATCCGTAACGTTAAACACGACGGTA<br>TCCCGGCTGAATGCACCACCATCTACAACCGTGGTGAAC<br>ACACCTCTGGTATGTACGCTATCCGTCCGTCTAACTCTC<br>AGGTTTTCCACGTTTACTGCGACGTTATCTCTGGTTCTCC<br>GTGGACCCTGATCCAGCACCGTATCGACGGTTCTCAGAA<br>CTTCAACGAAACCTGGGAAAACTACAAATACGGTTTCG<br>GTCGTCTGGACGGTGAATTCTGGCTGGGTCTGGAAAAA<br>TCTACTCTATCGTTAAACAGTCTAACTACGTTCTGCGTAT<br>CGAACTGGAAGACTGGAAAGACAACAAACACTACATCG<br>AATACTCTTTCTACCTGGGTAACCACGAAACCAACTACA |

TABLE 4-continued

Therapeutic Agents (TAs)-Nucleotide Sequences

| NAME | SEQ ID NO | SEQUENCE |
|---|---|---|
| | | CCCTGCACCTGGTTGCTATCACCGGTAACGTTCCGAACG CTATCCCGAAGAAGAAGAAGAAAAAAAAGAAGAAGAA AT |

TABLE 5

Therapeutic Agents-Amino acid sequences

| NAME | SEQ ID NO | SEQUENCE |
|---|---|---|
| Oxyntomodulin | 10 | HSQGTFTSDYSKYLDSRRAQDFVQWLMNTKRNRNNIA |
| Exendin-4 or Exenatide | 11 | HGEGTFTSDLSKQMEEEAVRLFIEWLKNGGPSSGAPPPS |
| hGLP-1 | 12 | HAEGTFTSDVSSYLEGQAAKEFIAWLVKGR |
| Glucagon | 13 | HSQGTFTSDYSKYLDSRRAQDFVQWLMNT |
| Relaxin | 14 | DSWMEEVIKLCGRELVRAQIAICGMSTWSGGGRGGRQLY SALANKCCHVGCTKRSLARFC |
| Relaxin A Chain | 15 | LYSALANKCCHVGCTKRSLARFC |
| Relaxin SB29C | 16 | DSWMEEVIKLCGRELVRAQIAICGMSTWC |
| Leptin | 17 | VPIQKVQDDTKTLIKTIVTRINDISHTQSVSAKQRVTGLDFI PGLHPILSLSKMDQTLAVYQQVLTSLPSQNVLQIANDLEN LRDLLHLLAFSKSCSLPQTSGLQKPESLDGVLEASLYSTEV VALSRLQGSLQDILQQLDVSPEC |
| Betatrophin | 18 | APLGGPEPAQYEELTLLFHGALQLGQALNGVYRATEARL TEAGHSLGLYDRALEFLGTEVRQGQDATQELRTSLSEIQV EEDALHLRAEATARSLGEVARAQQALRDTVRRLQVQLRG AWLGQAHQEFETLKARADKQSHLLWALTGHVQRQQRE MAEQQQWLRQIQQRLHTAALPA |
| FGF 21 | 19 | HPIPDSSPLLQFGGQVRQRYLYTDDAQQTEAHLEIREDGT VGGAADQSPESLLQLKALKPGVIQILGVKTSRFLCQRPDG ALYGSLHFDPEACSFRERLLEDGYNVYQSEAHGLPLHLPG NKSPHRDPAPRGPARFLPLPGLPPALPEPPGILAPQPPDVGS SDPLSMVGGSQGRSPSYESP |
| GDF 11 | 20 | NLGLDCDEHSSESRCCRYPLTVDFEAFGWDWIIAPKRYKA NYCSGQCEYMFMQKYPHTHLVQQANPRGSAGPCCTPTK MSPINMLYFNDKQQIIYGKIPGMVVDRCGCS |
| ANGPTL3 | 21 | GSGGFTIKLLLFIVPLVISSRIDQDNSSFDSLSPEPKSRFAML DDVKILANGLLQLGHGLKDFVHKTKGQINDIFQKLNIFDQ SFYDLSLQTSEIKEEEKELRRTTYKLQVKNEEVKNMSLEL NSKLESLLEEKILLQQKVKYLEEQLTNLIQNQPETPEHPEV TSLKTFVEKQDNSIKDLLQTVEDQYKQLNQQHSQIKEIEN QLRRTSIQEPTEISLSSKPRAPRTTPFLQLNEIRNVKHDGIPA ECTTIYNRGEHTSGMYAIRPSNSQVFHVYCDVISGSPWTLI QHRIDGSQNFNETWENYKYGFGRLDGEFWLGLEKIYSIVK QSNYVLRIELEDWKDNKHYIEYSFYLGNHETNYTLHLVAI TGNVPNAIPKKKKKKKKKK |
| Moka | 22 | INVKCSLPQQCIKPCKDAGMRFGKCMNKKCRCYS |
| VM-24 | 23 | AAAISCVGSPECPPKCRAQGCKNGKCMNRKCKCYYC |
| Oxm-Cys38 | 24 | HsQGTFTSDYSKYLDSRRAQDFVQWLMNTKRNRNNIAC |
| Ex4-Cys40 | 25 | HGEGTFTSDLSKQMEEEAVRLFIEWLKNGGPSSGAPPPSC |
| Toxin H8-Tev-550 | 26 | HHHHHHHHENLYFQGSCGGECIGMFKSCDPENDKCCKGR TCSRKHRWCKYKL |

TABLE 5-continued

Therapeutic Agents-Amino acid sequences

| NAME | SEQ ID NO | SEQUENCE |
|---|---|---|
| 550-GSGG ("GSGG" disclosed as SEQ ID NO: 71) | 27 | GSGGEECIGMFKSCDPENDKCCKGRTCSRKHRWCKYKL |
| 550-4-GSCGG ("GSCGG" disclosed as SEQ ID NO: 72) | 28 | GSCGGECIGMFKSCDPENDKCCKGRTCSRKHRWCKYKL |
| 550-3-GSGG ("GSGG" disclosed as SEQ ID NO: 71) | 29 | GSGGECIGMFKSCDPENDKCCKGRTCSRKHRWCKYKLC |
| Toxin-550 | 30 | ECIGMFKSCDPENDKCCKGRTCSRKHRWCKYKL |
| 550-3 | 31 | ECIGMFKSCDPENDKCCKGRTCSRKHRWCKYKLGGSC |
| Tev-Relaxin-single-chain | 32 | *HHHHHHHHENLYFQGSGGDSWMEEVIKLCGRELVRAQI AICGMSTWSGGGRGGRQLYSALANKCCHVGCTKRSLARF C* |
| GSGG-Relaxin-single chain ("GSGG" disclosed as SEQ ID NO: 71) | 33 | *GSGGDSWMEEVIKLCGRELVRAQIAICGMSTWSGGG RGGRQLYSALANKCCHVGCTKRSLARFC* |
| Tev-Relaxin-C-chain | 34 | *HHHHHHHHENLYFQGSGGDSWMEEVIKLCGRELVRA QIAICGMSTWSKRSLSQEDAPQTPRPVAEIVPSFINKDTETI NMMSEFVANLPQELKLTLSEMQPALPQLQQHVPVLKDSS LLFEEFKKLIRNRQSEAADSSPSELKYLGLDTHSRKKRQLY SALANKCCHVGCTKRSLARFC* |
| Tev-Relaxin Chain 1 | 35 | *HHHHHHHHENLYFQSGGDSWMEEVIKLCGRELVRAQI AICGMSTWS* |
| Tev-Relaxin Chain 2 | 36 | *QLYSALANKCCHVGCTKRSLARFC* |
| Tev-Relaxin-B-S29C-single-chain | 37 | *HHHHHHHHENLYFQGSGGDSWMEEVIKLCGRELVRAQI AICGMSTWCGGGRGGRQLYSALANKCCHVGCTKRSLAR FC* |
| Tev-Relaxin-B-S29C-C-chain | 38 | *HHHHHHHHENLYFQGSGGDSWMEEVIKLCGRELVRA QIAICGMSTWCKRSLSQEDAPQTPRPVAEIVPSFINKDTETI NMMSEFVANLPQELKLTLSEMQPALPQLQQHVPVLKDSS LLFEEFKKLIRNRQSEAADSSPSELKYLGLDTHSRKKRQLY SALANKCCHVGCTKRSLARFC* |
| Pro-relaxin-B-D1A | 39 | *MIEEGRDSWMEEVIKLCGRELVRAQIAICGMSTWSKRKP TGYGSRKKRQLYSALANKCCHVGCTKRSLARFC* |
| B-chain | 40 | DSWMEEVIKLCGRELVRAQIAICGMSTWS |
| A-chain | 41 | LYSALANKCCHVGCTKRSLARFC |
| Relaxin A chain 1 | 42 | QLYSALANKCCHVGCTKRSLARFC |
| Relaxin A chain 2 | 43 | QLYSCLANKCCHVGCTKRSLARFC |
| Relaxin A chain 3 | 44 | QLYSALANKCCKVGCTKRSLARFC |
| Relaxin A chain 4 | 45 | CLYSALANKCCHVGCTKRSLARFC |
| Relaxin A chain 5 | 46 | ALYSALANKCCAVGCTKRSLARFC |
| Relaxin A chain 6 | 47 | ALYSALANKCCAVGCTKRSLARFC |
| Relaxin B chain 1 | 48 | ASWMEEVIKLCGRELVRAQIAICGMSTWS |

TABLE 5-continued

Therapeutic Agents-Amino acid sequences

| NAME | SEQ ID NO | SEQUENCE |
| --- | --- | --- |
| Relaxin B chain 2 | 49 | ASWMEEVIKLCGRELVRAQIAICGMSTWC |
| Relaxin B chain 3 | 50 | ASWKEEVIKLCGRELVRAQIAICGKSTWC |
| Relaxin B chain 4 | 51 | ASWKEEVIKLCGRELVRAQIAICGMSTWC |
| Relaxin B chain 5 | 52 | CSWMEEVIKLCGRELVRAQIAICGMSTWS |
| H2-Relaxin A chain | 53 | ZLYSALANKCCHVGCTKRSLARFC |
| H2-Relaxin B chain | 54 | DSWMEEVIKCLGRELVRAQIAICGMSTWS |
| Relaxin A chain 7 | 55 | QLYSALANKCCHVGCTKCSLARFC |
| Relaxin B chain 6 | 56 | ASWMEEVIKLCGRELVRAQIAICGKSTWC |

Lowercase letters represent D-amino acids
Tev = Tev protease cleavage sequence (ENLYFQ) (SEQ ID NO: 73)
*= free N-terminal or unmodified C-terminal carboxyl group

TABLE 6

Relaxin2 Construction Primer Sequences

| NAME | SEQ ID NO | SEQUENCE |
| --- | --- | --- |
| Relaxin2 f1 (#32) | 57 | TATTTCCAGGGATCCGGTGGTGACTCTTGGATGGAAGA AGTTATCAAACTGTGCGGTCGT |
| Relaxin2 r6 linker S26C (#212) | 58 | TAGACATACCGCAGATAGCGATCTGAGCACGAACCAG TTCACGACCGCACAGTTTGATAA |
| Relaxin2 Linker f1 S26C (#213) | 59 | CGCTATCTGCGGTATGTCTACCTGGTCTGGTGGCGGTC GTGGCGGTCGTCAGCTGTACTC |
| Relaxin2 Linker f1 (#209) | 60 | CGCTATCTGCGGTATGTCTACCTGGTCTGGTGGCGGTC GTGGCGGTCGTCAGCTGTACTC |
| Relaxin2 r6 (#43) | 61 | TAGACATACCGCAGATAGCGATCTGAGCACGAACCAG TTCACGACCGCACAGTTTGATAA |
| Relaxin2 Linker f1 S29C (#214) | 62 | CGCTATCTGCGGTATGTCTACCTGGTCTGGTGGCGGTC GTGGCGGTCGTCAGCTGTACTC |
| Relaxin2 Linker r1 (#210) | 63 | TTTGGTGCAACCAACGTGGCAGCATTTGTTAGCCAGAG CAGAGTACAGCTGACGACCGCC |
| pVB008 Relaxin2 Amp for (#60) | 64 | AATCTGTATTTCCAGGGATCCGGTGGTGA |
| Relaxin2 Linker Amp rev (#211) | 65 | TGGCTAAGCTTTAGCAGAAACGAGCCAGAGAACGTTT GGTGCAACCAACGTGGC |

TABLE 7

XTEN-Amino acid sequences

| NAME | SEQ ID NO | SEQUENCE |
| --- | --- | --- |
| XTEN 288 | 66 | SAGSPTGPGSEPATSGSETPGTSESATPESGPGSEPATSGSE TPGTSESATPESGPGTSTEPSEGSAPGSPAGSPTSEEGTSE SATPESGPGSEPATSGSETPGTSESATPESGPGSPAGSPTST EEGSPAGSPTSEEGTSTEPSEGSAPGTSESATPESGPGTSE SATPESGPGTSESATPESGPGSEPATSGSETPGSEPATSGSE TPGSPAGSPTSTEEGTSTEPSEGSAPGTSTEPSEGSAPGSEP ATSGSETPGTSESATPESGPGTSTEPSEGSAPSASR |
| XTEN 864 | 67 | SAGSPGSPAGSPTSTEEGTSESATPESGPGTSTEPSEGSAPG SPAGSPTSTEEGTSTEPSEGSAPGTSESATPESGPGTSESAT |

TABLE 7-continued

XTEN-Amino acid sequences

| SEQ ID NAME | NO | SEQUENCE |
|---|---|---|
| | | PESGPGSEPATSGSETPGSEPATSGSETPGSPAGSPTSTEEG TSESATPESGPGTSTEPSEGSAPGTSTEPSEGSAPGSPAGSP TSTEEGTSTEPSEGSAPGTSTEPSEGSAPGTSESATPESGPG TSTEPSEGSAPGTSESATPESGPGSEPATSGSETPGTSTEPSE GSAPGTSTEPSEGSAPGTSESATPESGPGTSESATPESGPGS PAGSPTSTEEGTSESATPESGPGSEPATSGSETPGTSESATP ESGPGTSTEPSEGSAPGTSTEPSEGSAPGTSTEPSEGSAPGT STEPSEGSAPGTSTEPSEGSAPGTSTEPSEGSAPGSPAGSPT STEEGTSTEPSEGSAPGTSESATPESGPGSEPATSGSETPGT SESATPESGPGSEPATSGSETPGTSESATPESGPGTSTEPSE |

TABLE 7-continued

XTEN-Amino acid sequences

| SEQ ID NAME | NO | SEQUENCE |
|---|---|---|
| | | GSAPGTSESATPESGPGSPAGSPTSTEEGSPAGSPTSTEEGS PAGSPTSTEEGTSESATPESGPGTSTEPSEGSAPGTSESATP ESGPGSEPATSGSETPGTSESATPESGPGSEPATSGSETPGT SESATPESGPGTSTEPSEGSAPGSPAGSPTSTEEGTSESATP ESGPGSEPATSGSETPGTSESATPESGPGSPAGSPTSTEEGS PAGSPTSTEEGTSTEPSEGSAPGTSESATPESGPGTSESATP ESGPGTSESATPESGPGSEPATSGSETPGSEPATSGSETPGS PAGSPTSTEEGTSTEPSEGSAPGTSTEPSEGSAPGSEPATSG SETPGTSESATPESGPGTESASR |

What is claimed is:

1. A lipid conjugate (LC), comprising
   a. one or more lipids, the lipids selected from a group consisting of sterols, bile acids, vitamin E, fatty di-acids, fatty acids, fatty amides, fatty amines, fatty alcohols, and derivatives thereof; and
   b. a therapeutic agent (TA) comprising two amino acid sequences that are SEQ ID NO: 45 and 48;

wherein the one or more lipids are conjugated to the TA via a cysteine residue at the N-terminus of SEQ ID NO: 45.

2. The LC of claim 1, wherein the LC has the structure:

TA-A$^1$-P$^1$-L          Formula (I)

wherein:
   TA is the therapeutic agent;
   A$^1$ is a chemical group linking TA and P$^1$ or L;
   P$^1$ is a bond or comprises polyglycol; and
   L is the lipid.

3. The LC of claim 2, wherein a sulfur atom of the cysteine residue of the TA is connected to A$^1$ via a chemical bond.

4. The LC of claim 2, wherein
   A$^1$ is selected from

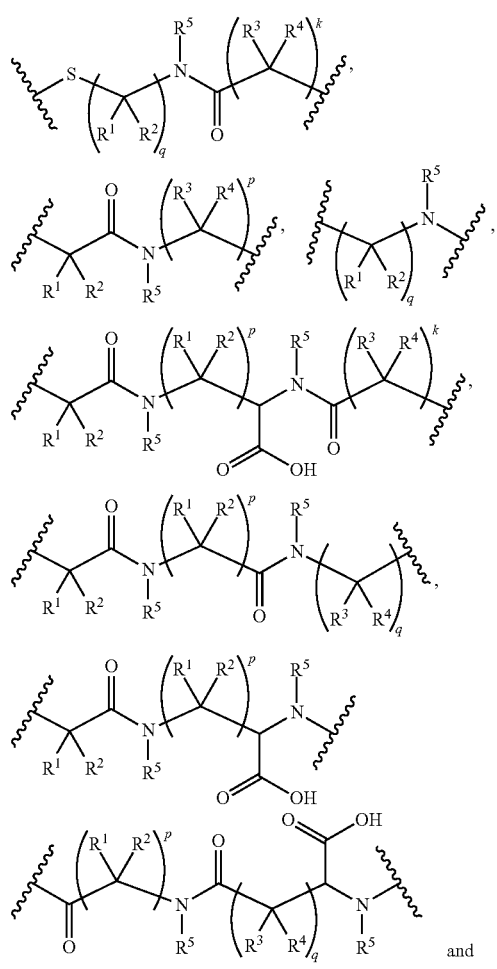

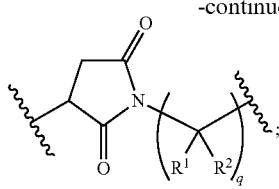

P$^1$ is -PEG-A$^2$-;
PEG is selected from

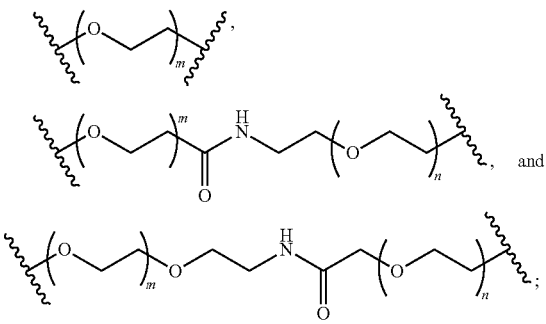

A$^2$ is selected from a bond,

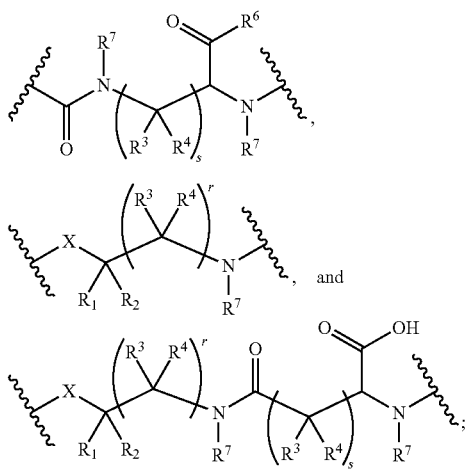

L is tetradecanoic acid, octadecanedioic acid, tetradecylamine, myristic acid, stearic acid, docosahexaenoic acid, lithocholic acid ester, cholic acid or palmitic acid;
X is a bond, NR$^5$, S, or O;
each R$^1$, R$^2$, R$^3$, and R$^4$ is independently selected from H, halo, CN, —SR$^5$, alkyl, cycloalkyl, haloalkyl, —NR$^5$R$^5$, and —OR$^5$;
each R$^5$ is independently H, alkyl, haloalkyl, arylalkyl, or heteroalkyl;
R$^6$ is OH or —NR$^5$R$^5$;
each R$^7$ is independently selected from H, alkyl, haloalkyl, arylalkyl, and heteroalkyl;
m and n are independently 1, 2, 3, 4, 5, 6, 7, 8, 9, 10, 11, 12, 13, 14, 15, 16, 17, 18, 19, or 20;
r is 1, 2, 3, 4, 5, 6, 7, 8, 9, or 10;
s is 1, 2, 3, 4, or 5;
k is 1, 2, 3, 4, 5, 6, 7, 8, 9, or 10;
p is 2, 3, 4, 5, 6, 7, 8, 9, or 10; and
q is 2, 3, 4, 5, 6, 7, 8, 9, or 10.

5. The LC of claim 1, wherein the LC is selected from the following:

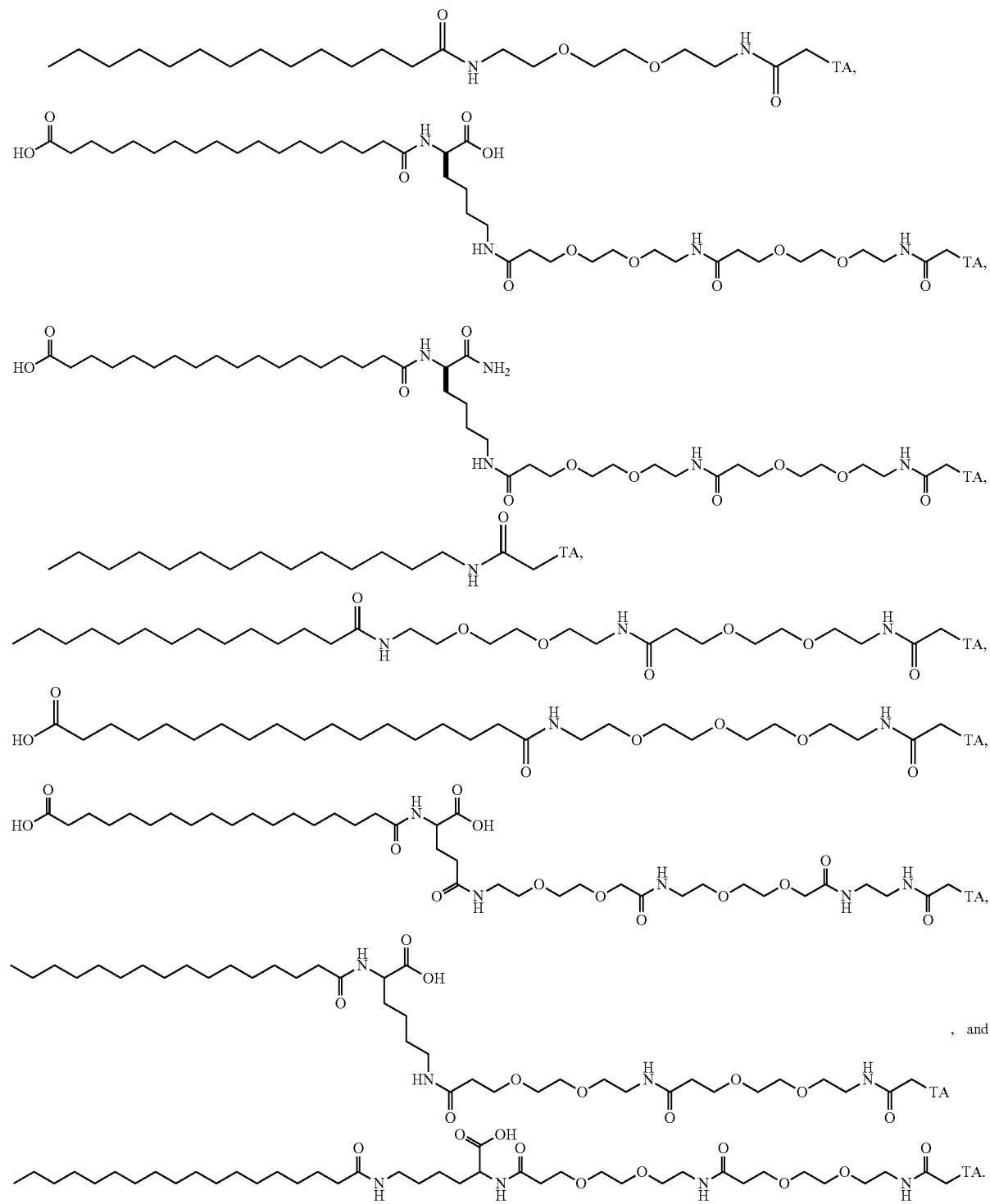

6. A pharmaceutical composition comprising the LC of claim 1.

7. A method for treating a disease or condition selected from acute heart failure, congestive heart failure, compensated heart failure, decompensated heart failure, scleroderma, diffuse scleroderma, systemic scleroderma, fibromyalgia, fibrosis, and preeclampsia; or inducing labor in a subject in need thereof, the method comprising administering to the subject a composition comprising a therapeutically effective amount of the LC of claim 1.

8. The method of claim 7, wherein the LC is administered with one or more additional therapeutic agents selected from a group consisting of an anti-inflammatory drug, a statin, a diuretic, a beta-blocker, an angiotensin converting enzyme inhibitor, an angiotensin II receptor blocker or any combination thereof.

* * * * *

UNITED STATES PATENT AND TRADEMARK OFFICE
CERTIFICATE OF CORRECTION

PATENT NO. : 10,286,078 B2
APPLICATION NO. : 14/917689
DATED : May 14, 2019
INVENTOR(S) : Shen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Tenth Day of December, 2019

Andrei Iancu
*Director of the United States Patent and Trademark Office*

SEQUENCE LISTING

```
<160> NUMBER OF SEQ ID NOS: 73

<210> SEQ ID NO 1
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cactctcagg gtaccttcac ctctgactac tctaaatacc tggactctcg tcgtgctcag      60
gacttcgttc agtggctgat gaacaccaaa cgtaaccgta acaacatcgc t             111

<210> SEQ ID NO 2
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gactcttgga tggaagaagt tatcaaactg tgcggtcgtg aactggttcg tgctcagatc      60
gctatctgcg gtatgtctac ctggtctggt ggcggtcgtg gcggtcgtca gctgtactct     120
gctctggcta caaatgctg ccacgttggt tgcaccaaac gttctctggc tcgtttctgc     180
taa                                                                    183

<210> SEQ ID NO 3
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctgtactctg ctctggctaa caaatgctgc cacgttggtt gcaccaaacg ttctctggct      60
cgtttctgc                                                              69

<210> SEQ ID NO 4
<211> LENGTH: 87
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 4

```
gactcttgga tggaagaagt tatcaaactg tgcggtcgtg aactggttcg tgctcagatc    60
gctatctgcg gtatgtctac ctggtgc                                        87
```

<210> SEQ ID NO 5
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gttccgatcc agaaagttca ggacgacacc aaaaccctga tcaaaaccat cgttacccgt    60
atcaacgaca tctctcacac ccagtctgtt tctgctaaac agcgtgttac tggtctggac   120
ttcatcccgg gtctgcaccc gatcctgtct ctgtctaaaa tggaccagac cctggctgtt   180
taccagcagg ttctgaccct ctgccgtctc agaacgttca tgcagatcgc taacgacctg   240
gaaaacctgc gtgacctgct gcacctgctg gctttctcta aatcttgctc tctgccgcag   300
acctctggtc tgcagaaacc ggaatctctg acggtgttct tggaggcttc tctgtactct   360
accgaagttg ttgctctgtc tcgtctgcag ggttctctgc aggacatcct gcagcagctg   420
gacgtttctc cggaatgcta a                                            441
```

<210> SEQ ID NO 6
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gctcctctgg gcggtcctga accagcacag tacgaggaac tgacactgtt gttccatgga    60
gccttgcagc tgggccaggc cctcaacggc gtgtaccgcg ccacagaggc acgtttgacc   120
gaggccggac acagcctggg tttgtacgac agagccctgg agtttctggg taccgaagtg   180
cgtcagggcc aggacgcaac tcaggagctg agaacctccc tctctgagat ccaggtggag   240
gaggacgccc tgcacctgcg cgccgaggcg acagcacgct ctttgggaga agttgctcgc   300
gctcagcagg ccctgcgtga taccgtgcgg agactccaag ttcagctcag aggcgcttgg   360
ctcggacagg cgcatcagga gttcgagacc ctgaaagctc gtgccgacaa acagtccac   420
ctgctgtggg cgctcaccgg tcacgtccag cgccagcaac gcgaaatggc cgagcagcag   480
caatggctgc gccaaatcca gcagcgcctg cataccgcgg ccctgccagc gtaa        534
```

<210> SEQ ID NO 7
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
cacccgatcc cggactcttc tccgctgctg cagttcggtg gtcaggttcg tcagcgttac    60
ctgtacaccg acgacgctca gcagaccgaa gctcacctgg aaatccgtga agacggtact   120
```

```
gttggtggtg ctgctgacca gtctccggaa tctctgctgc agctgaaagc tctgaaaccg      180
ggtgttatcc agatcctggg tgttaaaacc tctcgtttcc tgtgccagcg tccggacggt      240
gctctgtacg gttctctgca cttcgacccg gaggcatgct ctttccgtga acgtctgctg      300
gaagacggtt acaacgttta ccagtctgaa gctcacggtc tgccgctgca cctgccgggt      360
aacaaatctc gcaccgtga cccggctccg cgtggtccgg ctcgtttcct gccgctgccg       420
ggtctgccgc cggctctgcc ggaaccgccg ggtatcctgg ctccgcagcc gccggacgtt      480
ggttcttctg acccgctgtc tatggttggt ggttctcagg gtcgttctcc gtcttacgaa      540
tctccgtaa                                                             549

<210> SEQ ID NO 8
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
aacctgggtc tggactgcga cgaacactct tctgaatctc gttgctgccg ttacccgctg       60
accgttgact tcgaggcgtt cggttgggac tggatcatcg ctccgaaacg ttacaaagct      120
aactactgct ctggtcagtg cgaatacatg ttcatgcaga ataccccgca cacccacctg      180
gttcagcagg ctaacccgcg tggttctgct ggtccgtgct gcaccccgac caaaatgtct      240
ccgatcaaca tgctgtactt caacgacaaa cagcagatca tctacggtaa aatcccgggt      300
atggttgttg accgttgcgg ttgctcttaa                                      330

<210> SEQ ID NO 9
<211> LENGTH: 1162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ggatccggtg gtttcaccat caaactgctg ctgttcatcg ttccgctggt tatctcttct       60
cgtatcgacc aggacaactc ttcttttcgac tctctgtctc cggaaccgaa atctcgtttc     120
gctatgctgg acgacgttaa aatcctggct aacggtctgc tgcagctggg tcacggtctg      180
aaagacttcg ttcacaaaac caaaggtcag atcaacgaca tcttccagaa actgaacatc      240
ttcgaccagt ctttctacga cctgtctctg cagacctctg aaatcaaaga gaagaaaaa      300 gaactgcgtc gtaccaccta caactgcag gttaaaaacg aagaagttaa aaacatgtct      360
ctggaactga actctaaact ggaatctctg ctggaagaaa aaatcctgct gcagcagaaa      420
gttaaatacc tggaagaaca gctgaccaac ctgatccaga accagccgga acccccggaa      480
cacccggaag ttacctctct gaaaaccttc gttgaaaaac aggacaactc tatcaaagac      540
ctgctgcaga ccgttgaaga ccagtacaaa cagctgaacc agcagcactc tcagatcaaa      600
gaaatcgaaa accagctgcg tcgtacctct atccaggaac cgaccgaaat ctctctgtct      660
tctaaaccgc gtgctccgcg taccaccccg ttcctgcagc tgaacgaaat ccgtaacgtt      720
aaacacgacg gtatcccggc tgaatgcacc accatctaca accgtggtga acacacctct      780
ggtatgtacg ctatccgtcc gtctaactct caggttttcc acgtttactg cgacgttatc      840
tctggttctc cgtggaccct gatccagcac cgtatcgacg ttctcagaa cttcaacgaa      900
```

```
acctgggaaa actacaaata cggtttcggt cgtctggacg gtgaattctg gctgggtctg    960
gaaaaaatct actctatcgt taaacagtct aactacgttc tgcgtatcga actggaagac   1020
tggaaagaca acaaacacta catcgaatac tctttctacc tgggtaacca cgaaaccaac   1080
tacaccctgc acctggttgc tatcaccggt aacgttccga acgctatccc gaagaagaag   1140
aagaaaaaaa agaagaagaa at                                            1162
```

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 14
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Arg Gly Gly Arg Gln Leu Tyr Ser Ala Leu Ala Asn Lys Cys Cys His
        35                  40                  45

Val Gly Cys Thr Lys Arg Ser Leu Ala Arg Phe Cys
    50                  55                  60
```

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Leu Tyr Ser Ala Leu Ala Asn Lys Cys Cys His Val Gly Cys Thr Lys
1               5                   10                  15

Arg Ser Leu Ala Arg Phe Cys
            20
```

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Cys
            20                  25
```

<210> SEQ ID NO 17
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30
```

```
Lys Gln Arg Val Thr Gly Leu Asp Phe Ile Pro Gly Leu His Pro Ile
            35                  40                  45

Leu Ser Leu Ser Lys Met Asp Gln Thr Leu Ala Val Tyr Gln Gln Val
 50                  55                  60

Leu Thr Ser Leu Pro Ser Gln Asn Val Leu Gln Ile Ala Asn Asp Leu
65                  70                  75                  80

Glu Asn Leu Arg Asp Leu Leu His Leu Leu Ala Phe Ser Lys Ser Cys
                85                  90                  95

Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
            115                 120                 125

Leu Gln Gly Ser Leu Gln Asp Ile Leu Gln Gln Leu Asp Val Ser Pro
130                 135                 140

Glu Cys
145

<210> SEQ ID NO 18
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Pro Leu Gly Gly Pro Glu Pro Ala Gln Tyr Glu Glu Leu Thr Leu
 1               5                  10                  15

Leu Phe His Gly Ala Leu Gln Leu Gly Gln Ala Leu Asn Gly Val Tyr
                20                  25                  30

Arg Ala Thr Glu Ala Arg Leu Thr Glu Ala Gly His Ser Leu Gly Leu
            35                  40                  45

Tyr Asp Arg Ala Leu Glu Phe Leu Gly Thr Glu Val Arg Gln Gly Gln
 50                  55                  60

Asp Ala Thr Gln Glu Leu Arg Thr Ser Leu Ser Glu Ile Gln Val Glu
65                  70                  75                  80

Glu Asp Ala Leu His Leu Arg Ala Glu Ala Thr Ala Arg Ser Leu Gly
                85                  90                  95

Glu Val Ala Arg Ala Gln Gln Ala Leu Arg Asp Thr Val Arg Arg Leu
            100                 105                 110

Gln Val Gln Leu Arg Gly Ala Trp Leu Gly Gln Ala His Gln Glu Phe
            115                 120                 125

Glu Thr Leu Lys Ala Arg Ala Asp Lys Gln Ser His Leu Leu Trp Ala
130                 135                 140

Leu Thr Gly His Val Gln Arg Gln Arg Glu Met Ala Glu Gln Gln
145                 150                 155                 160

Gln Trp Leu Arg Gln Ile Gln Gln Arg Leu His Thr Ala Ala Leu Pro
                165                 170                 175

Ala

<210> SEQ ID NO 19
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 19

| His | Pro | Ile | Pro | Asp | Ser | Ser | Pro | Leu | Leu | Gln | Phe | Gly | Gly | Gln | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser
                165                 170                 175

Pro Ser Tyr Glu Ser Pro
            180

<210> SEQ ID NO 20
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 21
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gly Ser Gly Gly Phe Thr Ile Lys Leu Leu Phe Ile Val Pro Leu
1               5                   10                  15

Val Ile Ser Ser Arg Ile Asp Gln Asp Asn Ser Ser Phe Asp Ser Leu
            20                  25                  30

Ser Pro Glu Pro Lys Ser Arg Phe Ala Met Leu Asp Asp Val Lys Ile
        35                  40                  45

Leu Ala Asn Gly Leu Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Gln Thr Ser Glu Ile Lys
                85                  90                  95

Glu Glu Glu Lys Glu Leu Arg Arg Thr Thr Tyr Lys Leu Gln Val Lys
                100                 105                 110

Asn Glu Glu Val Lys Asn Met Ser Leu Glu Leu Asn Ser Lys Leu Glu
            115                 120                 125

Ser Leu Leu Glu Glu Lys Ile Leu Leu Gln Gln Lys Val Lys Tyr Leu
        130                 135                 140

Glu Glu Gln Leu Thr Asn Leu Ile Gln Asn Gln Pro Glu Thr Pro Glu
145                 150                 155                 160

His Pro Glu Val Thr Ser Leu Lys Thr Phe Val Glu Lys Gln Asp Asn
                165                 170                 175

Ser Ile Lys Asp Leu Leu Gln Thr Val Glu Asp Gln Tyr Lys Gln Leu
            180                 185                 190

Asn Gln Gln His Ser Gln Ile Lys Glu Ile Glu Asn Gln Leu Arg Arg
        195                 200                 205

Thr Ser Ile Gln Glu Pro Thr Glu Ile Ser Leu Ser Ser Lys Pro Arg
210                 215                 220

Ala Pro Arg Thr Thr Pro Phe Leu Gln Leu Asn Glu Ile Arg Asn Val
225                 230                 235                 240

Lys His Asp Gly Ile Pro Ala Glu Cys Thr Thr Ile Tyr Asn Arg Gly
                245                 250                 255

Glu His Thr Ser Gly Met Tyr Ala Ile Arg Pro Ser Asn Ser Gln Val
            260                 265                 270

Phe His Val Tyr Cys Asp Val Ile Ser Gly Ser Pro Trp Thr Leu Ile
        275                 280                 285

Gln His Arg Ile Asp Gly Ser Gln Asn Phe Asn Glu Thr Trp Glu Asn
    290                 295                 300

Tyr Lys Tyr Gly Phe Gly Arg Leu Asp Gly Glu Phe Trp Leu Gly Leu
305                 310                 315                 320

Glu Lys Ile Tyr Ser Ile Val Lys Gln Ser Asn Tyr Val Leu Arg Ile
                325                 330                 335

Glu Leu Glu Asp Trp Lys Asp Asn Lys His Tyr Ile Gly Tyr Ser Phe
            340                 345                 350

Tyr Leu Gly Asn His Glu Thr Asn Tyr Thr Leu His Leu Val Ala Ile
        355                 360                 365

Thr Gly Asn Val Pro Asn Ala Ile Pro Lys Lys Lys Lys Lys Lys
    370                 375                 380

Lys Lys Lys
385
```

```
<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ile Asn Val Lys Cys Ser Leu Pro Gln Gln Cys Ile Lys Pro Cys Lys
1               5                   10                  15

Asp Ala Gly Met Arg Phe Gly Lys Cys Met Asn Lys Lys Cys Arg Cys
            20                  25                  30

Tyr Ser

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ala Ala Ile Ser Cys Val Gly Ser Pro Glu Cys Pro Pro Lys Cys
1               5                   10                  15

Arg Ala Gln Gly Cys Lys Asn Gly Lys Cys Met Asn Arg Lys Cys Lys
            20                  25                  30

Cys Tyr Tyr Cys
        35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Cys
        35                  40
```

-continued

```
<210> SEQ ID NO 26
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

His His His His His His His His Glu Asn Leu Tyr Phe Gln Gly Ser
1               5                   10                  15

Cys Gly Gly Glu Cys Ile Gly Met Phe Lys Ser Cys Asp Pro Glu Asn
            20                  25                  30

Asp Lys Cys Cys Lys Gly Arg Thr Cys Ser Arg Lys His Arg Trp Cys
        35                  40                  45

Lys Tyr Lys Leu
    50

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ser Gly Gly Glu Cys Ile Gly Met Phe Lys Ser Cys Asp Pro
1               5                   10                  15

Glu Asn Asp Lys Cys Cys Lys Gly Arg Thr Cys Ser Arg Lys His Arg
            20                  25                  30

Trp Cys Lys Tyr Lys Leu
        35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Ser Cys Gly Gly Glu Cys Ile Gly Met Phe Lys Ser Cys Asp Pro
1               5                   10                  15

Glu Asn Asp Lys Cys Cys Lys Gly Arg Thr Cys Ser Arg Lys His Arg
            20                  25                  30

Trp Cys Lys Tyr Lys Leu
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Ser Gly Gly Glu Cys Ile Gly Met Phe Lys Ser Cys Asp Pro Glu
1               5                   10                  15

Asn Asp Lys Cys Cys Lys Gly Arg Thr Cys Ser Arg Lys His Arg Trp
            20                  25                  30
```

Cys Lys Tyr Lys Leu Cys
        35

<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Cys Ile Gly Met Phe Lys Ser Cys Asp Pro Glu Asn Asp Lys Cys
1               5                   10                  15

Cys Lys Gly Arg Thr Cys Ser Arg Lys His Arg Trp Cys Lys Tyr Lys
            20                  25                  30

Leu

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Cys Ile Gly Met Phe Lys Ser Cys Asp Pro Glu Asn Asp Lys Cys
1               5                   10                  15

Cys Lys Gly Arg Thr Cys Ser Arg Lys His Arg Trp Cys Lys Tyr Lys
            20                  25                  30

Leu Gly Gly Ser Cys
        35

<210> SEQ ID NO 32
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His His His His His His His His Glu Asn Leu Tyr Phe Gln Gly Ser
1               5                   10                  15

Gly Gly Asp Ser Trp Met Glu Glu Val Ile Lys Leu Cys Gly Arg Glu
            20                  25                  30

Leu Val Arg Ala Gln Ile Ala Ile Cys Gly Met Ser Thr Trp Ser Gly
        35                  40                  45

Gly Gly Arg Gly Gly Arg Gln Leu Tyr Ser Ala Leu Ala Asn Lys Cys
    50                  55                  60

Cys His Val Gly Cys Thr Lys Arg Ser Leu Ala Arg Phe Cys
65                  70                  75

<210> SEQ ID NO 33
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gly Ser Gly Gly Asp Ser Trp Met Glu Glu Val Ile Lys Leu Cys Gly
1               5                   10                  15

Arg Glu Leu Val Arg Ala Gln Ile Ala Ile Cys Gly Met Ser Thr Trp
            20                  25                  30

Ser Gly Gly Gly Arg Gly Gly Arg Gln Leu Tyr Ser Ala Leu Ala Asn
            35                  40                  45

Lys Cys Cys His Val Gly Cys Thr Lys Arg Ser Leu Ala Arg Phe Cys
    50                  55                  60
```

<210> SEQ ID NO 34
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
His His His His His His His His Glu Asn Leu Tyr Phe Gln Gly Ser
1               5                   10                  15

Gly Gly Asp Ser Trp Met Glu Glu Val Ile Lys Leu Cys Gly Arg Glu
            20                  25                  30

Leu Val Arg Ala Gln Ile Ala Ile Cys Gly Met Ser Thr Trp Ser Lys
        35                  40                  45

Arg Ser Leu Ser Gln Glu Asp Ala Pro Gln Thr Pro Arg Pro Val Ala
    50                  55                  60

Glu Ile Val Pro Ser Phe Ile Asn Lys Asp Thr Glu Thr Ile Asn Met
65                  70                  75                  80

Met Ser Glu Phe Val Ala Asn Leu Pro Gln Glu Leu Lys Leu Thr Leu
                85                  90                  95

Ser Glu Met Gln Pro Ala Leu Pro Gln Leu Gln Gln His Val Pro Val
                100                 105                 110

Leu Lys Asp Ser Ser Leu Leu Phe Glu Glu Phe Lys Lys Leu Ile Arg
            115                 120                 125

Asn Arg Gln Ser Glu Ala Ala Asp Ser Ser Pro Ser Glu Leu Lys Tyr
    130                 135                 140

Leu Gly Leu Asp Thr His Ser Arg Lys Lys Arg Gln Leu Tyr Ser Ala
145                 150                 155                 160

Leu Ala Asn Lys Cys Cys His Val Gly Cys Thr Lys Arg Ser Leu Ala
                165                 170                 175

Arg Phe Cys
```

<210> SEQ ID NO 35
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
His His His His His His His His Glu Asn Leu Tyr Phe Gln Ser Gly
1               5                   10                  15

Gly Asp Ser Trp Met Glu Glu Val Ile Lys Leu Cys Gly Arg Glu Leu
            20                  25                  30

Val Arg Ala Gln Ile Ala Ile Cys Gly Met Ser Thr Trp Ser
        35                  40                  45
```

```
<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 37
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His His His His His His His His Glu Asn Leu Tyr Phe Gln Gly Ser
1               5                   10                  15

Gly Gly Asp Ser Trp Met Glu Glu Val Ile Lys Leu Cys Gly Arg Glu
            20                  25                  30

Leu Val Arg Ala Gln Ile Ala Ile Cys Gly Met Ser Thr Trp Cys Gly
        35                  40                  45

Gly Gly Arg Gly Gly Arg Gln Leu Tyr Ser Ala Leu Ala Asn Lys Cys
    50                  55                  60

Cys His Val Gly Cys Thr Lys Arg Ser Leu Ala Arg Phe Cys
65                  70                  75

<210> SEQ ID NO 38
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

His His His His His His His His Glu Asn Leu Tyr Phe Gln Gly Ser
1               5                   10                  15

Gly Gly Asp Ser Trp Met Glu Glu Val Ile Lys Leu Cys Gly Arg Glu
            20                  25                  30

Leu Val Arg Ala Gln Ile Ala Ile Cys Gly Met Ser Thr Trp Cys Lys
        35                  40                  45

Arg Ser Leu Ser Gln Glu Asp Ala Pro Gln Thr Pro Arg Pro Val Ala
    50                  55                  60

Glu Ile Val Pro Ser Phe Ile Asn Lys Asp Thr Glu Thr Ile Asn Met
65                  70                  75                  80

Met Ser Glu Phe Val Ala Asn Leu Pro Gln Glu Leu Lys Leu Thr Leu
                85                  90                  95

Ser Glu Met Gln Pro Ala Leu Pro Gln Leu Gln Gln His Val Pro Val
            100                 105                 110

Leu Lys Asp Ser Ser Leu Leu Phe Glu Glu Phe Lys Lys Leu Ile Arg
        115                 120                 125

Asn Arg Gln Ser Glu Ala Ala Asp Ser Ser Pro Ser Glu Leu Lys Tyr
    130                 135                 140
```

Leu Gly Leu Asp Thr His Ser Arg Lys Arg Gln Leu Tyr Ser Ala
145                 150                 155                 160

Leu Ala Asn Lys Cys Cys His Val Gly Cys Thr Lys Arg Ser Leu Ala
            165                 170                 175

Arg Phe Cys

<210> SEQ ID NO 39
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ile Glu Glu Gly Arg Asp Ser Trp Met Glu Val Ile Lys Leu
1               5                   10                  15

Cys Gly Arg Glu Leu Val Arg Ala Gln Ile Ala Ile Cys Gly Met Ser
            20                  25                  30

Thr Trp Ser Lys Arg Lys Pro Thr Gly Tyr Gly Ser Arg Lys Lys Arg
        35                  40                  45

Gln Leu Tyr Ser Ala Leu Ala Asn Lys Cys Cys His Val Gly Cys Thr
    50                  55                  60

Lys Arg Ser Leu Ala Arg Phe Cys
65                  70

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Tyr Ser Ala Leu Ala Asn Lys Cys Cys His Val Gly Cys Thr Lys
1               5                   10                  15

Arg Ser Leu Ala Arg Phe Cys
            20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

-continued

```
Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Leu Tyr Ser Cys Leu Ala Asn Lys Cys Cys His Val Gly Cys Thr
1               5                   10                  15

Lys Arg Ser Leu Ala Arg Phe Cys
            20

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Leu Tyr Ser Ala Leu Ala Asn Lys Cys Cys Lys Val Gly Cys Thr
1               5                   10                  15

Lys Arg Ser Leu Ala Arg Phe Cys
            20

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Leu Tyr Ser Ala Leu Ala Asn Lys Cys Cys Ala Val Gly Cys Thr
1               5                   10                  15

Lys Arg Ser Leu Ala Arg Phe Cys
            20

<210> SEQ ID NO 47
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 47

Ala Leu Tyr Ser Ala Leu Ala Asn Lys Cys Cys Ala Val Gly Cys Thr
1               5                   10                  15

Lys Arg Ser Leu Ala Arg Phe Cys
            20

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ser Trp Met Glu Glu Val Ile Lys Leu Cys Gly Arg Glu Leu Val
1               5                   10                  15

Arg Ala Gln Ile Ala Ile Cys Gly Met Ser Thr Trp Cys
            20                  25

<210> SEQ ID NO 50
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ser Trp Lys Glu Glu Val Ile Lys Leu Cys Gly Arg Glu Leu Val
1               5                   10                  15

Arg Ala Gln Ile Ala Ile Cys Gly Lys Ser Thr Trp Cys
            20                  25

<210> SEQ ID NO 51
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Ser Trp Lys Glu Glu Val Ile Lys Leu Cys Gly Arg Glu Leu Val
1               5                   10                  15

Arg Ala Gln Ile Ala Ile Cys Gly Met Ser Thr Trp Cys
```

```
            20                  25

<210> SEQ ID NO 52
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 53
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MISC_FEATURE
<222> LOCATION: (1)..(24)
<223> OTHER INFORMATION: see specification as filed for detailed
      description of substitutions and preferred embodiments

<400> SEQUENCE: 53

Xaa Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 54
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ser Trp Met Glu Glu Val Ile Lys Cys Leu Gly Arg Glu Leu Val
1               5                   10                  15

Arg Ala Gln Ile Ala Ile Cys Gly Met Ser Thr Trp Ser
            20                  25

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Leu Tyr Ser Ala Leu Ala Asn Lys Cys Cys His Val Gly Cys Thr
1               5                   10                  15

Lys Cys Ser Leu Ala Arg Phe Cys
            20
```

<210> SEQ ID NO 56
<211> LENGTH: 29
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 56

Ala Ser Trp Met Glu Glu Val Ile Lys Leu Cys Gly Arg Glu Leu Val
1               5                   10                  15

Arg Ala Gln Ile Ala Ile Cys Gly Lys Ser Thr Trp Cys
            20                  25

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 57
tatttccagg gatccggtgg tgactcttgg atggaagaag ttatcaaact gtgcggtcgt    60

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 58
tagacatacc gcagatagcg atctgagcac gaaccagttc acgaccgcac agtttgataa    60

<210> SEQ ID NO 59
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 59
cgctatctgc ggtatgtcta cctggtctgg tggcggtcgt ggcggtcgtc agctgtactc    60

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 60
cgctatctgc ggtatgtcta cctggtctgg tggcggtcgt ggcggtcgtc agctgtactc    60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 61
tagacatacc gcagatagcg atctgagcac gaaccagttc acgaccgcac agtttgataa    60

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgctatctgc ggtatgtcta cctggtctgg tggcggtcgt ggcggtcgtc agctgtactc    60

<210> SEQ ID NO 63
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tttggtgcaa ccaacgtggc agcatttgtt agccagagca gagtacagct gacgaccgcc    60

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aatctgtatt tccagggatc cggtggtga                                      29

<210> SEQ ID NO 65
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tggctaagct ttagcagaaa cgagccagag aacgtttggt gcaaccaacg tggc          54

<210> SEQ ID NO 66
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ser Ala Gly Ser Pro Thr Gly Pro Gly Ser Glu Pro Ala Thr Ser Gly
1               5                   10                  15

Ser Glu Thr Pro Gly Thr Ser Glu Ser Ala Thr Pro Glu Ser Gly Pro
            20                  25                  30

Gly Ser Glu Pro Ala Thr Ser Gly Ser Glu Thr Pro Gly Thr Ser Glu
        35                  40                  45

Ser Ala Thr Pro Glu Ser Gly Pro Gly Thr Ser Thr Glu Pro Ser Glu
    50                  55                  60

Gly Ser Ala Pro Gly Ser Pro Ala Gly Ser Pro Thr Ser Thr Glu Glu

```
                65                  70                  75                  80
Gly Thr Ser Glu Ser Ala Thr Pro Glu Ser Gly Pro Gly Ser Glu Pro
                85                  90                  95
Ala Thr Ser Gly Ser Glu Thr Pro Gly Thr Ser Glu Ser Ala Thr Pro
            100                 105                 110
Glu Ser Gly Pro Gly Ser Pro Ala Gly Ser Pro Thr Ser Thr Glu Glu
        115                 120                 125
Gly Ser Pro Ala Gly Ser Pro Thr Ser Thr Glu Glu Gly Thr Ser Thr
    130                 135                 140
Glu Pro Ser Glu Gly Ser Ala Pro Gly Thr Ser Glu Ser Ala Thr Pro
145                 150                 155                 160
Glu Ser Gly Pro Gly Thr Ser Glu Ser Ala Thr Pro Glu Ser Gly Pro
                165                 170                 175
Gly Thr Ser Glu Ser Ala Thr Pro Glu Ser Gly Pro Gly Ser Glu Pro
            180                 185                 190
Ala Thr Ser Gly Ser Glu Thr Pro Gly Ser Glu Pro Ala Thr Ser Gly
        195                 200                 205
Ser Glu Thr Pro Gly Ser Pro Ala Gly Ser Pro Thr Ser Thr Glu Glu
    210                 215                 220
Gly Thr Ser Thr Glu Pro Ser Glu Gly Ser Ala Pro Gly Thr Ser Thr
225                 230                 235                 240
Glu Pro Ser Glu Gly Ser Ala Pro Gly Ser Pro Ala Thr Ser Gly
                245                 250                 255
Ser Glu Thr Pro Gly Thr Ser Glu Ser Ala Thr Pro Glu Ser Gly Pro
            260                 265                 270
Gly Thr Ser Thr Glu Pro Ser Glu Gly Ser Ala Pro Ser Ala Ser Arg
        275                 280                 285

<210> SEQ ID NO 67
<211> LENGTH: 864
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Ala Gly Ser Pro Gly Ser Pro Ala Gly Ser Pro Thr Ser Thr Glu
1               5                   10                  15
Glu Gly Thr Ser Glu Ser Ala Thr Pro Glu Ser Gly Pro Gly Thr Ser
            20                  25                  30
Thr Glu Pro Ser Glu Gly Ser Ala Pro Gly Ser Pro Ala Gly Ser Pro
        35                  40                  45
Thr Ser Thr Glu Glu Gly Thr Ser Thr Glu Pro Ser Glu Gly Ser Ala
    50                  55                  60
Pro Gly Thr Ser Thr Glu Pro Ser Glu Gly Ser Ala Pro Gly Thr Ser
65                  70                  75                  80
Glu Ser Ala Thr Pro Glu Ser Gly Pro Gly Ser Glu Pro Ala Thr Ser
                85                  90                  95
Gly Ser Glu Thr Pro Gly Ser Glu Pro Ala Thr Ser Gly Ser Glu Thr
            100                 105                 110
Pro Gly Ser Pro Ala Gly Ser Pro Thr Ser Thr Glu Glu Gly Thr Ser
        115                 120                 125
Glu Ser Ala Thr Pro Glu Ser Gly Pro Gly Thr Ser Thr Glu Pro Ser
    130                 135                 140
```

-continued

```
Glu Gly Ser Ala Pro Gly Thr Ser Thr Glu Pro Ser Glu Gly Ser Ala
145                 150                 155                 160

Pro Gly Ser Pro Ala Gly Ser Pro Thr Ser Thr Glu Glu Gly Thr Ser
                165                 170                 175

Thr Glu Pro Ser Glu Gly Ser Ala Pro Gly Thr Ser Thr Glu Pro Ser
            180                 185                 190

Glu Gly Ser Ala Pro Gly Thr Ser Glu Ser Ala Thr Pro Glu Ser Gly
        195                 200                 205

Pro Gly Thr Ser Thr Glu Pro Ser Glu Gly Ser Ala Pro Gly Thr Ser
    210                 215                 220

Glu Ser Ala Thr Pro Glu Ser Gly Pro Gly Ser Glu Pro Ala Thr Ser
225                 230                 235                 240

Gly Ser Glu Thr Pro Gly Thr Ser Thr Glu Pro Ser Glu Gly Ser Ala
                245                 250                 255

Pro Gly Thr Ser Thr Glu Pro Ser Glu Gly Ser Ala Pro Gly Thr Ser
                260                 265                 270

Glu Ser Ala Thr Pro Glu Ser Gly Pro Gly Thr Ser Glu Ser Ala Thr
            275                 280                 285

Pro Glu Ser Gly Pro Gly Ser Pro Ala Gly Ser Pro Thr Ser Thr Glu
    290                 295                 300

Glu Gly Thr Ser Glu Ser Ala Thr Pro Glu Ser Gly Pro Gly Ser Glu
305                 310                 315                 320

Pro Ala Thr Ser Gly Ser Glu Thr Pro Gly Thr Ser Glu Ser Ala Thr
                325                 330                 335

Pro Glu Ser Gly Pro Gly Thr Ser Thr Glu Pro Ser Glu Gly Ser Ala
                340                 345                 350

Pro Gly Thr Ser Thr Glu Pro Ser Glu Gly Ser Ala Pro Gly Thr Ser
            355                 360                 365

Thr Glu Pro Ser Glu Gly Ser Ala Pro Gly Thr Ser Thr Glu Pro Ser
    370                 375                 380

Glu Gly Ser Ala Pro Gly Thr Ser Thr Glu Pro Ser Glu Gly Ser Ala
385                 390                 395                 400

Pro Gly Thr Ser Thr Glu Pro Ser Glu Gly Ser Ala Pro Gly Ser Pro
                405                 410                 415

Ala Gly Ser Pro Thr Ser Thr Glu Glu Gly Thr Ser Thr Glu Pro Ser
                420                 425                 430

Glu Gly Ser Ala Pro Gly Thr Ser Glu Ser Ala Thr Pro Glu Ser Gly
            435                 440                 445

Pro Gly Ser Glu Pro Ala Thr Ser Gly Ser Glu Thr Pro Gly Thr Ser
    450                 455                 460

Glu Ser Ala Thr Pro Glu Ser Gly Pro Gly Ser Glu Pro Ala Thr Ser
465                 470                 475                 480

Gly Ser Glu Thr Pro Gly Thr Ser Glu Ser Ala Thr Pro Glu Ser Gly
                485                 490                 495

Pro Gly Thr Ser Thr Glu Pro Ser Glu Gly Ser Ala Pro Gly Thr Ser
                500                 505                 510

Glu Ser Ala Thr Pro Glu Ser Gly Pro Gly Ser Pro Ala Gly Ser Pro
            515                 520                 525

Thr Ser Thr Glu Glu Gly Ser Pro Ala Gly Ser Pro Thr Ser Thr Glu
    530                 535                 540

Glu Gly Ser Pro Ala Gly Ser Pro Thr Ser Thr Glu Glu Gly Thr Ser
545                 550                 555                 560

Glu Ser Ala Thr Pro Glu Ser Gly Pro Gly Thr Ser Thr Glu Pro Ser
```

```
            565                 570                 575

Glu Gly Ser Ala Pro Gly Thr Ser Glu Ser Ala Thr Pro Glu Ser Gly
            580                 585                 590

Pro Gly Ser Glu Pro Ala Thr Ser Gly Ser Glu Thr Pro Gly Thr Ser
            595                 600                 605

Glu Ser Ala Thr Pro Glu Ser Gly Pro Gly Ser Glu Pro Ala Thr Ser
            610                 615                 620

Gly Ser Glu Thr Pro Gly Thr Ser Glu Ser Ala Thr Pro Glu Ser Gly
625                 630                 635                 640

Pro Gly Thr Ser Thr Glu Pro Ser Glu Gly Ser Ala Pro Gly Ser Pro
                    645                 650                 655

Ala Gly Ser Pro Thr Ser Thr Glu Glu Gly Thr Ser Glu Ser Ala Thr
            660                 665                 670

Pro Glu Ser Gly Pro Gly Ser Glu Pro Ala Thr Ser Gly Ser Glu Thr
            675                 680                 685

Pro Gly Thr Ser Glu Ser Ala Thr Pro Glu Ser Gly Pro Gly Ser Pro
            690                 695                 700

Ala Gly Ser Pro Thr Ser Thr Glu Glu Gly Ser Pro Ala Gly Ser Pro
705                 710                 715                 720

Thr Ser Thr Glu Glu Gly Thr Ser Thr Glu Pro Ser Glu Gly Ser Ala
                    725                 730                 735

Pro Gly Thr Ser Glu Ser Ala Thr Pro Glu Ser Gly Pro Gly Thr Ser
            740                 745                 750

Glu Ser Ala Thr Pro Glu Ser Gly Pro Gly Thr Ser Glu Ser Ala Thr
            755                 760                 765

Pro Glu Ser Gly Pro Gly Ser Glu Pro Ala Thr Ser Gly Ser Glu Thr
            770                 775                 780

Pro Gly Ser Glu Pro Ala Thr Ser Gly Ser Glu Thr Pro Gly Ser Pro
785                 790                 795                 800

Ala Gly Ser Pro Thr Ser Thr Glu Glu Gly Thr Ser Thr Glu Pro Ser
                    805                 810                 815

Glu Gly Ser Ala Pro Gly Thr Ser Thr Glu Pro Ser Glu Gly Ser Ala
            820                 825                 830

Pro Gly Ser Glu Pro Ala Thr Ser Gly Ser Glu Thr Pro Gly Thr Ser
            835                 840                 845

Glu Ser Ala Thr Pro Glu Ser Gly Pro Gly Thr Glu Ser Ala Ser Arg
            850                 855                 860

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly Gly Arg Gly Gly Arg
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 69

Gly Gly Gly Arg Gly Gly
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 70

His His His His His His His His
1               5

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Gly Gly
1

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Cys Gly Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Asn Leu Tyr Phe Gln
1               5
```